US011945787B2

(12) United States Patent
Nathan et al.

(10) Patent No.: US 11,945,787 B2
(45) Date of Patent: Apr. 2, 2024

(54) SUBSTITUTED IMIDAZOLES FOR PREVENTING AND/OR TREATING CELL OR TISSUE NECROSIS

(71) Applicant: Ela Pharma Ltd, Tel Aviv (IL)

(72) Inventors: Ilana Nathan, Tel Aviv (IL); Boris Khalfin, Yeroham (IL)

(73) Assignee: Ela Pharma LTD, Tel Aviv (IL)

( * ) Notice: Subject to any disclaimer, the term of this patent is extended or adjusted under 35 U.S.C. 154(b) by 0 days.

(21) Appl. No.: 17/201,201

(22) Filed: Mar. 15, 2021

(65) Prior Publication Data

US 2021/0309620 A1 Oct. 7, 2021

Related U.S. Application Data

(62) Division of application No. 15/564,836, filed as application No. PCT/IL2016/050371 on Apr. 7, 2016, now Pat. No. 10,968,185.

(60) Provisional application No. 62/170,717, filed on Jun. 4, 2015, provisional application No. 62/143,821, filed on Apr. 7, 2015.

(51) Int. Cl.
C07D 233/04 (2006.01)
A61K 31/00 (2006.01)
A61K 31/167 (2006.01)
A61K 31/4045 (2006.01)
A61K 31/415 (2006.01)
A61K 31/4178 (2006.01)
A61K 31/4196 (2006.01)
A61K 31/426 (2006.01)
A61K 31/428 (2006.01)
A61K 31/4439 (2006.01)
A61K 31/454 (2006.01)
A61K 31/496 (2006.01)
A61K 31/536 (2006.01)
A61K 45/06 (2006.01)
A61P 25/00 (2006.01)
C07C 233/24 (2006.01)
C07D 233/44 (2006.01)
C07D 233/48 (2006.01)
C07D 265/22 (2006.01)
C07D 275/06 (2006.01)
C07D 277/42 (2006.01)
C07D 277/56 (2006.01)
C07D 405/06 (2006.01)
C07D 417/12 (2006.01)
C12N 5/077 (2010.01)
C12N 15/113 (2010.01)

(52) U.S. Cl.
CPC .......... C07D 265/22 (2013.01); A61K 31/00 (2013.01); A61K 31/167 (2013.01); A61K 31/4045 (2013.01); A61K 31/415 (2013.01); A61K 31/4178 (2013.01); A61K 31/4196 (2013.01); A61K 31/426 (2013.01); A61K 31/428 (2013.01); A61K 31/4439 (2013.01); A61K 31/454 (2013.01); A61K 31/496 (2013.01); A61K 31/536 (2013.01); A61K 45/06 (2013.01); A61P 25/00 (2018.01); C07C 233/24 (2013.01); C07D 233/44 (2013.01); C07D 233/48 (2013.01); C07D 275/06 (2013.01); C07D 277/42 (2013.01); C07D 277/56 (2013.01); C07D 405/06 (2013.01); C07D 417/12 (2013.01); C12N 5/0669 (2013.01); C12N 15/1137 (2013.01); C12Y 304/14001 (2013.01); C12Y 304/21036 (2013.01); C12N 2310/14 (2013.01); C12N 2501/30 (2013.01); C12N 2501/999 (2013.01)

(58) Field of Classification Search
CPC .................................................. C07D 233/04
USPC ...................................................... 548/347.1
See application file for complete search history.

(56) References Cited

FOREIGN PATENT DOCUMENTS

WO  WO-2016162870 A1 * 10/2016 ............. A61K 31/00

OTHER PUBLICATIONS

Jordan, V. C. Nature Reviews: Drug Discovery, 2, 2003, 205.*
Hackam, et al. JAMA, 296(14), 2006, 1731-1732.*

* cited by examiner

Primary Examiner — Douglas M Willis
(74) Attorney, Agent, or Firm — Frost Brown Todd LLP

(57) ABSTRACT

Inhibitor compounds and agents of Cathepsin C, CELA1, CELA3A and/or structurally related molecules thereto, compositions comprising the same, and uses thereof in the inhibition and/or prevention of cell and/or tissue necrosis are described. The compounds include imidazoles of Formula VI:

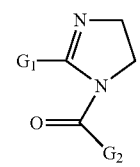

Formula VI wherein G1 is pyrrolidine, pyrazolidine, imidazolidine piperidine, or piperazine and G2 is alkyl, cycloalkyl, heterocycle, or aryl. The pyrrolidine, pyrazolidine, imidazolidine, piperidine, or piperazine of G1 and the alkyl, cycloalkyl, heterocycle, or aryl of G2 are optionally substituted with one or more substituents independently selected from the group consisting of halogen, NO2, CN, C1-C6 alkyl, C1-C6 haloalkyl, NH2, OH, OC1-C6 alkyl, C(O)H, C(O)C1-C6 alkyl, C(O)NH2, C(O)OH, and C(O)OC1-C6 alkyl. Variations applications for the described compounds, and combination therapies are further described as well.

16 Claims, 9 Drawing Sheets

Specification includes a Sequence Listing.

Figure 11

Elastase proteins clustalW multiple alignment:

```
SEQ ID NO: 10  ELA|ref|NP_005738.4|   MMLRLLSLLLVAVASGYGPPSSHSSRVVHGEDAVPYSWPWQVSLQYEK 50
SEQ ID NO: 25  CELA3B|ref|NP_031378.1| MMLRLLSLLLVAVASGYGPPSSRPSSRVVHGEDAVPYSWPWQVSLQYSS 50
SEQ ID NO: 27  CELA2A|ref|NP_254275.1| MIRTLLLSTLVAGALSCGRPTYPPYVTRVVGGEEARPNSWPWQVSLQYSS 50
SEQ ID NO: 8   CELA1|ref|NP_001962.3|  ---------KLSSRSTQDLPETN--ARVVGGTEAQRNSWPSQISLQYRS 40
                                        SEQ ID NO: 17                              SEQ ID NO: 18
                                              SEQ ID NO: 11 SEQ ID NO: 12

SEQ ID NO: 10  ELA|ref|NP_005738.4|   SGSFYHTCGGSLIAPDWVTACH          VVL         EGPEQVI 100
SEQ ID NO: 25  CELA3B|ref|NP_031378.1| SGSFYHTCGGSLIAPDWVTAGHCISSSRTYQVVLGEYDRAVREGPEQVI 100
SEQ ID NO: 27  CELA2A|ref|NP_254275.1| NGKWYHTCGGSLIASSWVLTAAHCTSSSNTYRVQLGRHNLYVAESGSLAV 100
SEQ ID NO: 8   CELA1|ref|NP_001962.3|  GGSRYHTCGGTLIRQNWVMTAAHCVDYQRTFRVVAGDHNLSQNDGTEQYV 90
                                        SEQ ID NO: 13                           SEQ ID NO: 19

SEQ ID NO: 10  ELA|ref|NP_005738.4|         VHPLSNSRCYAGGNDIALIKLSRSAQLGDAVQLASLPPAGDI 150
SEQ ID NO: 25  CELA3B|ref|NP_031378.1| PINSGDLFVHPLSNSGCVAGGNDIALIKLSRSAQLGDAVQLASLPPAGDI 150
SEQ ID NO: 27  CELA2A|ref|NP_254275.1| SVS--KIVVHKDWNSNQISGRDIALLKLAHPVSLTDKIQLACLPPAGTI 148
SEQ ID NO: 8   CELA1|ref|NP_001962.3|  SVQ--KIVVHPYWNSDNVAPGYDIALLRLAQSVTLNDIVQLGVLPQEGAI 138
                                                SEQ ID NO: 20  SEQ ID NO: 14

SEQ ID NO: 10  ELA|ref|NP_005738.4|   LPNETPCYITGWGRLYTNGPLPDKL         DYKHCSNWNWGSTVKR 200
SEQ ID NO: 25  CELA3B|ref|NP_031378.1| LPNETPCYITGWGRLYTNGPLPDKLQEALLPVVDYEHCSRNWWGSSVKR 200
SEQ ID NO: 27  CELA2A|ref|NP_254275.1| SNNIEPCYVGWGRLQTNGAVPDVLQQGRLLVVDIATCSSANWQSSVRT 198
SEQ ID NO: 8   CELA1|ref|NP_001962.3|  LANGSPCYITGWGKTKTNGQLAQTLQQAYLPSVDICSSSNWWGSTVKN 189
                                          SEQ ID NO: 15    SEQ ID NO: 21 SEQ ID NO: 22 SEQ ID NO: 16

SEQ ID NO: 10  ELA|ref|NP_005738.4|          -IRSGCNGDSGGPLNCPTEDGGWQVHGVTSFVS         249
SEQ ID NO: 25  CELA3B|ref|NP_031378.1| ISVCAGGD-IRSGCNGDSGGPLNCPTEDGGWQVHGVTSPVSAPGCNTREK 249
SEQ ID NO: 27  CELA2A|ref|NP_254275.1| SMICAGGDGVISSCNGDSGGPLNCQASDGRWQVHGIVSFGSRLGCNYYRK 248
SEQ ID NO: 8   CELA1|ref|NP_001962.3|  TMVCAGGDGVRSGCQGDSGGPLHCLV-GNYSVHGVTSFVSSRGCNVSRK 237
                                                                                SEQ ID NO: 23

SEQ ID NO: 10  ELA|ref|NP_005738.4|   PTVFTRVSAFIDWIEETIASH 270
SEQ ID NO: 25  CELA3B|ref|NP_031378.1| PTVFTRVSAFIDWIEETIASH 270
SEQ ID NO: 27  CELA2A|ref|NP_254275.1| PSVFTRVSNYIDWINSVIANN 269
SEQ ID NO: 8   CELA1|ref|NP_001962.3|  PTVFTQVSAYISWINNVIASN 258
```

SUBSTITUTED IMIDAZOLES FOR PREVENTING AND/OR TREATING CELL OR TISSUE NECROSIS

CROSS REFERENCE TO RELATED APPLICATIONS

This application claims the benefit of U.S. Provisional Application Ser. No. 62/143,821 filed Apr. 7, 2015 and U.S. Provisional Application Ser. No. 62/170,717 filed Jun. 4, 2015, both of which are hereby incorporated by reference in the entirety.

FIELD OF THE INVENTION

The present invention, in some embodiments thereof, relates to compositions and methods for treating and/or preventing cell necrosis and, more particularly, but not exclusively, to preventing or treating cell necrosis by means of downregulation of the expression and/or inhibiting the activity of intracellular Cathepsin C and/or CELA3A and/or CELA1 and/or targets structurally related thereto.

SEQUENCE LISTING

The contents of the file named "named 17201201_ST25.txt", which was created on May 21, 2021, and is 29,720 bytes in size, are hereby incorporated by reference in their entirety.

BACKGROUND OF THE INVENTION

Necrosis is considered to be a unique process of death of cells and living tissue, distinguished from apoptotic programmed cell death. Necrosis is characterized by cell swelling, chromatin digestion and disruption of the plasma and organelle membranes. Latter stages of necrosis are characterized by extensive DNA hydrolysis, vacuolation of the endoplasmic reticulum, organelle breakdown and cell lysis. The release of intracellular contents after plasma membrane rupture is a cause of inflammation seen with necrosis. Necrosis has long been viewed as an accidental pathological mode of cell death; however, recent studies have presented several lines of evidence indicating that necrosis is a regulated process.

Apoptosis, unlike necrosis, is energy dependent. Apoptosis is characterized by caspases activation and specific mode of DNA cleavage, however, both processes are absent in necrosis.

Cell death is a process that leads to the point of no return. For example, for liver cells submitted to total ischemia, cell death lies at approximately 150 minutes, which time scarcely any changes can be seen in histological sections. Necrosis is full-blown only after 12 to 24 hours. In other words, cells die long before any necrotic changes can be seen by light microscopy.

There are many causes of necrosis including, for example, prolonged exposure to injury, ischemia, anoxia, infarction, infection, cancer, poisons, venoms and inflammation. For instance, necrosis can arise from lack of proper care to a wound site.

Necrosis also plays a part in the pathology of several severe diseases including myocardial infarction, brain stroke, liver cirrhosis and other potentially lethal diseases. Heart failure, one of the biggest killers in the western world, is characterized by loss of heart muscle cells (cardiomyocytes). It is well established that cell death by necrosis has a significant role in the cardiomyocyte loss that accompanies heart failure.

There are currently several existing therapies for necrosis, including, early and aggressive surgical debridement and exploration of necrotic tissue, hyperbaric oxygen therapy, high pressure oxygen therapy, administration of antibiotics, administration of anti-inflammatory drugs and administration intravenous immunoglobulins. However, these are all used with mixed success and a significant morbidity and mortality is attributable to complications of necrosis.

There are many causes of necrosis including, for example, prolonged exposure to injury, ischemia, anoxia, infarction, infection, cancer, poisons, venoms and inflammation. For instance, necrosis can arise from lack of proper care to a wound site. Necrosis also plays a part in the pathology of several severe diseases including myocardial infarction, brain stroke, liver cirrhosis and other potentially lethal diseases. Heart failure, one of the biggest killers in the western world, is characterized by loss of heart muscle cells (cardiomyocytes). It is well established that cell death by necrosis has a significant role in the cardiomyocyte loss that accompanies heart failure.

Furthermore, the necrotic process contributes to problems associated with preserving a harvested organs and tissues prior to transplantation. Particularly, the process is involved in the deterioration of cardiac tissue during storage of a donor heart resulting in poor quality of same. Other examples are preservation and transplantation of skin flap, kidney, liver and other tissues. Necrosis is also involved in cytotoxicity to healthy tissues during chemotherapy.

Currently the only treatment for necrosis is hyperbaric oxygen therapy. However, these is no drug treatment for necrosis per se. That is why significant morbidity and mortality is attributable to complications of necrosis.

Certain elastases that catalyze the degradation of proteins have been preliminarily shown to be involved in necrotic cell death, and treatment of affected cells with certain (neutrophil elatase) inhibitor compounds prevented/treated cell necrosis in vitro when such inhibitors were used at hundreds micromolar concentrations (WO2003079969).

While these initial findings are encouraging, given the breadth of family members, the difficulty in a priori defining high affinity inhibitors that are effective in preventing/treating necrosis, and the lack of understanding which elastase family member is an effective target for treatment and prevention of necrosis and ideal therapy for same to date remains elusive.

SUMMARY OF THE INVENTION

This invention provides for the surprising finding that inhibition of expression and/or activity of certain elastase-like proteolytic enzymes results in highly effective prevention and treatment of cell and tissue necrosis. Surprisingly, specific inhibition of Cathepsin C, CELA1, CELA3A or other structurally related molecules thereto, prevents and/or treats cellular and/or tissue necrosis.

In particular, this invention provides, inter alia, for the identification of a very specific series of targets, which in some aspects are proteolytic enzymes and in some aspects may also exhibit elastase activity, whose inhibition with compounds, agents and compositions as described herein, could be accomplished. In some aspects, specific in vitro inhibition using compounds as herein described provided at concentrations several orders of magnitude less than previous elastase inhibitors were surprisingly effective in preventing and/or treating and/or halting/abrogating necrosis.

In some aspects, such enhanced affinity is related to the identification of more specific targets, for applications in the compositions, methods, uses, agents and compounds as herein described.

In some aspects, such enhanced affinity may in some embodiments, reflect the identification of a different subset of active enzymes in the necrosis pathway serving as highly effective therapeutic targets.

In some aspects, such enhanced affinity is related to the identification of a class of targets with different activity than previously identified targets for applications in reducing cell and tissue necrosis.

The present invention provides therefore, inter alia, a method for treating and preventing cell and tissue necrosis and diseases associated therewith, by administering to a subject in need thereof an effective amount of an agent that specifically inhibits expression and/or activity of Cathepsin C, CELA1, CELA3A or enzymes structurally related thereto.

Such agent that specifically inhibits expression and/or activity of Cathepsin C, CELA1, CELA3A or a structurally related enzyme thereto, as further described herein, may be a polynucleotide or polypeptide inhibitor, as well as a defined chemical compound, as further described herein.

This invention provides, in some embodiments, a compound characterized by the structure of Formula I:

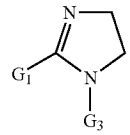

Formula I wherein G1 is substituted or unsubstituted pyrrolidine, substituted or unsubstituted piperidine, substituted or unsubstituted piperazine, substituted or unsubstituted imidazolidine, or substituted or unsubstituted pyrazolidine; and
G3 is characterized by the following structure:

or G3 is substituted or unsubstituted alkyl, substituted or unsubstituted aryl or substituted or unsubstituted cyloalkyl;
wherein G2 is substituted or unsubstituted alkyl, substituted or unsubstituted aryl, substituted or unsubstituted cyloalkyl or substituted or unsubstituted heterocycle; or
a compound characterized by the structure of Formula II:

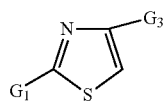

Formula II wherein G1 is substituted or unsubstituted pyrrolidine, substituted or unsubstituted pyridine, substituted or unsubstituted aryl, substituted or unsubstituted piperidine, substituted or unsubstituted piperazine, substituted or unsubstituted imidazolidine, or substituted or unsubstituted pyrazolidine; and
G3 is characterized by the following structure:

or G3 is substituted or unsubstituted alkyl, substituted or unsubstituted aryl or substituted or unsubstituted cyloalkyl;
wherein G2 is substituted or unsubstituted alkyl, substituted or unsubstituted aryl, substituted or unsubstituted cyloalkyl or substituted or unsubstituted heterocycle; or
a compound characterized by the structure of Formula III:

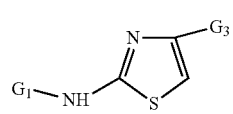

Formula III wherein G1 is substituted or unsubstituted pyrrolidine, substituted or unsubstituted pyridine, substituted or unsubstituted aryl, substituted or unsubstituted piperidine, substituted or unsubstituted piperazine, substituted or unsubstituted imidazolidine, or substituted or unsubstituted pyrazolidine; and
G3 is characterized by the following structure:

or G3 is substituted or unsubstituted alkyl, substituted or unsubstituted aryl or substituted or unsubstituted cyloalkyl;
wherein G2 is substituted or unsubstituted alkyl, substituted or unsubstituted aryl, substituted or unsubstituted cyloalkyl or substituted or unsubstituted heterocycle; or
a compound selected from the group consisting of:
3,4-bis((2-(pyrrolidin-1-yl)ethyl)amino)-1,2,5-thiadiazole 1,1-dioxide;
cyclopropyl(2-(5-isopropylisoxazol-3-yl)pyrrolidin-1-yl)methanone;
6-bromo-2-(3,5-dimethoxyphenyl)-4benzo[d][1,3]oxazin-4-one
6-methyl-5-((2-methylpiperidin-1-yl)sulfonyl)pyrimidine-2,4(1H,3H)-dione;
N-methyl-4,5,6,7,8,9-hexahydro-1H-cycloocta[c]pyrazole-3-carboxamide;
2-(5-(pyridin-4-yl)-2H-tetrazol-2-yl)acetic acid;
2-(furan-2-yl)-5,6,7,8-tetrahydro-4H-benzo[4,5]thieno[2,3-d][1,3]oxazin-4-one;
3-((5-acetamido-1H-1,2,4-triazol-3-yl)thio)propanoic acid;
N,N'-(oxybis(4,1-phenylene))bis(2-methylpropanamide);
7-(4-ethylpiperazin-1-yl)-5,6-dimethyl-[1,2,4]triazolo[1,5-a]pyrimidine;

7-fluoro-10-(2-(4-isopropylpiperazin-1-yl)-2-oxoethyl)-2,3-dihydro-1H-benzo[e]pyrrolo[1,2-a][1,4]diazepine-5,11(10H,11aH)-dione;
2-(tert-butyl)-3-(1-methyl-1H-benzo[d]imidazol-2-yl)-4-oxo-4H-chromen-7-yl pivalate;
3-methyl-8-(piperidin-1-yl)-1H-purine-2,6(3H,7H)-dione;
2-(3-bromophenyl)-4-oxo-4H-benzo[d][1,3]oxazin-6-yl acetate;
N-(1-ethyl-3,5-dimethyl-1H-pyrazol-4-yl)-3,4,5-trimethoxybenzamide;
5-ethyl-N-(pyridin-2-ylmethyl)-5H-[1,2,4]triazino[5,6-b]indol-3-amine;
3-((4-chloro-1H-pyrazol-1-yl)methyl)-N-(2-(3-fluorobenzamido)ethyl)-1,2,4-oxadiazole-5-carboxamide;
1-(4-(methylthio)benzyl)-4-tosylpiperazine;
2-(2-ethylphenylsulfonamido)-5-(4-ethylpiperazin-1-yl) benzoic acid;
4((2-methylindolin-1-yl)sulfonyl)benzoic acid;
6-bromo-2-(3,5-dimethoxyphenyl)-4H-benzo[d][1,3] oxazin-4-one;
2-amino-N-(2,4-difluorophenyl)pyrimidine-5-sulfonamide;
3-methyl-8-(piperidin-1-yl)-1H-purine-2,6(3H,7H)-dione;
5-chloro-N-(2-oxo-1-phenylpyrrolidin-3-yl)thiophene-2-sulfonamide;
3-(pyrrolidin-1-ylsulfonyl)benzoic acid;
(3,5-dimethyl-1H-pyrazol-1-yl)(3,4,5-trimethoxyphenyl) methanone;
N-(3,4-difluorophenyl)-2-(8-fluoro-5,11-dioxo-2,3,11,11a-tetrahydro-1H-benzo[e]pyrrolo[1,2-a][1,4]diazepin-10(5H)-yl)acetamide;
5-(cyclohexylmethyl)-3-(pyridin-2-yl)-1,2,4-oxadiazole;
ethyl 5-methyl-4-(2-((4-methylbenzyl)amino)-2-oxoethyl)-7-phenyl-4,7-dihydro-[1,2,4]triazolo[1,5-a]pyrimidine-6-carboxylate;
[1,2,4]triazolo[1,5-a]pyrimidine-2-carboxylic acid;
1-(2-(piperidin-1-yl)-4,5-dihydro-1H-imidazol-1-yl)butan-1-one;
(4-(6-chloro-[1,2,4]triazolo[4,3-a]pyridin-3-yl)piperazin-1-yl)(1-phenylcyclopropyl)methanone;
N-(2,4-difluorophenyl)-2-(5,11-dioxo-2,3,11,11a-tetrahydro-1H-benzo[e]pyrrolo[1,2-a][1,4]diazepin-10 (5H)-yl)acetamide; and
Ethyl-2,3-dihydro-3-oxo-1,2-benzisothiazole-2-acetate-1,1-dioxide; or a pharmaceutical salt thereof, or any combination thereof, for use in treating or preventing cellular or tissue necrosis or a disease related thereto.

A pharmaceutical composition comprising a compound as defined immediately hereinabove is to be understood to constitute an embodied aspect of this invention, as well.

This invention describes the first medical use of a compound as defined immediately hereinabove, which use is to be understood to constitute an embodied aspect of this invention as well.

This invention further provides for methods of treatment of cell or tissue necrosis or a disease or condition relating thereto, with such method comprising administering an effective amount of a compound as defined immediately hereinabove, or a pharmaceutical composition comprising same to a subject in need thereof, or contacting an affected cell or tissue with same, thereby treating cell or tissue necrosis or a condition related thereto.

This invention also provides for the use of an effective amount of a compound as defined immediately hereinabove, or a pharmaceutical composition comprising same in the manufacture of a medicament for use in treating a disease or condition related to cell or tissue necrosis occurring in a subject.

In some aspects, this is the first demonstrated medical use of the embodied compounds as herein described and the invention contemplates same. In some aspects, compounds as described herein or structurally related thereto, possessing a defined activity of specifically inhibiting the activity of Cathepsin C, CELA1, CELA3A or a structurally related enzyme thereto are envisioned aspects of this invention.

In some embodiments, a compound of this invention is defined by its selective binding to Cathepsin C, CELA1, CELA3A or a structurally related enzyme thereto or a combination thereof with a minimal affinity of Kd $10^{-7}$ M or lower. In some embodiments, a compound of this invention is defined by its less selective binding to CELA2A, CELA3B, or Cathepsins A, B, D, E, G, H, K, L1, L2, O, S, W or Z or a combination thereof, which in some embodiments, exhibit a minimal affinity of Kd $10^{-6}$ M or higher.

In some embodiments, this invention provides a composition comprising any combination of the compounds as herein described. In some embodiments, the composition comprising an effective amount of any combination of the compounds as herein described, or any single compound as herein described. In some embodiments, the composition will further comprise a pharmaceutically acceptable carrier or excipient.

According to some embodiments of the invention, the pharmaceutical composition is formulated for penetrating a cell membrane.

According to some embodiments of the invention, the pharmaceutical composition comprises a lipid vesicle.

In some embodiments, the composition will further comprise an anti-apoptotic agent or an anti-aging agent. According to some embodiments of the invention, the anti-aging agent is selected from the group consisting of an antioxidant, a phytochemical, a hormone, metformin and a fatty acid.

In some embodiments, this invention provides an inhibitor agent of Cathepsin C, CELA1, CELA3A, or enzymes structurally related thereto, wherein said agent is a polynucleotide selected from the group consisting of an antisense, an siRNA, a microRNA, a Ribozyme and a DNAzyme, directed to a nucleic acid region selected from the group consisting of SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35 and SEQ ID NO: 36.

In some embodiments, the CELA3A, CELA1, or Cathepsin C inhibitor agent, is a polynucleotide, which polynucleotide agent shares at least 95% identity with the polynucleotide of the nucleic acid sequence as set forth in SEQ ID NO: 1, SEQ ID NO: 2 or SEQ ID NO: 3.

In some embodiments, the CELA3A, CELA1, or Cathepsin C inhibitor agent, is a polynucleotide, which polynucleotide agent specifically hybridizes with a CELA1 or CELA3A sequence or a combination thereof and does not hybridize to a CELA2A or CELA3B sequence under moderate to stringent hybridization conditions.

In some embodiments, the CELA3A, CELA1, or Cathepsin C inhibitor agent, is a polynucleotide, which polynucleotide agent specifically hybridizes to Cathepsin C and does not hybridize to Cathepsins A, B, D, E, G, H, K, L1, L2, O, S, W or Z under moderate to stringent hybridization conditions.

In some embodiments, the CELA3A, CELA1, or Cathepsin C inhibitor agent, is a polynucleotide, which polynucleotide agent shares at least 95% identity with the polynucleotide of the nucleic acid sequence as set forth in SEQ ID NO: 1. In some embodiments, the CELA3A, CELA1, or Cathepsin C inhibitor agent, is a polynucleotide, which polynucleotide agent shares at least 95% identity with the polynucleotide of the nucleic acid sequence as set forth in SEQ ID NO: 2. In some embodiments, the CELA3A, CELA1, or Cathepsin C inhibitor agent, is a polynucleotide, which polynucleotide agent shares at least 95% identity with the polynucleotide of the nucleic acid sequence as set forth in SEQ ID NO: 3.

In some embodiments, this invention provides a nucleic acid construct comprising any polynucleotide inhibitor agent as herein described.

In some embodiments, this invention provides a CELA3A, CELA1, or Cathepsin C inhibitor agent, wherein said agent is an antibody specifically binding to and inhibiting or preventing function of a polypeptide comprising a sequence selected from the group consisting of SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22 and SEQ ID NO: 23.

According to some embodiments of the invention, the high affinity binding molecule is an antibody or an antigen binding fragment thereof, including Fab or scFv fragments, as will be appreciated by the skilled artisan.

The present invention provides compositions and methods for treating and preventing necrosis of cells and diseases associated therewith.

In additional embodiments, the invention is directed to the use for prevention and treatment of necrosis, of specific small inhibitory molecules that were found to inhibit cell necrosis at particularly low concentrations. The list of molecules includes small inhibitory compounds that belong to various chemical families, for example, to 2-aminoimidazolines, 2-aminothiazolines and isoxazoles. The present invention also provides a variety of small molecule inhibitors for use in the treatment and/or prevention of a disease or a medical condition associated with cell necrosis. In yet a further embodiment there is provided a use of small molecule inhibitor in the manufacture of a medicament for the treatment and/or prevention of a disease or a medical condition associated with cell necrosis.

In some embodiments, the invention contemplates use of any compound as herein described, or use of any Cathepsin C, CELA1, CELA3A or a structurally related enzyme thereto for the treatment, abrogation, inhibition or prevention of cellular necrosis. In some embodiments, the cells undergoing necrosis are selected from the group consisting of a brain cell, a neuronal cells, a purkinje cell, a hypocampal pyramidal cell, a glial cell, a myocardial cell, a muscle cell, a keratinocyte, an epidermal cell, a bone or cartilage cell, a pancreatic cell, a cardiac cell, a muscle cell, a liver cell, a respiratory cell or a lung cell a hepatocyte, a kidney cell, a gastrointestinal cell, a spleen cell, a hematopoetic cell, a lymphocyte, a macrophage, a thymocyte, a fibroblast, an epithelial cell, a parenchymal cell a bronchial epithelial cell, a nephrotic tubular cell, a glomerulus capillary cell, and a lung epithelial cell, and stem cells, a gonadal cell, a spermatozoa, an ovum, a fertilized ovum, an embryonic cell, a stem cell and retina cell.

In some embodiments, the invention contemplates use of any compound as herein described, or use of any CELA3A, CELA1, or Cathepsin C inhibitor agent for the treatment, abrogation, inhibition or prevention of a disease or condition associated with cell or tissue necrosis. In some embodiments, the disease or medical condition is selected from the group consisting of a neurodegenerative disease, e.g. a dementia, a Parkinson's disease, an Alzheimer's disease, Huntington's disease, multiple sclerosis Amyotrophic lateral sclerosis (ALS), a macular degeneration, an age-related macular degeneration (AMD), an acute retinal necrosis (ARN), a progressive outer retinal necrosis, a muscular dystrophy, a leukemia, a lymphoma, a neonatal respiratory distress, an asphyxia, an incarcerated hernia, a diabetes mellitus, a tuberculosis, an endometriosis, a vascular dystrophy, a psoriasis, a cold injury, an iron-load complication, a complication of steroid treatment, an ischemic heart disease, myocardial infarction, a reperfusion injury, a cerebrovascular disease or damage, e.g. a stroke or a traumatic brain injury, a gangrene, a pressure sore, a pancreatitis, a severe acute pancreatitis, a hepatitis, a chronic hepatitis, a cirrhosis, a hemoglobinuria, a bacterial sepsis, a viral sepsis, a burn, a hyperthermia, a Crohn's disease, a celiac disease, a compartment syndrome, a necrotizing procolitis, a Stevens-Johnson Syndrome (SJS), a toxic epidermal necrosis (TEN), a cystic fibrosis, a rheumatoid arthritis, an osteomyelitis, a necrotizing fasciitis, a nephrotoxicity, a spinal cord injury, a glomerulonephritis, an acute tubular necrosis, a renal cortical necrosis, a degenerative arthritis, a tyrosemia, a multiple sclerosis, a congenital mitochondrial disease, a metabolic inherited disease, a mycoplasmal disease, an anthrax infection, bacterial infection, a viral infection, an Ebola infection, an Anderson's disease, a congenital mitochondrial disease, a phenylketonuria, a placental infarct, a syphilis, an aseptic necrosis, an avascular necrosis, an alcoholism, a necrosis associated with administration and/or self-administration with, and/or exposure to, cocaine, drugs, e.g. paracetamol or doxorubicin; chemical toxins, agrochemicals, heavy metals, warfare organophosphates, or spider or snake venoms; a necrosis associated with dermal fillers administration; a necrosis associated with ectopic drug administration, such as extravasation of dextrose solution, chemotherapeutic drugs; a chemotherapy-induced necrosis, a radiation induced necrosis, maintenance of transplant tissue and aging.

In some embodiments, the invention contemplates use of any compound as herein described, or use of any inhibitor agent of Cathepsin C, CELA1, CELA3A or a structurally related enzyme thereto for improving the appearance or quality of skin and in some embodiments, cosmetic use of the compounds and agents as herein described is contemplated.

Also provided a pharmaceutical composition comprising at least one pharmaceutically acceptable carrier and a therapeutically effective amount of a compound as herein described or any inhibitor agent of Cathepsin C, CELA1, CELA3A or a structurally related enzyme thereto as herein described.

In some embodiments the any inhibitor agents of Cathepsin C, CELA1, CELA3A or a structurally related enzyme thereto of this invention will bind to CELA3A, CELA1, or Cathepsin C or a combination thereof, with a minimal affinity of Kd $10^{-7}$ M or lower, and will bind to CELA2A and/or CELA3B, and/or Cathepsins A, B, D, E, G, H, K, L1, L2, O, S, W or Z with a minimal affinity of at least 10 times higher Kd, as compared to that of the minimal binding affinity for CELA3A, CELA1, or Cathepsin C.

In some embodiments, such inhibitor agents may bind CELA3B and/or OCIAD1 with a minimal affinity of Kd $10^{-7}$ M or lower. In some embodiments, according to this aspect, the inhibitor agent will have a sequence sharing at least 95% identity with that described in SEQ ID NO: 3.

In some embodiments, such inhibitor agents may bind CELA3B and/or OCIAD1 with higher affinity than binding to CELA2A and/or Cathepsins A, B, D, E, G, H, K, L1, L2, O, S, W or Z, having a minimal affinity as described hereinabove. In some embodiments, according to this aspect, the inhibitor agent will have a sequence sharing at least 95% identity with that described in SEQ ID NO: 3.

In some aspects, the invention contemplates conservative substitutions for the polynucleotides as herein described, as will be appreciated by the skilled artisan.

In some further embodiments, it is provided a method of treating a medical disease or condition associated with cell necrosis in a subject in need thereof. The method comprises administering to the subject a therapeutically effective amount any agent or compound as herein described including analogues, derivatives, fragments, isomers or salts thereof, as appropriate. In further preferred embodiments the subject is a human or a non-human mammal.

In some embodiments, the agent or compound as herein described is effective when the cells are at an early stage of necrosis. In some further embodiments, the agent or compound as herein described is active when the cells have been subjected to a necrotic signal.

According to a further embodiment, this invention provides a method of treating and/or preventing aging in a subject in need thereof, the method comprising: (a) administering to the subject any agent or compound as herein described or any combination of same; and (b) administering to the subject an anti-aging agent, thereby treating and/or preventing aging.

According to some embodiments of the invention, the cell is a necrotic cell.

According to some embodiments of the invention, the method further comprises administering to the subject an anti-apoptotic agent such as caspase inhibitor According to some embodiments of the invention, the anti-apoptotic agent is administered prior to, concomitantly with or following administration of the agent or compound as herein described. According to some embodiments of the invention, the method is effected in-vivo.

According to some embodiments of the invention, the pharmaceutical composition is formulated for penetrating a cell membrane. According to some embodiments of the invention, the pharmaceutical composition comprises a lipid vesicle According to some embodiments of the invention, the anti-aging agent is selected from the group consisting of an antioxidant, a phytochemical, a hormone, metformin and a fatty acid.

According to a further aspect of the invention it provided a method and compositions for storing and preserving the functional integrity of organs, tissues and cells via preventing and/or inhibiting induction of necrosis therein.

In some aspects, the invention provides a method for preserving a human, a human-compatible or a non-human harvested organ, tissue or cell in need of preservation prior to implantation, comprising transplantation or re-implantation of heart, kidney, liver, skin, lungs and other organs and tissues. Furthermore the present invention provides a method for improved preservation of harvested organs following a resuscitation. The present invention further allows for a more efficient transportation of same to alternate geographic locations during the preservation period. Furthermore the present invention provides a method for improvement of cell viability during the recovery process of the cells further to a preservation, for instance following thawing, and an evaluation of the period prior to the implantation. In addition the present invention provides a method for preservation and maintenance of a reproduction associated cells, i.e. a gonadal cell, a spermatozoa, an ovum, a fertilized ovum, and/or an embryonic cell, during their maintenance, preservation and implantation.

In one embodiment, the composition for preserving a biological tissue comprises a physiological salt solution, a substrate for the production of ATP and one of the inhibitors, as disclosed herein, thereby preventing or inhibiting the necrosis of the cells. Optionally, the substrate for the production of ATP is phosphocreatine, creatine ethyl ester, dicreatine malate, creatine gluconate, fructose, sucrose, ribose, hexose or pentose. Alternatively, the substrate for the production of ATP is creatine orotate, creatine monohydrate, adenosine, or dextrose/glucose.

In some embodiments the agent or compound as herein described is a small molecule, as understood in the art.

In some embodiments, the agent or compound as herein described is a polynucleotide agent, selected from the group consisting of an antisense, a siRNA, a microRNA, a Ribozyme and a DNAzyme. Sometimes the polynucleotide agent is According to one embodiment of the present invention provided herein a method of preventing or inhibiting necrosis of a cell, the method comprising administering to a cell that is subjected to a necrotic signal a therapeutically effective amount of an agent which specifically downregulates expression and/or inhibits an activity at least one of intracellular CELA3, CELA1, and/or Cathepsin C, thereby preventing or inhibiting the necrosis of the cell.

In some embodiments, the agent or compound as herein described has greater specificity for CELA3A than for CELA3B, but the skilled artisan will appreciate that inhibition of either or both targets is envisioned as encompassing a part of the invention, including agents defined that specifically interact with same and/or agents as defined that specifically inhibit the activity of same.

In a particularly preferred embodiment, provided a method of preventing or inhibiting necrosis of a cell, the method comprising administering to a cell that is subjected to a necrotic signal a therapeutically effective amount of an agent which specifically downregulates an expression and alternatively or additionally inhibits an activity of CELA3 including CELA3A and CELA3B.

According to a further embodiment of the present invention provided a method of treating a medical disease or condition associated with cell necrosis in a subject in need thereof, the method comprising administering to the subject a therapeutically effective amount of an agent which specifically downregulates an expression and alternatively or additionally inhibits an activity of at least one of intracellular Cathepsin C, CELA1, CELA3A or a structurally related enzyme thereto and/or in a cell of the subject, which in some embodiments, may provide for less optimal activity than inhibition of CELA3A, but which effect on expression and/or activity is nonetheless useful, for example and in some embodiments, CELA3B, thereby treating the condition associated with the cell necrosis.

In another preferred embodiment, the invention is also directed to the use of an isolated polynucleotide that hybridizes specifically to CELA3A and/or CELA1 but not to CELA2A or less optimally to CELA3B under moderate to stringent hybridization conditions.

In a particularly preferred embodiment, the isolated polynucleotide hybridizes specifically to CELA3A.

In a particularly preferred embodiment, the invention is directed to the use of a small molecule that inhibits specifically at least one of intracellular Cathepsin C, CELA1, CELA3A or a structurally related enzyme thereto.

According to an aspect of some embodiments of the present invention the small molecule binds with a minimal affinity of Kd $10^{-7}$ M and lower to specifically at least one of intracellular Cathepsin C, CELA1, CELA3A or a structurally related enzyme thereto, and binds to CELA2A and/or CELA3B and/or to Cathepsins A, B, D, E, G, H, K, L1, L2, O, S, W or Z with a minimal affinity of at least 10 times higher Kd.

In some embodiments, the agent or compound as herein described binds with less affinity to CELA3B than to CELA3A, but an agent or compound as herein described binds CELA3B with greater affinity than to CELA2A and/or Cathepsins A, B, D, E, G, H, K, L1, L2, O, S, W or Z under moderate to stringent hybridization conditions.

According to another embodiment of the present invention provided herein a high affinity molecule, which binds to at least one domain composed of folded amino acid sequence of at least one of intracellular Cathepsin C, CELA1, CELA3A or a structurally related enzyme thereto.

According to an aspect of some embodiments of the present invention provided an antibody, which binds with a minimal affinity of Kd $10^{-7}$ M and lower to CELA3A and CELA1, but binds to CELA2A or CELA3B with a minimal affinity of at least 10 times higher Kd.

According to an aspect of some embodiments of the present invention there is provided an antibody which binds with a minimal affinity of Kd $10^{-7}$ M and lower to Cathepsin C but binds to Cathepsins A, B, D, E, G, H, K, L1, L2, O, S, W or Z with a minimal affinity of at least 10 times higher Kd.

According to an aspect of some embodiments of the present invention there is provided a pharmaceutical composition comprising the isolated polynucleotide of the present invention, the high affinity molecule of the present invention, or the antibody of the present invention and a pharmaceutically acceptable carrier.

According to an aspect of some embodiments of the present invention there is provided a pharmaceutical composition comprising the isolated polynucleotide of the present invention, an anti-apoptotic agent and a pharmaceutically acceptable carrier.

In some embodiments, the invention provides a vector, conjugate, liposome or carrier comprising the polynucleotide or polypeptides as herein described and compositions comprising same.

According to an aspect of some embodiments of the present invention there is provided a method of treating and/or preventing aging in a subject in need thereof, the method comprising: (a) administering to the subject an agent which specifically downregulates an expression and alternatively or additionally inhibits an activity of at least one of intracellular Cathepsin C, CELA1, CELA3A or a structurally related enzyme thereto in a cell of the subject; and (b) administering to the subject an anti-aging agent, thereby treating and/or preventing aging.

According to an aspect of some embodiments of the present invention there is provided a pharmaceutical composition comprising the isolated polynucleotide of the present invention, an anti-aging agent and a pharmaceutically acceptable carrier.

According to some embodiments of the invention, the compounds, agents, compositions, uses and methods of the invention may be applied to any cell that has been subjected to a necrotic signal.

According to some embodiments of the invention, the amount of the agent is selected to cause conversion of cell necrosis to cell apoptosis.

According to some embodiments of the invention, the method further comprising administering to the subject an anti-apoptotic agent.

According to some embodiments of the invention, the anti-apoptotic agent is selected from the group consisting of —[R]—N-[2-heptyl]-methylpropargylamine (R-2HMP), vitamin E, vitamin D, caspase inhibitors, agents which downregulate antiapoptotic proteins and the hydrophilic bile salt ursodeoxycholic acid.

According to some embodiments of the invention, the anti-apoptotic agent is administered prior to, concomitantly with or following administration of the agent which specifically downregulates an expression and alternatively or additionally inhibits an activity of the Cathepsin C, CELA1, CELA3A or a structurally related enzyme thereto, where in some embodiments, the activity may be more preferential for CELA3A than CELA3B.

According to some embodiments of the invention, the method is effected in-vivo.

The present invention is also directed to a method for inhibition of at least one of intracellular CELA3A or structurally similar enzyme, CELA1, and/or Cathepsin C in order to provide a protection against necrosis in-vitro.

In some embodiments, this invention provides a compound characterized by the structure of Formula VI:

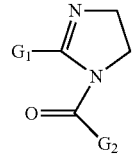

Formula VI

Wherein:

$G_1$ is optionally substituted NH-pyrrolidine, optionally substituted NH-piperidine, optionally substituted NH-piperazine, optionally substituted NH-imidazolidine, optionally substituted NH-pyrazolidine, optionally substituted NH-aryl, optionally substituted NH-cycloalkyl, optionally substituted pyrrolidine, optionally substituted piperidine, optionally substituted piperidin, optionally substituted piperazine, optionally substituted imidazolidine, or optionally substituted pyrazolidine; $G_2$ is optionally substituted alkyl, optionally substituted aryl, optionally substituted cyloalkyl or optionally substituted heterocycle;

Wherein:

If $G_1$ is unsubstituted pyrrolidine, then $G_2$ is not alkyl, cyclopentyl, alkylcyclopentyl or furan; or If $G_1$ is Piperidine then $G_2$ is not alkyl; and If $G_1$ is Piperazine, then $G_2$ is not alkyl or furan.

In some embodiments, $G_1$ is pyrrolidine and $G_2$ is ethyl or furan. In some embodiments, $G_1$ is substituted piperazine and $G_2$ is furan or phenyl and in some embodiments, $G_1$ is piperidine and $G_2$ is cyclopentyl, furan or phenyl. In some embodiments, $G_1$ is optionally substituted imidazolidine or optionally substituted pyrazolidine.

In some embodiments, this invention provides a compound characterized by the structure of Formula VII:

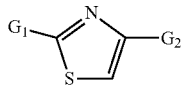

Formula VII

Wherein:

G₁ is optionally substituted NH-pyrrolidine, optionally substituted NH-piperidine, optionally substituted NH-piperazine, optionally substituted NH-imidazolidine, optionally substituted NH-pyrazolidine, optionally substituted NH-pyridine, optionally substituted NH-aryl, optionally substituted NH-cycloalkyl, optionally substituted pyrrolidine, optionally substituted piperidine, optionally substituted piperidine, optionally substituted piperazine, optionally substituted imidazolidine, optionally substituted pyrazolidine or optionally substituted aryl;

G₂ is

or optionally substituted alkyl, optionally substituted aryl or optionally substituted cyloalky; and G₄ is optionally substituted pyrrolidine, optionally substituted piperidine, optionally substituted piperazine, optionally substituted imidazolidine or optionally substituted pyrazolidine;

Wherein:

If G₁ is Piperidine then G₄ is not pyrrolidine or G₂ is not optionally substituted aryl; or If G₁ is imidazolidine, then G₂ is not optionally substituted aryl; or If G₁ is optionally substituted NH-pyridine, then G₂ is not optionally substituted aryl; or If G₁ is optionally substituted NH-aryl, then G₂ is not optionally substituted aryl; or If G₁ is optionally substituted pyridine, then G₂ is not optionally substituted aryl.

In some embodiments, according to this aspect, G₁ is optionally substituted NH-pyridine, G₂ is

wherein G₄ is pyrrolidine, or G₂ is haloaryl and in some embodiments, according to this aspect G₁ is substituted NH-aryl and G₂ is

wherein G₄ is pyrrolidine.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 1 illustrates time and dose response of KCN induced necrosis. Nuclear morphology was determined by double staining with acridine orange and ethidium bromide.

FIG. 4A is a bar graph illustrating cells which were transfected with control siRNA or siRNA for the specific enzymes and were treated with or without KCN for 7 hours and then LDH release from the cells was determined. Transfection with control siRNA had no effect by itself. *P<0.001; FIG. 4B depicts photographs illustrating Western Blots demonstrating the down regulation of specified proteins due to the treatment with appropriate siRNAs.

FIGS. 7A-B illustrate PC12 cells, which were treated with or without KCN for 5 hours in the presence or absence of different concentrations of elastase inhibitor II or III, respectively. LDH release from the cells was then determined; *P<0.05.

FIG. 11 is a sequence alignment of amino acid sequences of elastase proteins CELA1 (SEQ ID NO: 8), CELA2A (SEQ ID NO: 27), CELA3A (SEQ ID NO: 10) and CELA3B (SEQ ID NO: 25) indicating amino acid target sites (indicated in yellow for CELA1 and in green for CELA3A) as determined by clustalW2 software, from the European Bioinformatics Institute (EBI).

DETAILED DESCRIPTION OF THE INVENTION

Figure 1:
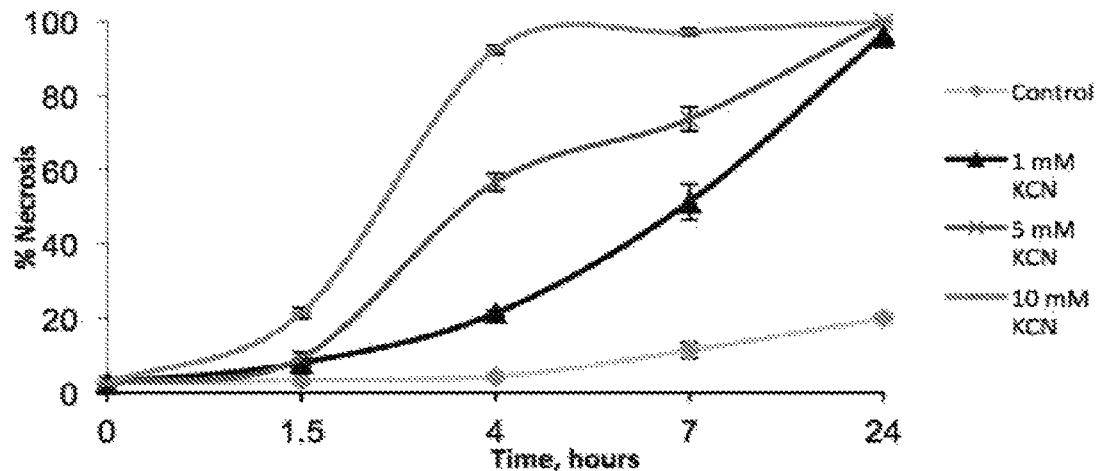
FIG. 1 is a line graph depicting the kinetics of KCN-induced cell death in U-937 cells.

The present invention, in some embodiments, relates to compositions and methods for treating and/or preventing cell or tissue necrosis and/or diseases and conditions related thereto and, more particularly, but not exclusively, to preventing or treating cell or tissue necrosis by means of downregulating the expression and/or inhibiting the activity of at least one of intracellular CELA3, which in some embodiments is preferentially CELA3A or structurally related enzymes, or in some embodiments, CELA1, or in some embodiments, Cathepsin C or in some embodiments, any combination thereof.

Surprisingly, it has herein been found that certain proteolytic enzymes are specifically involved in early stages of necrosis and can serve as targets for the defining of a compound or agent to downregulate expression or inhibit activity of same or both, resulting in prevention of necrosis, treatment of necrosis or a combination thereof.

Cathepsin C (CTSC), also known as dipeptidyl peptidase I (DPP-I), is a lysosomal exocysteine protease. In humans, it is encoded by the CTSC gene. Cathepsin C catalyzes excision of dipeptides from the N-terminus of protein. Cathepsin C is known to be an activator of elastases [Turk D. et al., The EMBO Journal (2001) 20 (23): 6570-6582].

CELA1 is a chymotrypsin-like elastase family, member 1. Its gene is located on chromosome 12, Location 12q13. It is expressed, for example, in the pancreas, stomach, intestine, kidney, lung, embryonic tissue, liver, muscle, joint, brain, mammary gland, spleen, blood, tongue, bone and bladder. CELA3A is a chymotrypsin-like elastase family, member 3A. Its gene is located on the first chromosome, Location 1p36.12. It is expressed, for example, in the pancreas, bladder, liver, prostate, skin, thymus, connective tissue, brain and blood.

Surprisingly, it has herein been shown that specific targeting of Cathepsin C, or CELA1 or CELA3, in particular CELA3A, or an enzyme structurally related thereto, in terms of defining of a compound or agent to downregulate expression or inhibit activity of same or both, resulting in prevention of necrosis, treatment of necrosis or a combination thereof. Surprisingly, novel agents and novel compounds have herein been described which are useful in the compositions and uses/methods of this invention.

Also surprisingly, a class of agents and compounds have herein been defined, which may downregulate expression or inhibit activity of same or both, resulting in prevention of necrosis, treatment of necrosis or a combination thereof, whereby the compounds existence may be previously known, but therapeutic use of same was not described.

Also surprisingly, a class of agents and compounds have herein been defined, which may downregulate expression or inhibit activity of same or both, resulting in prevention of necrosis, treatment of necrosis or a combination thereof, whereby the compounds existence may be previously known or therapeutic use per se may have been previously known, but specific use of same in the prevention, abrogation, reduction of incidence or treatment of cell or tissue necrosis or diseases related thereto was not known.

The principles and operation of the present invention may be better understood with reference to the drawings and accompanying descriptions.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

Myocardial infarction, brain injury, brain stroke, liver cirrhosis and many other diseases and conditions are associated with a necrotic form of cell death.

While reducing the present invention to practice, the present inventors have uncovered that Cathepsin C, CELA1 and particularly CELA3A or a structurally related enzyme or enzymes thereto are cellular targets which modulate necrotic cellular responses and specifically that down regulation or inhibition of same can be used for protecting cells from necrosis-induced cell death.

Figure 2:
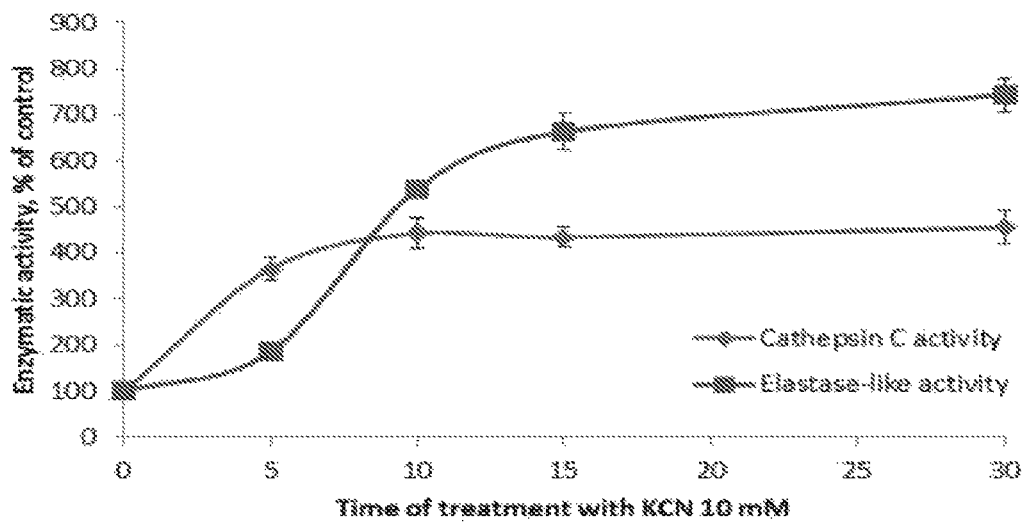
FIG. 2 is a line graph depicting the induction of proteolytic activity by 10 mM KCN treatment as assessed by enzymatic assays. U-937 cells were treated with KCN for different time intervals. The Cathepsin C and elastase like activities in the cell lysates were measured using specific substrates (as depicted in detail in the Examples section herein below).
Figure 3:
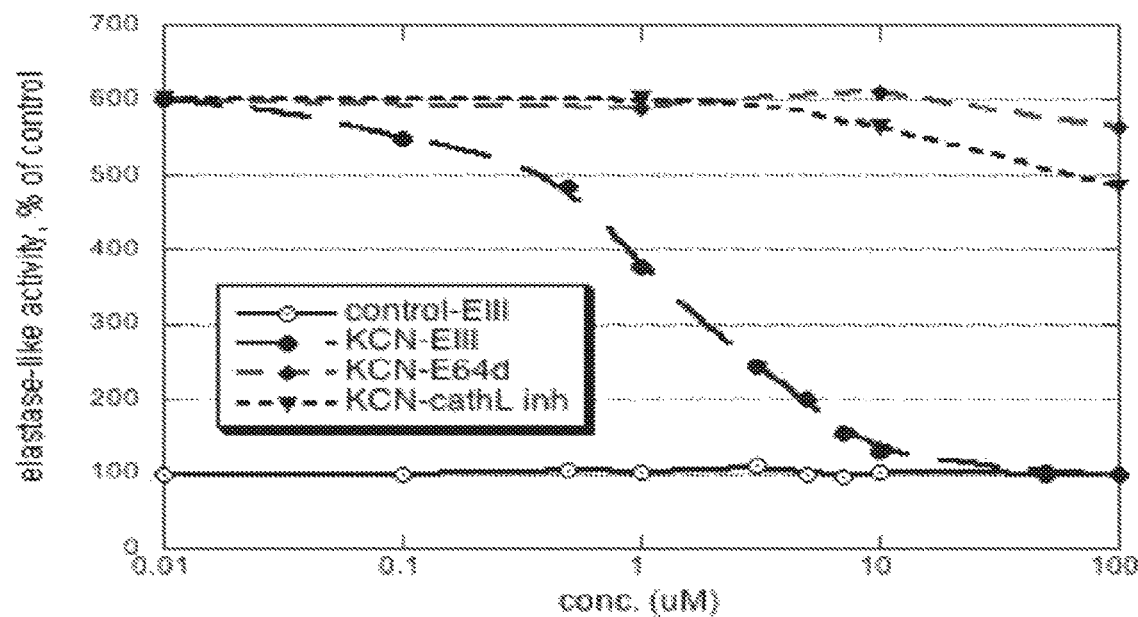
FIG. 3 illustrates a dose dependent inhibition of KCN induced elastase-like activity in cell by elastase inhibitor III. Cell lysates were prepared following treatment with 10 mM KCN for 30 min. Elastase-like activity was measured using the substrate MAAPV. Cathepsin L inhibitor and E-64d had no effect on elastase-like proteolytic activity. Data not shown.

As is shown herein below and in the Examples section which follows, the present inventors have uncovered that cell necrosis induces activation of intracellular elastases (see FIGS. 2A-B and 3). Furthermore, RNA silencing agents which specifically downregulate the expression of at least one of intracellular CELA3A, CELA1, and/or Cathepsin C prevent necrotic form of cell death (see FIGS. 4A-B). Moreover, inhibition of these targets by specific siRNAs (SEQ ID NOs: 1-3, respectively) resulted in inhibition of Cathepsin C enzymatic activity or CELA1/CELA3A elastase-like activity in the target cells in a specific manner (see FIGS. 5A-B). Moreover, the ability of elastase inhibitors to prevent brain cells necrotic damage in-vivo was shown using the closed head injury (trauma) model in mice and rats (see FIGS. 8A-B), APAP-induced liver toxicity model in mice (FIG. 9) and in myocardial ischemia/reperfusion model in mice (FIG. 10). Taken together, these results substantiate the use of downregulating agents or inhibitors for at least one of intracellular CELA3A or structurally related enzyme, CELA1, and/or Cathepsin C for the treatment or prevention of necrosis induced cell death. Moreover, the identification of CELA3A or structurally related enzyme and optionally CELA1, as primary targets of the necrotic process allows the design of specific elastase inhibitors which do not interfere with the enzymatic activity of other elastases.

Thus, according to one aspect of the present invention, there is provided a method of preventing or inhibiting necrosis of a cell, the method comprising administering to a cell that is subjected to a necrotic signal a therapeutically effective amount of an agent which specifically downregulates an expression and alternatively or additionally inhibits an activity of a at least one of intracellular CELA3A or structurally related enzyme, CELA1, and/or Cathepsin C.

The phrase "necrosis" as used herein refers to the premature death of a cell in a living tissue. Necrosis is a pathological process which is typically characterized by cell membrane and organelle disruption, cell swelling, mitochondria impairment, followed by cell lyses and ultimately cell death. Also, cell lysis is typically accompanied by an inflammatory response and inflammation may increase necrosis.

Necrosis induced cell death can be assayed by any method known to one of ordinary skill in the art, including for example, by CytoTox 96® Non-Radioactive Cytotoxicity Assay (Promega, WI, USA), by LDH Cytotoxicity Assay Kit (Cayman, MI, USA,) Staining by acridine orange/ethidium bromide and analyzing by fluorescence microscopy or by FACS (using e.g. the vital dye HO342), see further details in the Examples section herein below.

According to some embodiments of the invention, necrosis can be associated with a variety of medical conditions/diseases, each of which is a therapeutic target contemplated according to some embodiments of the present invention. Examples of such medical conditions/diseases include, but not limited to, an infection, a toxin, a poison, a radiation, a physical trauma, an inflammation, a lack of nutrient or oxygen supply, a chemical imbalance, an interruption of blood supply, other conditions leading to cell or tissue death, or a combination of two or more of the above. In a specific embodiment, tissue necrosis can be associated with transplantation and/or poor preservation of the tissue during transplantation. For example, cell or tissue necrosis can be associated with any one or more of the following conditions: an abscess, ague, anemia, ankylosis, anoxia, apnea, arthritis, asphyxiation, asthma, ataxia, atrophy, backache, bleeding, blennorhea, cachexia, caries, colic, constipation, convulsion, coughing, cyanosis, diarrhea, dizziness, dropsy, dry gangrene, dysentery, dyspepsia, dyspnea, edema, emaciation, fainting, fatigue, fever, fibrillation, gas gangrene, genetic diseases, high blood pressure, hydrops, hypertension, hypotension, icterus, indigestion, inflammation, insomnia, itching, jaundice, low blood pressure, lumbago, marasmus, moist gangrene, noma, pain, paralysis, pruritus, rash, rheum, sclerosis, seizure, shock, skin eruption, sore, spasm, sphacelation, tabes, tachycardia, tooth decay, tumor, upset stomach, vertigo or vomiting.

It will be appreciated that necrosis can be localized to a group of living cells or can be spread over one or more tissue areas (e.g. necrotic tissue).

The term "tissue" refers to part of an organism consisting of cells designed to perform a function or functions. Typically a solid tissue is vascularized. Examples include, but are not limited to, brain tissue, retina, skin tissue, hepatic tissue, pancreatic tissue, bone tissue, cartilage tissue, connective tissue, blood tissue, muscle tissue, cardiac tissue brain tissue, vascular tissue, renal tissue, pulmonary tissue, gonadal tissue, hematopoietic tissue.

Typically, a cell undergoes necrosis after receiving a necrotic signal from its extracellular environment but not exclusively. Any of the conditions mentioned above, e.g. lack of oxygen, poison, toxin, etc., and may initiate the process leading to necrosis of a cell.

The term "necrotic cell" or "necrotizing cell" as used herein encompasses any type of cell that has received a necrotic signal and exhibits at least one phenotype associated with necrosis (as described above).

A cell according to the present teachings may comprise, for example, a brain cell, a neuron, a cardiac cell, a muscle cell, a skin cell, a bone cell, a pancreatic cell, a liver cell, a kidney cell, an intestinal cell, a spleen cell, a respiratory cell, a lung cell, a lymphocyte or a monocyte or any affected cell as herein described.

As used herein, term "necrotic cell" further relates to a cell at any stage of necrosis. Thus, the cell may be at initial stages of necrosis (e.g. undergoing cell swelling or mitochondria impairment) or may be at the final stages of cell death (e.g. undergoing cell lysis).

As used herein the phrase "inhibiting" or "treating" refers to reducing, curing, reversing, attenuating, alleviating, minimizing, suppressing or halting the deleterious effects of necrosis.

In some aspects, when referring to the prevention of a disease associated with cell or tissue necrosis, such reference is with regard to reduction of incidence of the disease on a population level. In some aspects, such reference may be with regard to a patient suffering from a repeat or relapsing disease, where failure to develop full symptomatology, pathogenesis or severity of the disease as previously occurred in such patient, may serve as an indication of true prevention.

In some aspects, when referring to the prevention of necrosis on a cell or tissue level, same may refer to obvious reduction in classic markers or histopathologic evidence or secreted signals typically associated with necrosis.

According to one embodiment, treating or inhibiting necrosis of a cell or tissue may reduced necrosis by at least about 10%, by at least about 20%, by at least about 30%, by at least about 40%, by at least about 50%, by at least about 60%, by at least about 70%, by at least about 80%, by at least about 90% or by at least about 100%, as compared to a control necrotic cell/tissue of the same type which has not been treated with the agents of the present invention but otherwise has been subjected to the same necrotic signals as the treated cells/tissues.

As mentioned hereinabove, the method of this aspect of the present invention is affected by administering to a cell that is subjected to a necrotic signal an agent which specifically downregulates an expression and alternatively or additionally inhibits an activity of at least one of intracellular CELA3A, or a structurally related enzyme, CELA1, and/or Cathepsin C.

As used herein "specifically" refers to downregulating an expression and/or inhibiting an activity of at least one of intracellular CELA3A or a structurally similar enzyme, CELA1, and/or Cathepsin C but not substantially interfering with the activity or expression of any other protein in the cell (i.e. less than 10%, 15%, 20%, 25%, 30% reduction in activity or expression of cellular components that are not at least one of intracellular CELA3A, CELA1, and/or Cathepsin C). By specifically the present teachings, also refer to the ability of a single agent to downregulate an expression and/or inhibit an activity of at least one of intracellular CELA3A, CELA1 and/or Cathepsin C, two of them (e.g., CELA3A and CELA1 C) or all of them.

As used herein "downregulating" or "inhibiting" can be interchangeably used to refer to decreasing, reducing, attenuating, alleviating, minimizing, suppressing or halting the expression or activity of at least one of intracellular Cathepsin C, CELA1, CELA3A or a structurally related enzyme thereto protein. According to one embodiment, downregulating an expression and/or inhibiting an activity of at least one of intracellular Cathepsin C, CELA1, CELA3A or a structurally related enzyme thereto protein is by at least about 5%, by at least about 10%, by at least about 20%, by at least about 30%, by at least about 40%, by at least about 50%, by at least about 60%, by at least about 70%, by at least about 80%, by at least about 90% or by at least about 100%, as compared to a control at least one of intracellular CELA3A, CELA1, and/or Cathepsin C proteins which have not been treated with the agents of the present invention but otherwise have been subjected to the same conditions.

As used herein the term "expression" refers to protein expression or mRNA expression.

As used herein the phrase "activity of at least one of intracellular Cathepsin C, CELA1, CELA3A or a structurally related enzyme thereto" refers to a biological activity e.g., enzymatic activity thereof. According to one embodiment, the activity of CELA3A and/or CELA1 refers to the serine protease activity thereof (e.g. elastase activity of hydrolyzing proteins such as elastin). According to another embodiment, the activity of Cathepsin C refers to the lysosomal cysteine proteinase activity thereof (e.g. in activation of serine proteinases).

Evaluating the level of Cathepsin C, CELA1, CELA3A or a structurally related enzyme thereto expression or activity (e.g. downregulation thereof) can be carried out by any method known to one of ordinary skill in the art. Thus, for example, determine the protein level of at least one of intracellular Cathepsin C, CELA1, CELA3A or a structurally related enzyme thereto can be carried out, for example, using enzyme-linked immunosorbant (ELISA) assays, immunofluorescent (IF) assays or Chemiluminescent Immunoassay (CLIA) assays, available e.g. from Uscn, OnGene or Sigma-Aldrich. It could be combined with enzymatic assay. mRNA expression levels can be carried out using e.g. Northern blot analysis or RT-qPCR. CELA1 and/or CELA3A activity assays which may be used in accordance with the present teachings include e.g. Ellman Esterase Assay (see Ellman, G. L., et al, Biochem. Pharmacol. 7, 88-95, 1961) or esterase activity assay by flow injection analysis (FIA) [see Joga et al., Biotechnology Letters (2201) 23(12): 943-948]. Cathepsin C activity assays which may be used in accordance with the present teachings include CTSC Assay Kits available e.g. from Uscn Life Science Inc.

Thus, for example, and as described in further detail in Example 3 herein below, elastase-like activity may be measured by ELISA with N-methoxysuccinyl-Ala-Ala-Pro-Val p-nitroanilide (MAAPV) used as substrate (Sigma), while Cathepsin C like activity may be measured by ELISA with Gly-Phe p-nitroanilide used as substrate (Sigma).

As used herein, the term "Cathepsin C" relates to the lysosomal exocysteine protease belonging to the peptidase C1 family, also named dipeptidyl peptidase I (DPP-I) or Cathepsin C (CTSC), e.g. as set forth in NP_001107645.1 (SEQ ID NO: 6).

As used herein, the term "CELA1" relates to the enzyme chymotrypsin-like elastase family member 1 (CELA1), also known as elastase-1 (ELA1), e.g. as set forth in NP_001962.3 (SEQ ID NO: 8).

As used herein, the term "CELA3A" relates to the enzyme chymotrypsin-like elastase family member 3A, also known as elastase family member 3A, e.g. as set forth in NP_005738.4 (SEQ ID NO: 10).

Downregulation of Cathepsin C, CELA1 and CELA3A expression can be effected on the genomic and/or the transcript level using a variety of molecules which interfere with transcription and/or translation [e.g., RNA silencing agents (e.g., antisense, siRNA, shRNA, micro-RNA), Ribozyme and DNAzyme]. Inhibition of at least one of intracellular CELA3A, CELA1, and/or Cathepsin C activity can be effected on the protein level i.e., inhibiting activity of the protein or cause its degradation using e.g., antibodies, antagonists, enzymes that cleave the polypeptide, small molecules, natural inhibitors and the like.

According to one embodiment, the agent capable of inhibiting at least one of intracellular CELA3A, CELA1, and/or Cathepsin C is a high affinity binding molecule which binds to at least one domain composed of folded amino acid sequence of Cathepsin C, CELA3A and CELA1.

For example, the high affinity binding molecule may be an aptamer, an antibody or antibody fragment capable of specifically binding Cathepsin C, CELA3A and CELA1. According to a specific embodiment, the high affinity molecule comprises an antigen recognition domain e.g., an antibody that specifically binds at least one epitope of a Cathepsin C, CELA3A and CELA1. As used herein, the term "epitope" refers to any antigenic determinant on an antigen to which the paratope of an antibody binds.

Epitopic determinants usually consist of chemically active surface groupings of molecules such as amino acids or carbohydrate side chains and usually have specific three dimensional structural characteristics, as well as specific charge characteristics.

Exemplary epitopes of CELA1 and CELA3A which may be targeted in accordance with the present teachings comprise the amino acid sequences as set forth in SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22 and SEQ ID NO: 23. These exemplary amino acid sequences are contemplated as epitope regions of CELA1 and CELA3A which can be targeted for downregulation of same. It will be appreciated that further qualification for antibody specificity and enzyme inhibition need to be carried out for each of the antibodies generated using methods well known in the art e.g. ELISA or Western Blot assays.

The term "antibody" as used in this invention includes intact molecules as well as functional fragments thereof, such as Fab, F(ab')2, and Fv that are capable of binding to macrophages. These functional antibody fragments are defined as follows: (1) Fab, the fragment which contains a monovalent antigen-binding fragment of an antibody molecule, can be produced by digestion of whole antibody with the enzyme papain to yield an intact light chain and a portion of one heavy chain; (2) Fab', the fragment of an antibody molecule that can be obtained by treating whole antibody with pepsin, followed by reduction, to yield an intact light chain and a portion of the heavy chain; two Fab' fragments are obtained per antibody molecule; (3) (Fab')2, the fragment of the antibody that can be obtained by treating whole antibody with the enzyme pepsin without subsequent reduction; F(ab')2 is a dimer of two Fab' fragments held together by two disulfide bonds; (4) Fv, defined as a genetically engineered fragment containing the variable region of the light chain and the variable region of the heavy chain expressed as two chains; and (5) Single chain antibody ("SCA"), a genetically engineered molecule containing the variable region of the light chain and the variable region of the heavy chain, linked by a suitable polypeptide linker as a genetically fused single chain molecule.

Methods of producing polyclonal and monoclonal antibodies as well as fragments thereof are well known in the art (See for example, Harlow and Lane, Antibodies: A Laboratory Manual, Cold Spring Harbor Laboratory, New York, 1988, incorporated herein by reference).

Antibody fragments according to some embodiments of the invention can be prepared by proteolytic hydrolysis of the antibody or by expression in E. coli or mammalian cells (e.g. Chinese hamster ovary cell culture or other protein expression systems) of DNA encoding the fragment. Antibody fragments can be obtained by pepsin or papain digestion of whole antibodies by conventional methods. For example, antibody fragments can be produced by enzymatic cleavage of antibodies with pepsin to provide a 5S fragment denoted F(ab')2. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly. These methods are described, for example, by Goldenberg, U.S. Pat. Nos. 4,036,945 and 4,331,647, and references contained therein, which patents are hereby incorporated by reference in their entirety. See also Porter, R. R. [Biochem. J. 73: 119-126 (1959)]. Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

Fv fragments comprise an association of VH and VL chains. This association may be noncovalent, as described in Inbar et al. [Proc. Nat'l Acad. Sci. USA 69:2659-62 (19720]. Alternatively, the variable chains can be linked by an intermolecular disulfide bond or cross-linked by chemicals such as glutaraldehyde. Preferably, the Fv fragments comprise VH and VL chains connected by a peptide linker. These single-chain antigen binding proteins (sFv) are prepared by constructing a structural gene comprising DNA sequences encoding the VH and VL domains connected by an oligonucleotide. The structural gene is inserted into an expression vector, which is subsequently introduced into a host cell such as E. coli. The recombinant host cells synthesize a single polypeptide chain with a linker peptide bridging the two V domains. Methods for producing sFvs are described, for example, by [Whitlow and Filpula, Methods 2: 97-105 (1991); Bird et al., Science 242:423-426 (1988); Pack et al., Bio/Technology 11:1271-77 (1993); and U.S. Pat. No. 4,946,778, which is hereby incorporated by reference in its entirety.

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See, for example, Larrick and Fry [Methods, 2: 106-10 (1991)].

Humanized forms of non-human (e.g., murine) antibodies are chimeric molecules of immunoglobulins, immunoglobulin chains or fragments thereof (such as Fv, Fab, Fab', F(ab').sub.2 or other antigen-binding subsequences of antibodies) which contain minimal sequence derived from non-human immunoglobulin. Humanized antibodies include human immunoglobulins (recipient antibody) in which residues form a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., Nature, 321:522-525 (1986); Riechmann et al., Nature, 332:323-329 (1988); and Presta, Curr. Op. Struct. Biol., 2:593-596 (1992)].

Methods for humanizing non-human antibodies are well known in the art. Generally, a humanized antibody has one or more amino acid residues introduced into it from a source which is non-human. These non-human amino acid residues are often referred to as import residues, which are typically taken from an import variable domain. Humanization can be essentially performed following the method of Winter and co-workers [Jones et al., Nature, 321:522-525 (1986); Riechmann et al., Nature 332:323-327 (1988); Verhoeyen et al., Science, 239:1534-1536 (1988)], by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries [Hoogenboom and Winter, J. Mol. Biol., 227:381 (1991); Marks et al., J. Mol. Biol., 222:581 (1991)]. The techniques of Cole et al. and Boerner et al. are also available for the preparation of human monoclonal antibodies (Cole et al., Monoclonal Antibodies and Cancer Therapy, Alan R. Liss, p. 77 (1985) and Boerner et al., J. Immunol., 147(1):86-95 (1991)]. Similarly, human antibodies can be made by introduction of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al., Bio/Technology 10: 779-783 (1992); Lonberg et al., Nature 368: 856-859 (1994); Morrison, Nature 368 812-13 (1994); Fishwild et al., Nature Biotechnology 14, 845-51 (1996); Neuberger, Nature Biotechnology 14: 826 (1996); and Lonberg and Huszar, Intern. Rev. Immunol. 13, 65-93 (1995).

Thus, inhibition of at least one of intracellular CELA3A, CELA1, and/or Cathepsin C enzymatic activity may be affected using an antibody which specifically binds the active enzyme by recognition of, for example, a conformational change of the enzyme. Alternatively, the antibody may inhibit enzymatic activity by binding to the enzyme's substrate.

According to one embodiment of the present invention, there is provided an antibody which binds with a minimal affinity of Kd $10^{-7}$ M or lower to CELA3A and CELA1 but binds to CELA2A or CELA3B with a minimal affinity of at least 10 times lower (e.g., $10^{-6}$ M). According to a specific embodiment, the antibody binds the target with a Kd in the range of ($10^{-8}$-$10^{-10}$ M or $10^{-9}$-$10^{-10}$ M).

According to one embodiment of the present invention, there is provided an antibody which binds with a minimal affinity of Kd $10^{-7}$ M or lower to Cathepsin C but binds to Cathepsins A, B, D, E, G, H, K, L1, L2, O, S, W or Z with a minimal affinity at least 10 times lower (e.g., $10^{-6}$ M). According to a specific embodiment, the antibody binds the target with a Kd in the range of ($10^{-8}$-$10^{-10}$ M or $10^{-9}$-$10^{-10}$ M).

Exemplary antibodies which may be used in accordance with the present teachings include, but are not limited to, anti-CELA1 antibodies available e.g. from EMD Millipore, Sigma-Aldrich and Santa Cruz Biotechnology; anti-CELA3A antibodies available e.g. from Abcam, Sigma-Aldrich and Santa Cruz Biotechnology; anti-Cathepsin C/CTSC antibodies available e.g. from Sigma-Aldrich and R&D Systems. Such antibodies can be qualified for their specificity as further described hereinunder.

Another agent capable of inhibiting Cathepsin C, CELA1, CELA3A or a structurally related enzyme thereto would be any molecule which binds to and/or cleaves Cathepsin C, CELA1, CELA3A or a structurally related enzyme thereto. Such molecules can be Cathepsin C, CELA1, CELA3A or a structurally related enzyme thereto antagonists, or Cathepsin C, CELA1, CELA3A or a structurally related enzyme thereto inhibitory peptide.

It will be appreciated that anon-functional analogue of at least a catalytic or binding portion of Cathepsin C, CELA1, CELA3A or a structurally related enzyme thereto can be also used as an agent, which inhibits Cathepsin C, CELA1, CELA3A or a structurally related enzyme thereto.

Another agent which can be used along with some embodiments of the invention to inhibit Cathepsin C, CELA1, CELA3A or a structurally related enzyme thereto is a molecule which prevents Cathepsin C, CELA1, CELA3A or a structurally related enzyme thereto activation or substrate binding.

Another agent which can be used along with some embodiments of the invention to inhibit Cathepsin C, CELA1, CELA3A or a structurally related enzyme thereto is a dominant negative molecule i.e. a part of the peptide or a mutation thereof that competes with effectors of Cathepsin C, CELA1, CELA3A or a structurally related enzyme thereto.

Another agent which can be used along with some embodiments of the invention to inhibit at least one of intracellular Cathepsin C, CELA1, CELA3A or a structurally related enzyme thereto is a natural inhibitor in their activation pathway/s. Exemplary natural inhibitors of Cathepsin C which may be used in accordance with the present teachings include, but are not limited to, Cystatin F, Human proteinase inhibitor 9 (PI-9/serpinB9), Cystatin C and Stefins A and B.

Thus, any specific inhibitor which may penetrate or may be modified to penetrate (as discussed in further details below) the cell membrane and specifically inhibit at least one of intracellular Cathepsin C, CELA1, CELA3A or a structurally related enzyme thereto catalytic activity may be used in accordance with the present teachings. In particularly preferred embodiments, the invention is directed to the use of a small molecule that inhibits specifically at least one of intracellular CELA3A or structurally similar enzyme CELA1, and/or Cathepsin C. According to an aspect of some embodiments of the present invention the small molecule binds with a minimal affinity of Kd $10^{-7}$ M and lower to specifically at least one of intracellular CELA3A, CELA1, and/or Cathepsin C, and binds to CELA2A or CELA3B or to Cathepsins A, B, D, E, G, H, K, L1, L2, O, S, W or Z with a minimal affinity of at least 10 times higher Kd.

In other aspects, the invention contemplates the use of specific elastase inhibitors, such elastase inhibitors II (MeO-Suc-AAPA-CMK) available e.g. from Calbiochem-Novabiochem, USA.

An exemplary elastase inhibitor which may be used in accordance with the present invention includes also non-peptide small molecules.

In some aspects, such elastase inhibitors may also represent compounds/agents of this invention which downregulate expression and/or inhibit the activity of CELA1, CELA3 and in particular CELA3A and/or Cathepsin C. In some aspects, such small-molecule CELA3 or structurally related inhibitors may be designed specifically against CELA3A, based on 3D structure similarities and topological analogs. Some small molecules may belong to various chemical families. Exemplary compounds that may inhibit selectively and specifically CELA 3A or structurally similar enzyme include those recited in Table 1 herein.

The invention will also be understood to encompass any subgrouping of the agents recited in Table 1 below, or a derivative, isomer, salt, oxide, polymorph or other known form of same.

The agents capable of inhibiting necrosis include among others small inhibitory compounds that belong to various chemical families, for example 2-aminoimidazolines, 2-aminothiazoles and isoxazoles.

In some embodiments the agents are any compound described by Table I below, or in some embodiments, the agent is a derivative, analogue, or pharmaceutical salt, or isomer of same.

In some embodiments, any combination or sub-grouping of the agents described in Table 1 is contemplated as part of this invention and represents an embodiment thereof.

TABLE 1

Embodied compounds and compounds for use of the invention:

| Structure | Ref #: | Chemical Name |
|---|---|---|
| 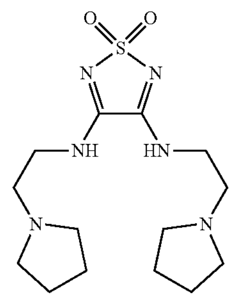 [SMILES: O=S1(=O)N=C(NCCN2CCCC2)C(NCCN2CCCC2)=N1] | (Z087-0195) | 3,4-bis((2-(pyrrolidin-1-yl)ethyl)amino)-1,2,5-thiadiazole 1,1-dioxide |
| 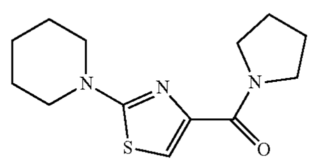 [SMILES: O=C(c1csc(N2CCCCC2)n1)N1CCCC1] | (Z601-4253) | (2-(piperidin-1-yl)thiazol-4-yl)(pyrrolidin-1-yl)methanone |
| 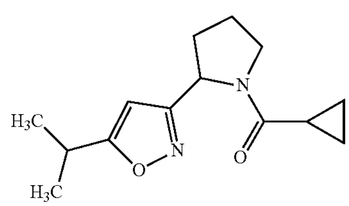 [SMILES: CC(C)c1cc(C2CCCN2C(=O)C2CC2)no1] | Z632-2266 | cyclopropyl(2-(5-isopropylisoxazol-3-yl)pyrrolidin-1-yl)methanone; |
| 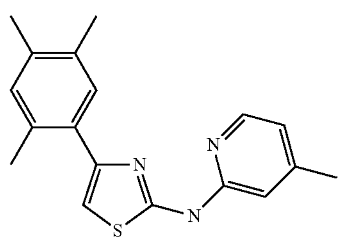 [SMILES: Cc1ccnc(Nc2nc(-c3cc(C)c(C)cc3C)cs2)c1] | M008-0111 | N-(4-methylpyridin-2-yl)-4-(2,4,5-trimethylphenyl)thiazol-2-amine |
| 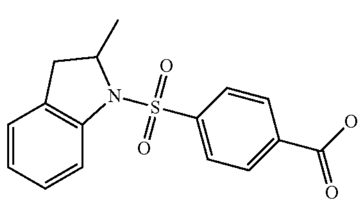 [SMILES: CC1Cc2ccccc2N1S(=O)(=O)c1ccc(C(=O)O)cc1] | D216-0746 | 4-((2-methylindolin-1-yl)sulfonyl)benzoic acid; |
| 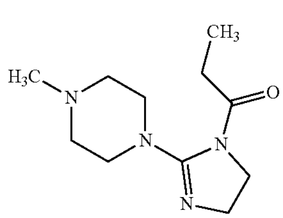 [SMILES: CCC(=O)N1CCN=C1N1CCN(C)CC1] | M059-0891 | 1-(2-(4-methylpiperazin-1-yl)-4,5-dihydro-1H-imidazol-1-yl)propan-1- |

TABLE 1-continued

Embodied compounds and compounds for use of the invention:

| Structure | Ref #: | Chemical Name |
|---|---|---|
| 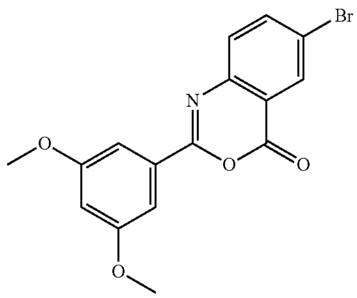 [SMILES: COc1cc(OC)cc(-c2nc3ccc(Br)cc3c(=O)o2)c1] | 3952-1000 | 6-bromo-2-(3,5-dimethoxyphenyl)-4 benzo[d][1,3]oxazin-4-one |
| 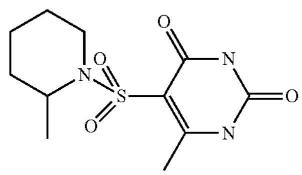 [SMILES: Cc1[nH]c(=O)[nH]c(=O)c1S(=O)(=O)N1CCCCC1C] | E214-0380 | 6-methyl-5-((2-methylpiperidin-1-yl)sulfonyl)pyrimidine-2,4(1H,3H)-dione; |
| 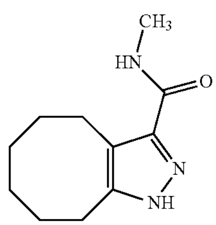 | Z632-6109 | N-methyl-4,5,6,7,8,9-hexahydro-1H-cycloocta[c]pyrazole-3-carboxamide |
| 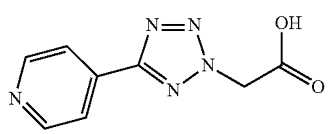 [SMILES: O=C(O)Cn1nnc(-c2ccncc2)n1] | 8018-2960 | 2-(5-(pyridin-4-yl)-2H-tetrazol-2-yl)acetic acid; |
| 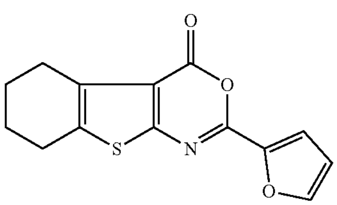 [SMILES: O=c1oc(-c2ccco2)nc2sc3c(c12)CCCC3] | 4789-3852 | 2-(furan-2-yl)-5,6,7,8-tetrahydro-4H-benzo[4,5]thieno[2,3-d][1,3]oxazin-4-one; |
| 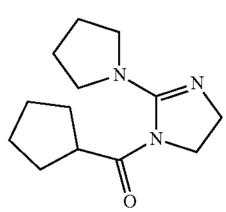 [SMILES: O=C(C1CCCC1)N1CCN=C1N1CCCC1] | M059-0082 | cyclopentyl(2-(pyrrolidin-1-yl)-4,5-dihydro-1H-imidazol-1-yl)methanon |
| 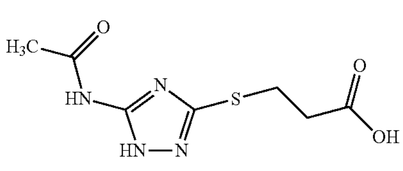 | L150-1122 | 3-((5-acetamido-1H-1,2,4-triazol-3-yl)thio)propanoic acid; |

TABLE 1-continued

Embodied compounds and compounds for use of the invention:

| Structure | Ref #: | Chemical Name |
|---|---|---|
| 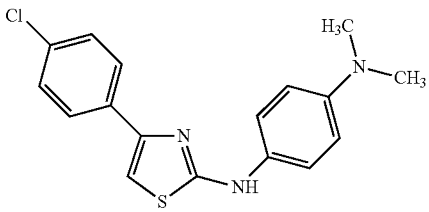 [SMILES: CN(C)c1ccc(Nc2nc(-c3ccc(Cl)cc3)cs2)cc1] | 4112-3656 | N1-(4-(4-chlorophenyl)thiazol-2-yl)-N4,N4-dimethylbenzene-1,4-diamine |
| 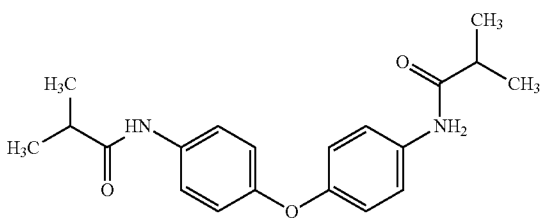 [SMILES: CC(C)C(=O)Nc1ccc(Oc2ccc(NC(=O)C(C)C)cc2)cc1] | Y200-4083 | N,N'-(oxybis(4,1-phenylene))bis(2-methylpropanamide); |
| 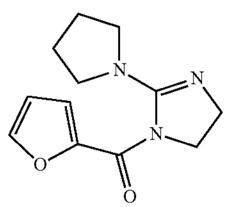 [SMILES: O=C(c1ccco1)N1CCN=C1N1CCCC1] | M059-0032 | furan-2-yl(2-(pyrrolidin-1-yl)-4,5-dihydro-1H-imidazol-1-yl)methanon |
| 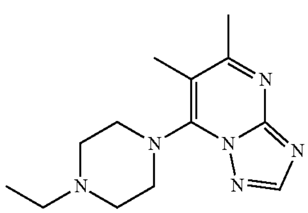 [SMILES: CCN1CCN(c2c(C)c(C)nc3ncnn23)CC1] | Z606-8336 | 7-(4-ethylpiperazin-1-yl)-5,6-dimethyl-[1,2,4]triazolo[1,5-a]pyrimidine; |
| 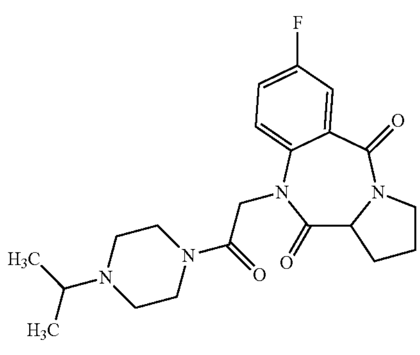 [SMILES: CC(C)N1CCN(C(=O)CN2C(=O)C3CCCN3C(=O)c3cc(F)ccc32)CC1] | M284-0488 | 7-fluoro-10-(2-(4-isopropylpiperazin-1-yl)-2-oxoethyl)-2,3-dihydro-1H-benzo[e]pyrrolo[1,2-a][1,4]diazepine-5,11(10H,11aH)-dione; |
| 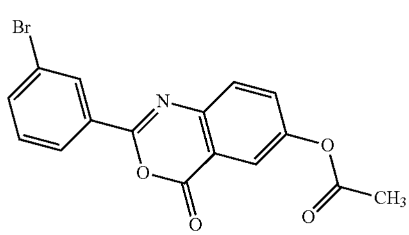 [SMILES: CC(=O)Oc1ccc2nc(-c3cccc(Br)c3)oc(=O)c2c1] | 4334-1600 | 2-(3-bromophenyl)-4-oxo-4H-benzo[d][1,3]oxazin-6-yl acetate |

TABLE 1-continued

Embodied compounds and compounds for use of the invention:

| Structure | Ref #: | Chemical Name |
| --- | --- | --- |
| 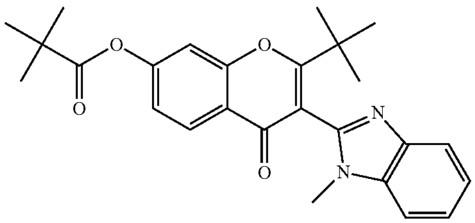 [SMILES: Cn1c(-c2c(C(C)(C)C)oc3cc(OC(=O)C(C)(C)C)ccc3c2=O)nc2ccccc21] | 4356-0595 | 2-(tert-butyl)-3-(1-methyl-1H-benzo[d]imidazol-2-yl)-4-oxo-4H-chromen-7-yl pivalate; |
| 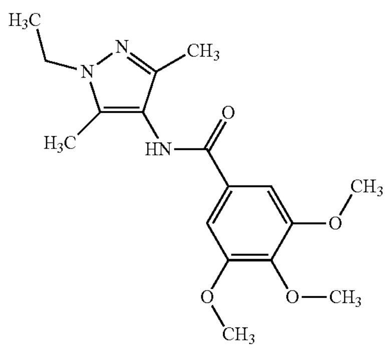 [SMILES: CCn1nc(C)c(NC(=O)c2cc(OC)c(OC)c(OC)c2)c1C] | Y200-4180 | N-(1-ethyl-3,5-dimethyl-1H-pyrazol-yl)-3,4,5-trimethoxybenzamide |
| 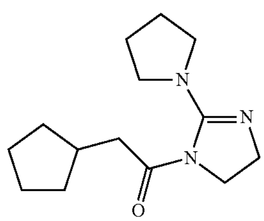 [SMILES: O=C(CC1CCCC1)N1CCN=C1N1CCCC1] | M059-0055 | 2-cyclopentyl-1-(2-(pyrrolidin-1-yl)-dihydro-1H-imidazol-1-yl)ethanone; |
| 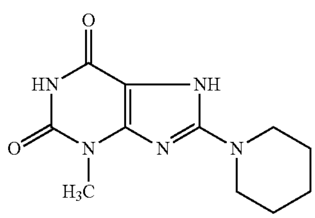 [SMILES: Cn1c(=O)[nH]c(=O)c2[nH]c(N3CCCCC3)nc21] | D226-0031 | 3-methyl-8-(piperidin-1-yl)-1H-purine-2,6(3H,7H)-dione; |
| 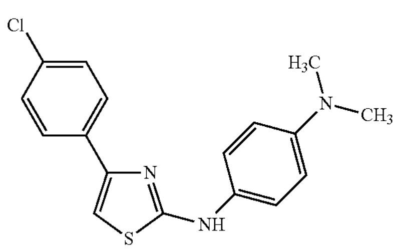 [SMILES: CN(C)c1ccc(Nc2nc(-c3ccc(Cl)cc3)cs2)cc1] | 4112-3656 | N1-(4-(4-chlorophenyl)thiazol-2-yl)-N4,N4-dimethylbenzene-1,4-diamine; |
| 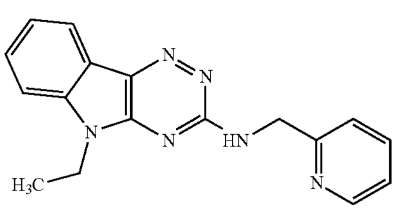 [SMILES: CCn1c2ccccc2c2nnc(NCc3ccccn3)nc21] | E205-0066 | 5-ethyl-N-(pyridin-2-ylmethyl)-5H-[1,2,4]triazino[5,6-b]indol-3-amine; |

TABLE 1-continued

Embodied compounds and compounds for use of the invention:

| Structure | Ref # | Chemical Name |
|---|---|---|
| 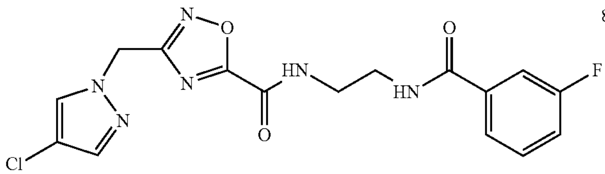 [SMILES: O=C(NCCNC(=O)c1nc(Cn2cc(Cl)cn2)no1)c1cccc(F)c1] | 8019-5381 | 3-((4-chloro-1H-pyrazol-1-yl)methyl)-N-(2-(3-fluorobenzamido)ethyl)-1,2,4-oxadiazole-5-carboxamide; |
| 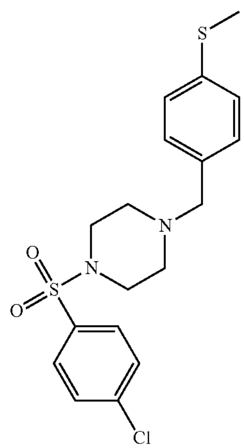 [SMILES: CSc1ccc(CN2CCN(S(=O)(=O)c3ccc(Cl)cc3)CC2)cc1] | 4240-0470 | 1-(4-(methylthio)benzyl)-4-tosylpiperazine |
| 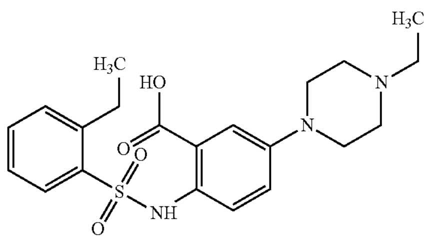 [SMILES: CCc1ccccc1S(=O)(=O)Nc1ccc(N2CCN(CC)CC2)cc1C(=O)O] | F684-0507 | 2-(2-ethylphenylsulfonamido)-5-(4-ethylpiperazin-1-yl)benzoic acid; |
| 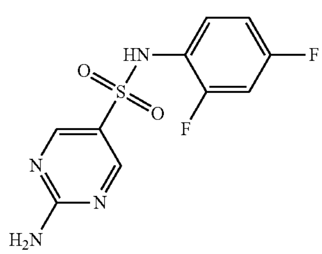 [SMILES: Nc1ncc(S(=O)(=O)Nc2ccc(F)cc2F)cn1] | G830-0845 | 2-amino-N-(2,4-difluorophenyl)pyrimidine-5-sulfonamide; |
| 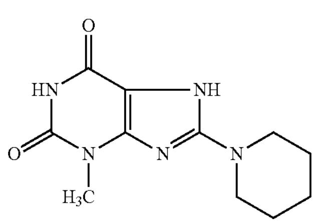 [SMILES: Cn1c(=O)[nH]c(=O)c2[nH]c(N3CCCCC3)nc21] | D226-0031 | 3-methyl-8-(piperidin-1-yl)-1H-purine-2,6(3H,7H)-dione; |
| 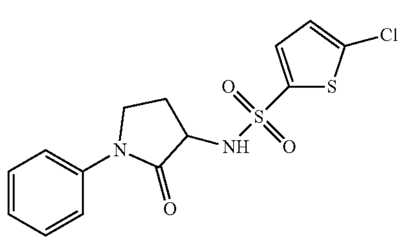 [SMILES: O=C1C(NS(=O)(=O)c2ccc(Cl)s2)CCN1c1ccccc1] | 5149-0030 | 5-chloro-N-(2-oxo-1-phenylpyrrolidin-3-yl)thiophene-2-sulfonamide; |

TABLE 1-continued

Embodied compounds and compounds for use of the invention:

| Structure | Ref #: | Chemical Name |
|---|---|---|
| 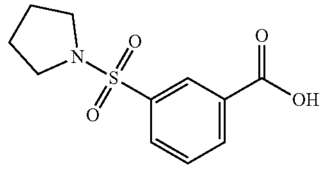 [SMILES: O=C(O)c1cccc(S(=O)(=O)N2CCCC2)c1] | 3506-0172 | 3-(pyrrolidin-1-ylsulfonyl)benzoic acid; |
| 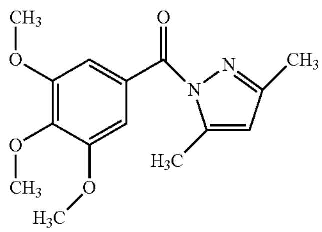 [SMILES: COc1cc(C(=O)n2nc(C)cc2C)cc(OC)c1OC] | 3346-3249 | (3,5-dimethyl-1H-pyrazol-1-yl)(3,4,5-trimethoxyphenyl)methanone; |
| 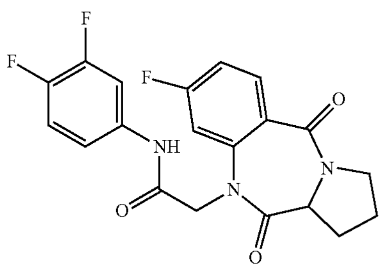 [SMILES: O=C(CN1C(=O)C2CCCN2C(=O)c2ccc(F)cc21)Nc1ccc(F)c(F)c1] | M284-0942 | N-(3,4-difluorophenyl)-2-(8-fluoro-5,11-dioxo-2,3,11,11a-tetrahydro-1H-benzo[e]pyrrolo[1,2-a][1,4]diazepin-10(5H)-yl)acetamide; |
| 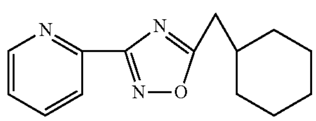 [SMILES: c1ccc(-c2noc(CC3CCCCC3)n2)nc1] | 4953-1443 | 5-(cyclohexylmethyl)-3-(pyridin-2-yl)-1,2,4-oxadiazole; |
| 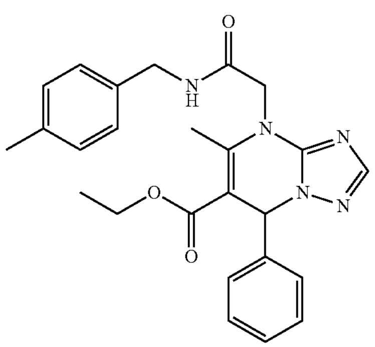 [SMILES: CCOC(=O)C1=C(C)N(CC(=O)NCc2ccc(C)cc2)c2ncnn2C1c1ccccc1] | D529-0049 | Ethyl5-methyl-4-(2-((4-methylbenzyl)amino)-2-oxoethyl)-7-phenyl-4,7-dihydro-[1,2,4]triazolo[1,5-a]pyrimidine-6-carboxylate; |
| 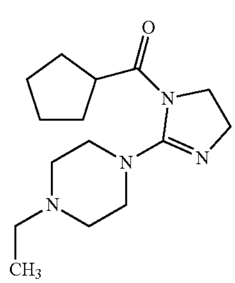 [SMILES: CCN1CCN(C2=NCCN2C(=O)C2CCCC2)CC1] | M059-1012 | cyclopentyl(2-(4-ethylpiperazin-1-yl)-4,5-dihydro-1H-imidazol-1-yl)methanone; |
| 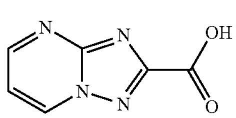 [SMILES: O=C(O)c1nc2ncccn2n1] | R052-2664 | [1,2,4]triazolo[1,5-a]pyrimidine-2-carboxylic acid; |

TABLE 1-continued

Embodied compounds and compounds for use of the invention:

| Structure | Ref #: | Chemical Name |
|---|---|---|
| 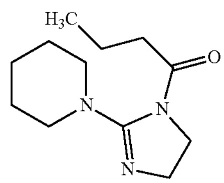 [SMILES: CCCC(=O)N1CCN=C1N1CCCCC1] | M059-0335 | 1-(2-(piperidin-1-yl)-4,5-dihydro-1H-imidazol-1-yl)butan-1-one; |
| 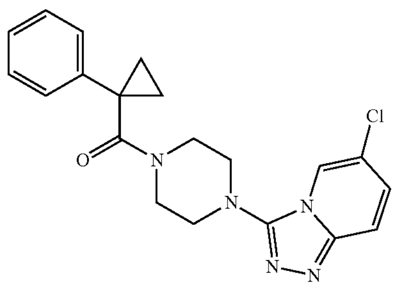 [SMILES: O=C(N1CCN(c2nnc3ccc(Cl)cn23)CC1)C1(c2ccccc2)CC1] | T404-2346 | (4-(6-chloro-[1,2,4]triazolo[4,3-a]pyridin-3-yl)piperazin-1-yl)(1-phenylcyclopropyl)methanone; |
| 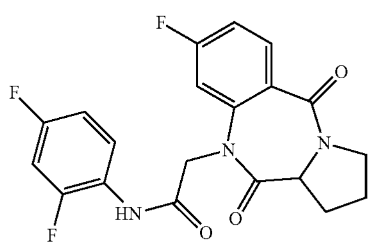 [SMILES: O=C(CN1C(=O)C2CCCN2C(=O)c2ccc(F)cc21)Nc1ccc(F)cc1F] | M284-0939 | N-(2,4-difluorophenyl)-2-(5,11-dioxo-2,3,11,11a-tetrahydro-1H-benzo[e]pyrrolo[1,2-a][1,4]diazepin-10(5H)-yl)acetamide; |
| 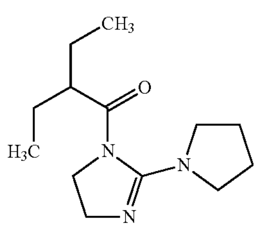 [SMILES: CCC(CC)C(=O)N1CCN=C1N1CCCC1] | M059-0053 | 2-ethyl-1-(2-(pyrrolidin-1-yl)-4,5-dihydro-1H-imidazol-1-yl)butan-1-one. |
| 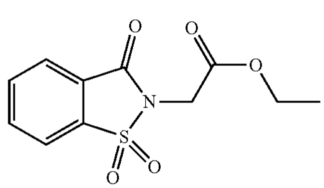 [SMILES: CCOC(=O)CN1C(=O)c2ccccc2S1(=O)=O] | 5149-0030 | Ethyl-2,3-dihydro-3-oxo-1,2-benzisothiazole-2-acetate-1,1-dioxide |
| 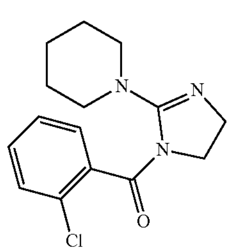 [SMILES: O=C(c1ccccc1Cl)N1CCN=C1N1CCCCC1] | M059-0326 | (2-chlorophenyl)-[2-(1-piperidyl)-4,5-dihydroimidazol-1-yl]methanone |

US 11,945,787 B2

TABLE 1-continued

Embodied compounds and compounds for use of the invention:

| Structure | Ref #: | Chemical Name |
|---|---|---|
| 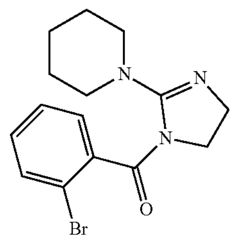 [SMILES: O=C(c1ccccc1Br)N1CCN=C1N1CCCCC1] | M059-0193 | (2-bromophenyl)-[2-(1-piperidyl)-4,5-dihydroimidazol-1-yl]methanone |

Exemplary compounds that may inhibit selectively and specifically CELA 1 include but not limited to N-[4-[4-(isobutyrylamino)phenoxy]phenyl]-2-methyl-propionamide, Ethyl-2,3-dihydro-3-oxo-1,2-benzisothiazole-2-acetate-1,1-dioxide.

In some embodiments, a compound of this invention and/or a composition of this invention may comprise and/or a method of this invention may provide for the use and/or a first medical use of this invention may include an agent characterized by the following formula:

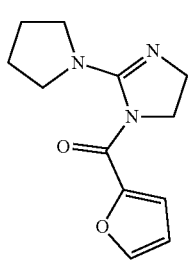

M059-0032

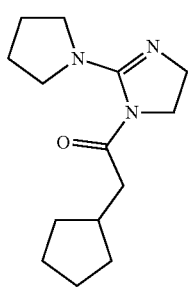

M059-0055

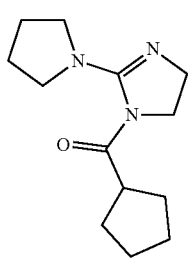

M059-0082

-continued

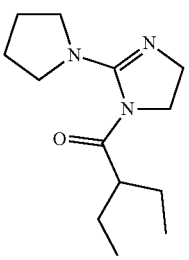

M059-0053

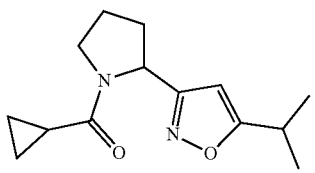

Z632-2266

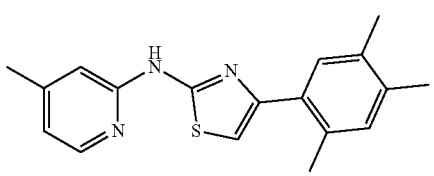

M008-0111

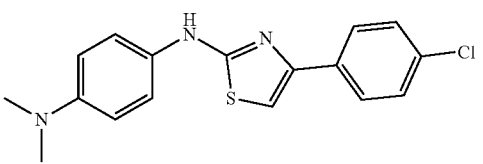

4112-3656

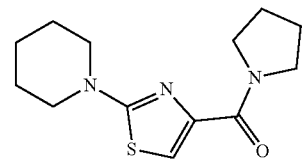

Z601-4253

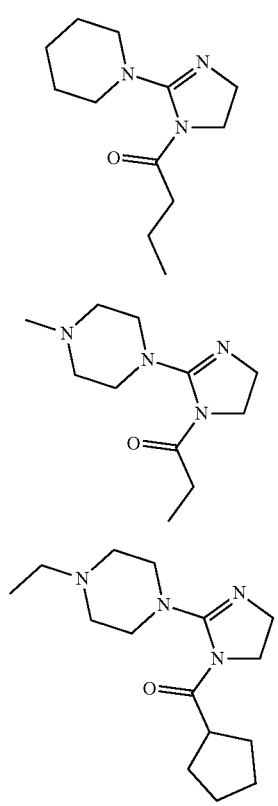

or any combination thereof. In some aspects, a compound of this invention and/or a composition of this invention may comprise and/or a method of this invention may provide for the use and/or a first medical use of this invention may include an agent characterized by the structure of M059-0032; M059-0055; M059-0082; M059-0053; M059-0335; M059-0891; M059-0891; M059-1012, M008-0111; 4112-3656; Z632-2266; or Z601-4253 or any subset of same. In some aspects, a compound of this invention and/or a composition of this invention may comprise and/or a method of this invention may provide for the use and/or a first medical use of this invention may include an agent characterized by the structure of M059-0032; M059-0055; M059-0082; M059-0053; M059-0335; M059-0891; M059-0891; M059-1012, or a compound with a similar structure where by the central 2-aminoimidazoline comprises substitution at the 2-amino position of any of same with a substituted or unsubstituted pyrrolidine, substituted or unsubstituted piperidine, substituted or unsubstituted piperazine, substituted or unsubstituted imidazolidine, substituted or unsubstituted pyrazolidine, substituted or unsubstituted aryl, substituted or unsubstituted 5 or 6 membered heterocyclic ring, or substituted or unsubstituted 5 or 6 membered cycloalkyl. In some aspects, a compound of this invention and/or a composition of this invention may comprise and/or a method of this invention may provide for the use and/or a first medical use of this invention may include an agent characterized by the structure of M059-0032; M059-0055; M059-0082; M059-0053; M059-0335; M059-0891; M059-0891; M059-1012, or a compound with a similar structure where by the central 2-aminoimidazoline comprises substitution at the 2-amino position of any of same with an unsubstituted pyrrolidine, an unsubstituted piperidine, an unsubstituted piperazine, an unsubstituted imidazolidine, an unsubstituted pyrazolidine, an unsubstituted aryl, an unsubstituted 5 or 6 membered heterocyclic ring, or an unsubstituted 5 or 6 membered cycloalkyl. In some aspects, a compound of this invention and/or a composition of this invention may comprise and/or a method of this invention may provide for the use and/or a first medical use of this invention may include an agent characterized by the structure of M059-0032; M059-0055; M059-0082; M059-0053; M059-0335; M059-0891; M059-0891; M059-1012, or a compound with a similar structure where by the central 2-aminoimidazoline comprises substitution at the 2-amino position of any of same with a substituted pyrrolidine, a substituted piperidine, a substituted piperazine, a substituted imidazolidine, a substituted pyrazolidine, a substituted aryl, a substituted 5 or 6 membered heterocyclic ring, a substituted 5 or 6 membered cycloalkyl. In some aspects, a compound of this invention and/or a composition of this invention may comprise and/or a method of this invention may provide for the use and/or a first medical use of this invention may include an agent characterized by the structure of M059-0032; M059-0055; M059-0082; M059-0053; M059-0335; M059-0891; M059-0891; M059-1012, or a compound with a similar structure where by the central 2-aminoimidazoline comprises substitution at the 2-amino position of any of same with substituted or unsubstituted pyrrolidine, substituted or unsubstituted piperidine, substituted or unsubstituted piperazine, substituted or unsubstituted imidazolidine, substituted or unsubstituted pyrazolidine.

In some aspects, a compound of this invention and/or a composition of this invention may comprise and/or a method of this invention may provide for the use and/or a first medical use of this invention may include an agent characterized by the structure of M008-0111; 4112-3656; or Z632-2266 or any subset of same.

In some aspects, a compound of this invention and/or a composition of this invention may comprise and/or a method of this invention may provide for the use and/or a first medical use of this invention may include an agent characterized by the structure of M008-0111; 4112-3656 or Z632-2266 or a compound with a similar structure where by the central 2-aminothiazoline comprises substitution at the 2-amino position with substituted or unsubstituted pyrrolidine, substituted or unsubstituted piperidine, substituted or unsubstituted piperazine, substituted or unsubstituted imidazolidine, substituted or unsubstituted pyrazolidine, substituted or unsubstituted aryl, substituted or unsubstituted 5 or 6 membered heterocyclic ring, or substituted or unsubstituted 5 or 6 membered cycloalkyl. In some aspects, a compound of this invention and/or a composition of this invention may comprise and/or a method of this invention may provide for the use and/or a first medical use of this invention may include an agent characterized by the structure of M008-0111; 4112-3656; or Z632-2266 or a compound with a similar structure where by the central 2-aminothiazoline or isoxazole comprises substitution at the 2-amino position with an unsubstituted pyrrolidine, an unsubstituted piperidine, an unsubstituted piperazine, an unsubstituted imidazolidine, an unsubstituted pyrazolidine, an unsubstituted aryl, an unsubstituted 5 or 6 membered heterocyclic ring, or an unsubstituted 5 or 6 membered cycloalkyl. In some aspects, a compound of this invention and/or a composition of this invention may comprise and/or a method of this invention may provide for the use and/or a first medical use of this invention may include an agent characterized by the structure of M008-0111; 4112-3656 or Z632-2266 or a compound with a similar structure where by the central 2-aminothiazoline comprises substitution at the 2-amino position with a substituted pyrrolidine, a substituted piperidine, a substituted piperazine, a substituted imidazolidine, a substituted pyrazolidine, a substituted aryl, a substituted 5 or 6 membered heterocyclic ring, a substituted 5 or 6 membered cycloalkyl.

In some aspects, a compound of this invention and/or a composition of this invention may comprise and/or a method of this invention may provide for the use and/or a first medical use of this invention may include an agent characterized by the structure of Formula I:

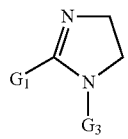

Formula I wherein G1 is substituted or unsubstituted pyrrolidine, substituted or unsubstituted piperidine, substituted or unsubstituted piperazine, substituted or unsubstituted imidazolidine, or substituted or unsubstituted pyrazolidine; and G3 is characterized by the following structure:

or G3 is substituted or unsubstituted alkyl, substituted or unsubstituted aryl or substituted or unsubstituted cyloalkyl;
wherein G2 is substituted or unsubstituted alkyl, substituted or unsubstituted aryl, substituted or unsubstituted cyloalkyl or substituted or unsubstituted heterocycle; or
a compound characterized by the structure of Formula II:

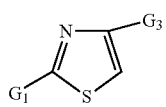

Formula II wherein G1 is substituted or unsubstituted pyrrolidine, substituted or unsubstituted pyridine, substituted or unsubstituted aryl, substituted or unsubstituted piperidine, substituted or unsubstituted piperazine, substituted or unsubstituted imidazolidine, or substituted or unsubstituted pyrazolidine; and
G3 is characterized by the following structure:

or G3 is substituted or unsubstituted alkyl, substituted or unsubstituted aryl or substituted or unsubstituted cyloalkyl;
wherein G2 is substituted or unsubstituted alkyl, substituted or unsubstituted aryl, substituted or unsubstituted cyloalkyl or substituted or unsubstituted heterocycle; or
a compound characterized by the structure of Formula III:

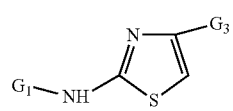

Formula III wherein G1 is substituted or unsubstituted pyrrolidine, substituted or unsubstituted pyridine, substituted or unsubstituted aryl, substituted or unsubstituted piperidine, substituted or unsubstituted piperazine, substituted or unsubstituted imidazolidine, or substituted or unsubstituted pyrazolidine; and
G3 is characterized by the following structure:

G2 or G3 is substituted or unsubstituted alkyl, substituted or unsubstituted aryl or substituted or unsubstituted cyloalkyl;
wherein G2 is substituted or unsubstituted alkyl, substituted or unsubstituted aryl, substituted or unsubstituted cyloalkyl or substituted or unsubstituted heterocycle In some aspects, the invention contemplates a compound of Formula I, II, III, IV, V or VI as herein described, or a composition comprising same, and including a first medical use of same, whereby the ring structure depicted in the formulae may further incorporate an additional heteroatom, for example, an additional Nitrogen or Oxygen.

When referring to the group:

it will be appreciated that the asterisks signify the point of attachment for the stated group. For example, when $G_3$ is characterized by the group

with regard to Formula I,

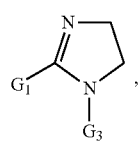

this in turn may be characterized by the following structure:

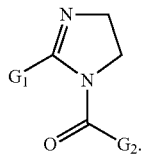

The skilled artisan will appreciate that the asterisk similarly indicates an attachment point at the indicated position for the appropriate corresponding structure in any of the compounds characterized by the Formulae I-VI, as described herein.

In some embodiments, with regard to G1, G2 or G3 being defined as pyrrolidine, pyridine, piperidine, piperazine, imidazolidine, pyrazolidine or a heterocycle, it should be understood that in some embodiments, the attachment point for such stated group to the indicated atom may be via the Nitrogen or heteroatom, or via a carbon atom of same group, as appropriate.

In some embodiments, with regard to compound of Formula I, when G1 is pyrrolidine, the point of attachment is via the nitrogen atom of the pyrrolidine group, and in some embodiments, when G1 is piperazine, the point of attachment is via the nitrogen atom of the piperazine group, and in some embodiments, when G1 is piperidine, the point of attachment is via the nitrogen atom of the piperadine group.

In some embodiments, with regard to the compound of Formula II, when G1 is piperidine, the point of attachment is via the nitrogen atom of the piperadine group and in some embodiments, when G1 is piperidine, the point of attachment is via a carbon atom of the piperidine group, where the Nitrogen atom is in an ortho position with respect to the point of attachment.

In some embodiments, this invention provides a compound characterized by the structure of Formula VI:

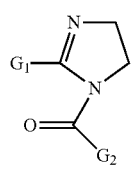

Formula VI

Wherein:
G1 is optionally substituted NH-pyrrolidine, optionally substituted NH-piperidine, optionally substituted NH-piperazine, optionally substituted NH-imidazolidine, optionally substituted NH-pyrazolidine, optionally substituted NH-aryl, optionally substituted NH-cycloalkyl, optionally substituted pyrrolidine, optionally substituted piperidine, optionally substituted piperidin, optionally substituted piperazine, optionally substituted imidazolidine, or optionally substituted pyrazolidine;
$G_2$ is optionally substituted alkyl, optionally substituted alkenyl, optionally substituted aryl, optionally substituted heteroaryl, optionally substituted cyloalkyl or optionally substituted heterocycle;
Wherein:
If $G_1$ is unsubstituted pyrrolidine, then $G_2$ is not alkyl, cyclopentyl, alkylcyclopentyl or furan; or If $G_1$ is Piperidine then $G_2$ is not alkyl; and
If $G_1$ is Piperazine, then $G_2$ is not alkyl or furan.

In some embodiments, $G_1$ is pyrrolidine and $G_2$ is ethyl or furan. In some embodiments, $G_1$ is substituted piperazine and $G_2$ is furan or phenyl and in some embodiments, $G_1$ is piperidine and $G_2$ is cyclopentyl, furan or phenyl. In some embodiments, $G_1$ is optionally substituted imidazolidine or optionally substituted pyrazolidine.

In some aspects, a compound of this invention and/or a composition of this invention may comprise and/or a method of this invention may provide for the use and/or a first medical use of this invention may include an agent characterized by the structure of Formula V:

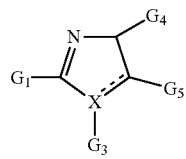

Formula V

Wherein X is N or S;
$G_1$ is substituted or unsubstituted pyrrolidine, substituted or unsubstituted pyridine, substituted or unsubstituted aryl, substituted or unsubstituted piperidine, substituted or unsubstituted piperazine, substituted or unsubstituted imidazolidine, or substituted or unsubstituted pyrazolidine;
G3 is

or G3 is substituted or unsubstituted alkyl, substituted or unsubstituted aryl or substituted or unsubstituted cyloalkyl, if X is N;
G3 is nothing, if X is S;
G4 or G5 is each, independently,

substituted or unsubstituted alkyl, alkoxy, acyl, substituted or unsubstituted aryl or substituted or unsubstituted cyloalkyl, if X is S;
G4 or G5 is each independently H, OH, halogen, if X is N; and
G2 is substituted or unsubstituted alkyl, alkoxy, acyl, substituted or unsubstituted aryl, substituted or unsubstituted cyloalkyl or substituted or unsubstituted heterocycle.

In some embodiments, this invention provides a compound characterized by the structure of Formula VI:

Formula VI

Wherein:
G1 is optionally substituted NH-pyrrolidine, optionally substituted NH-piperidine, optionally substituted NH-piperazine, optionally substituted NH-imidazolidine, optionally substituted NH-pyrazolidine, optionally substituted NH-aryl, optionally substituted NH-cycloalkyl, optionally substituted pyrrolidine, optionally substituted piperidine, optionally substituted piperidin, optionally substituted piperazine, optionally substituted imidazolidine, or optionally substituted pyrazolidine;
$G_2$ is optionally substituted alkyl, optionally substituted aryl, optionally substituted cyloalkyl or optionally substituted heterocycle;

Wherein:
If $G_1$ is unsubstituted pyrrolidine, then $G_2$ is not alkyl, cyclopentyl, alkylcyclopentyl or furan; or
If $G_1$ is Piperidine then $G_2$ is not alkyl; and
If $G_1$ is Piperazine, then $G_2$ is not alkyl or furan.

In some embodiments, $G_1$ is pyrrolidine and $G_2$ is ethyl or furan. In some embodiments, $G_1$ is substituted piperazine and G2 is furan or phenyl and in some embodiments, $G_1$ is piperidine and $G_2$ is cyclopentyl, furan or phenyl. In some embodiments, G1 is optionally substituted imidazolidine or optionally substituted pyrazolidine.

In some embodiments, G1 is optionally substituted NH-pyrrolidine, optionally substituted NH-piperidine, optionally substituted NH-piperazine, and G2 is optionally substituted alkyl; or in some embodiments, G1 is optionally substituted NH-pyrrolidine, optionally substituted NH-piperidine, optionally substituted NH-piperazine, and G2 is optionally substituted alkenyl; or in some embodiments, G1 is optionally substituted NH-pyrrolidine, optionally substituted NH-piperidine, optionally substituted NH-piperazine, and G2 is optionally substituted aryl; or in some embodiments, G1 is optionally substituted NH-pyrrolidine, optionally substituted NH-piperidine, optionally substituted NH-piperazine, and G2 is optionally substituted heteroaryl; or in some embodiments, G2 is optionally substituted cyloalkyl; or in some embodiments, G1 is optionally substituted NH-pyrrolidine, optionally substituted NH-piperidine, optionally substituted NH-piperazine, and G2 is optionally substituted heterocycle.

In some embodiments, G1 is optionally substituted NH-imidazolidine or optionally substituted NH-pyrazolidine, and G2 is optionally substituted alkyl; or in some embodiments, G1 is NH-imidazolidine or optionally substituted NH-pyrazolidine, and G2 is optionally substituted alkenyl; or in some embodiments, G1 is NH-imidazolidine or optionally substituted NH-pyrazolidine, and G2 is optionally substituted aryl; or in some embodiments, G1 is NH-imidazolidine or optionally substituted NH-pyrazolidine, and G2 is optionally substituted heteroaryl; or in some embodiments, G2 is optionally substituted cyloalkyl; or in some embodiments, G1 is NH-imidazolidine or optionally substituted NH-pyrazolidine, and G2 is optionally substituted heterocycle.

In some embodiments, G1 is optionally substituted NH-aryl, optionally substituted NH-cycloalkyl, and G2 is optionally substituted alkyl; or in some embodiments, G1 is optionally substituted NH-aryl, optionally substituted NH-cycloalkyl, and G2 is optionally substituted alkenyl; or in some embodiments, G1 is optionally substituted NH-aryl, optionally substituted NH-cycloalkyl, and G2 is optionally substituted aryl; or in some embodiments, G1 is optionally substituted NH-aryl, optionally substituted NH-cycloalkyl, and G2 is optionally substituted heteroaryl; or in some embodiments, G2 is optionally substituted cyoalkyl; or in some embodiments, G1 is optionally substituted NH-aryl, optionally substituted NH-cycloalkyl and G2 is optionally substituted heterocycle.

In some embodiments, G1 is optionally substituted pyrrolidine, optionally substituted piperidine, optionally substituted piperidin, and G2 is optionally substituted alkyl; or in some embodiments, G1 is optionally substituted pyrrolidine, optionally substituted piperidine, optionally substituted piperidin, and G2 is optionally substituted alkenyl; or in some embodiments, G1 is optionally substituted pyrrolidine, optionally substituted piperidine, optionally substituted piperidin, and G2 is optionally substituted aryl; or in some embodiments, G1 is optionally substituted pyrrolidine, optionally substituted piperidine, optionally substituted piperidin, and G2 is optionally substituted heteroaryl; or in some embodiments, G2 is optionally substituted cyloalkyl; or in some embodiments, G1 is optionally substituted pyrrolidine, optionally substituted piperidine, optionally substituted piperidin, and G2 is optionally substituted heterocycle.

In some embodiments, G1 is optionally substituted piperazine, optionally substituted imidazolidine, or optionally substituted pyrazolidine and G2 is optionally substituted alkyl; or in some embodiments, G1 is optionally substituted pyrrolidine, optionally substituted piperidine, optionally substituted piperidin, and G2 is optionally substituted alkenyl; or in some embodiments, G1 is optionally substituted piperazine, optionally substituted imidazolidine, or optionally substituted pyrazolidine and G2 is optionally substituted aryl; or in some embodiments, G1 is optionally substituted piperazine, optionally substituted imidazolidine, or optionally substituted pyrazolidine and G2 is optionally substituted heteroaryl; or in some embodiments, G2 is optionally substituted cyloalkyl; or in some embodiments, G1 is optionally substituted piperazine, optionally substituted imidazolidine, or optionally substituted pyrazolidine and G2 is optionally substituted heterocycle.

In some embodiments, this invention provides a compound characterized by the structure of Formula VII:

Formula VII

Wherein:
G1 is optionally substituted NH-pyrrolidine, optionally substituted NH-piperidine, optionally substituted NH-piperazine, optionally substituted NH-imidazolidine, optionally substituted NH-pyrazolidine, optionally substituted NH-pyridine, optionally substituted NH-aryl, optionally substituted NH-cycloalkyl, optionally substituted pyrrolidine, optionally substituted piperidine, optionally substituted piperidine, optionally substituted piperazine, optionally substituted imidazolidine, optionally substituted pyrazolidine or optionally substituted aryl;

G₂ is

or optionally substituted alkyl, optionally substituted aryl or optionally substituted cyloalky; and G₄ is optionally substituted pyrrolidine, optionally substituted piperidine, optionally substituted piperazine, optionally substituted imidazolidine or optionally substituted pyrazolidine;

Wherein:

If G₁ is Piperidine then G₄ is not pyrrolidine or G₂ is not optionally substituted aryl; or If G₁ is imidazolidine, then G₂ is not optionally substituted aryl; or If G₁ is optionally substituted NH-pyridine, then G₂ is not optionally substituted aryl; or If G₁ is optionally substituted NH-aryl, then G₂ is not optionally substituted aryl; or If G₁ is optionally substituted pyridine, then G₂ is not optionally substituted aryl.

In some embodiments, according to this aspect, G₁ is optionally substituted NH-pyridine, G₂ is

wherein G₄ is pyrrolidine, or G₂ is haloaryl and in some embodiments, according to this aspect, G₁ is substituted NH-aryl and G₂ is

wherein G₄ is pyrrolidine

In some aspects, reference to the term "substituted" with respect to the alkyl, alkenyl, pyrrolidine, piperidine, piperazine, imidazolidine pyrazolidine, aryl, heteroaryl, heterocyclic ring, or cycloalkyl groups may include a halogen, hydroxyl, $C_1$-$C_6$ straight or branched chain alkyl, nitro, CN, nitrileamido, amidosulfide, amino, aldehyde, substituted ketone, —COOH, ester, trifluoromethyl, amide, alkoxy or haloalkyl group or any subcombination thereof.

In some aspects, reference to the term "substituted" with respect to the alkyl, alkenyl, pyrrolidine, piperidine, piperazine, imidazolidine pyrazolidine, aryl, heteroaryl, heterocyclic ring, or cycloalkyl groups may include a halogen, hydroxyl, $C_1$-$C_6$ straight or branched chain alkyl, nitro, CN, nitrileamido, amidosulfide, amino, aldehyde, or any subcombination thereof or in some embodiments, substituted ketone, —COOH, ester, trifluoromethyl, amide, alkoxy or haloalkyl group or any subcombination thereof, or in some embodiments, a halogen, hydroxyl, $C_1$-$C_6$ straight or branched chain alkyl, or any subcombination thereof, or in some embodiments, nitro, CN, nitrileamido, amidosulfide, amino, aldehyde, or any subcombination thereof.

In some aspects, the term "alkyl" is to be understood to encompass a straight or branched chain C1-C6 alkyl. In some aspects, the term "cycloalkyl" is to be understood to encompass a 3-, 4-, 5- or 6-membered unsaturated ring.

In some aspects, the term "Alkyl" is intended to include linear, branched, or cyclic hydrocarbon structures and combinations thereof. Examples of alkyl groups include methyl, ethyl, propyl, isopropyl, butyl, s- and t-butyl and the like. In some embodiments, alkyl groups are those of C20 or below. In some embodiments, alkyl groups are those of C7 or below. In some embodiments, alkyl groups are those of C6 and below. Cycloalkyl is a subset of alkyl and includes cyclic hydrocarbon groups of from 3 to 13 carbon atoms. Examples of cycloalkyl groups include c-propyl, c-butyl, c-pentyl, norbornyl, adamantyl and the like. In this application, alkyl refers to alkanyl, alkenyl and alkynyl residues; it is intended to include cyclohexylmethyl, vinyl, allyl, isoprenyl and the like. Alkylen is another subset of alkyl, referring to the same residues as alkyl, but having two points of attachment. Examples of alkylen include ethylene (—CH2CH2-), propylene (—CH2CH2CH2-), dimethylpropylene (—CH2C (CH3) 2CH2-) and cyclohexylpropylene (—CH2CH2CH (C6H13)-). When an alkyl residue having a specific number of carbons is named, all geometric isomers having that number of carbons are intended to be encompassed; thus, for example, "butyl" is meant to include n-butyl, sec-butyl, isobutyl and t-butyl; "propyl" includes n-propyl and isopropyl.

The term "alkoxy" or "alkoxyl" herein may refer to the group-O-alkyl, preferably including from 1 to 8 carbon atoms of a straight, branched, cyclic configuration and combinations thereof attached to the parent structure through an oxygen. Examples include methoxy, ethoxy, propoxy, isopropoxy, cyclopropyloxy, cyclohexyloxy and the like.

The term "substituted alkoxy" may refer herein to the group-O-(substituted alkyl).

The term "Acyl" may refer herein to groups of from 1 to 10 carbon atoms of a straight, branched, cyclic configuration, saturated, unsaturated and aromatic and combinations thereof, attached to the parent structure through a carbonyl functionality. One or more carbons in the acyl residue may be replaced by nitrogen, oxygen or sulfur as long as the point of attachment to the parent remains at the carbonyl. Examples include acetyl, benzoyl, propionyl, isobutyryl, t-butoxycarbonyl, benzyloxycarbonyl and the like.

The term "Aryl" may refer herein to a 5- or 6-membered aromatic ring, a bicyclic 9- or 10-membered aromatic ring system, or a tricyclic 12- to 14-membered aromatic ring system. Examples include cyclopenta-1, 3-diene, phenyl, naphthyl, indane, tetralin, fluorene, cyclopenta [b] naphthalene and anthracene.

The term "Heterocycle" or "heterocyclyl" may refer herein to a cycloalkyl residue in which one to four of the carbons is replaced by a heteroatom such as oxygen, nitrogen or sulfur. a 4-, 5-, 6- or 7-membered non-aromatic ring containing 1-4 heteroatoms, a bicyclic 8-, 9- or 10-membered non-aromatic ring system containing 1-4 (or more) heteroatoms, or a tricyclic 11- to 14-membered non-aromatic ring system containing 1-4 (or more) heteroatoms; the heteroatoms are selected from O, N or S. Examples include pyrrolidine, tetrahydrofuran, tetrahydro-thiophene, thiazolidine, piperidine, tetrahydro-pyran, tetrahydro-thiopyran, piperazine, morpholine, thiomorpholine and dioxane.

The term "Heterocycle" or "heterocyclyl" may refer herein to ring systems including unsaturated bonds, provided the number and placement of unsaturation does not render the group aromatic. Examples include imidazoline, oxazoline, tetrahydroisoquinoline, benzodioxan, benzodioxole and 3, 5-dihydrobenzoxazinyl. Examples of substituted heterocyclyl include 4-methyl-1-piperazinyl and 4-benzyl-1-piperidinyl.

The term "arylalkyl" in some aspects is to be understood to provide for the definitions provided herein with respect to both aryl and alkyl groups and similarly, any combined functional group term is to be understood as encompassing the descriptions of each group independently, as well.

The term "optional" or "optionally" means that the subsequently described event or circumstance may or may not occur, and that the description includes instances where said event or circumstance occurs and instances in which it does not.

For example, "optionally substituted alkyl" means either "alkyl" or "substituted alkyl," as defined below. It will be understood by those skilled in the art with respect to any group containing one or more substituents that such groups are not intended to introduce any substitution or substitution patterns (e. g., substituted alkyl includes optionally substituted cycloalkyl groups, which in turn are defined as including optionally substituted alkyl groups, potentially ad infinitum) that are sterically impractical, synthetically non-feasible and/or inherently unstable. The term "substituted or unsubstituted" will be understood to encompass the same choice in terms of whether or not the indicated group contains one or more substituents.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound" or "stable structure" is meant a compound that is sufficiently robust to survive isolation to a. useful degree of purity from a. reaction mixture, and formulation into an efficacious therapeutic agent. The term "optionally substituted" means optional substitution with the specified groups, radicals or moieties.

It should also be noted that any carbon as well as heteroatom with unsatisfied valences in the text, schemes, examples and Tables herein is assumed to have the sufficient number of hydrogen atom(s) to satisfy the valences.

As noted herein, the invention contemplates any isomer or pharmaceutically acceptable salt, N-oxide, hydrate, prodrug, solvate, or derivative of a compound as herein described, compositions comprising any isomer or pharmaceutically acceptable salt, N-oxide, solvate, hydrate or derivative of a compound as herein described and first medical use of and/or methods of treatment employing any isomer or pharmaceutically acceptable salt, N-oxide, solvate, hydrate or derivative of a compound as herein described.

The term "pharmaceutically acceptable salt" may refer herein to salts that retain the biological effectiveness and properties of the compounds of this invention and, which are not biologically or otherwise undesirable. In many cases, the compounds of this invention are capable of forming acid and/or base salts by virtue of the presence of amino and/or carboxyl groups or groups similar thereto. Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like.

Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese, aluminum, and the like; particularly preferred are the ammonium, potassium, sodium, calcium and magnesium salts. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine.

The term "solvate" herein may refer to a compound in physical association with one or more molecules of a pharmaceutically acceptable solvent. The term "solvate" will be understood to encompass the stated compound, a pharmaceutically acceptable salt of the compound, a solvate of the compound, and a solvate of a pharmaceutically acceptable salt of the compound.

It will be understood that phrases such as "a compound as herein described" or "a compound for use as described" is to be considered to encompass a compound of Formula I-VII or any pharmaceutically acceptable salt, isomer, N-oxide, isomer or solvate thereof.

Prodrugs and solvates of the compounds of the invention are also contemplated herein. A discussion of prodrugs is provided in T. Higuchi and V. Stella, Pro-drugs as Novel Delivers Systems (1987) 14 of the A. C. S. Symposium Series, and in Bioreversible Carriers in Drug Design, (1987) Edward B. Roche, ed., American Pharmaceutical Association and Pergamon Press. The term "prodrug" means a compound (e.g., a drug precursor) that is transformed in vivo to yield a compound of Formula (I)-(IV) or a pharmaceutically acceptable salt, hydrate or solvate of the compound. The transformation may occur by various mechanisms (e.g., by metabolic or chemical processes), such as, for example, through hydrolysis in blood. A discussion of the use of prodrugs is provided by T. Higuchi and W. Stella, "Pro-drugs as Novel Delivery Systems," Vol. 14 of the A. C. S. Symposium Series, and in Bioreversible Carriers in Drug Design, ed. Edward B. Roche, American Pharmaceutical Association and Pergamon Press, 1987.

An exemplary Cathepsin C inhibitor which may be used in accordance with the present invention includes Gly-Phe-diazomethylketone (Gly-Phe-DMK) available e.g. from MP Biomedicals, USA.

According to some embodiments of the present invention, any bioinformatics method may be used to design and synthesize specific inhibitors of at least one of intracellular CELA3A or a structurally related enzyme, CELA1, and/or Cathepsin C (e.g. bioinformatic technologies such as Vigyaan, DNALinux Virtual Desktop (VD) or Bioclipse).

As mentioned, another agent capable of downregulating an activity or expression of Cathepsin C, CELA3A and CELA1 is a polynucleotide agent suitable for silencing expression in a targeted manner. Examples of such agents are listed infra.

Downregulation of at least one of intracellular CELA3A, CELA1, and/or Cathepsin C can be achieved by RNA silencing. As used herein, the phrase "RNA silencing" refers to a group of regulatory mechanisms [e.g. RNA interference (RNAi), transcriptional gene silencing (TGS), post-transcriptional gene silencing (PTGS), quelling, co-suppression, and translational repression] mediated by RNA molecules which result in the inhibition or "silencing" of the expression of a corresponding protein-coding gene. RNA silencing has been observed in many types of organisms, including plants, animals, and fungi.

As used herein, the term "RNA silencing agent" refers to an RNA which is capable of specifically inhibiting or "silencing" the expression of a target gene. In certain embodiments, the RNA silencing agent is capable of preventing complete processing (e.g., the full translation and/or expression) of an mRNA molecule through a post-transcriptional silencing mechanism. RNA silencing agents include noncoding RNA molecules, for example RNA duplexes comprising paired strands, as well as precursor RNAs from which such small non-coding RNAs can be generated. Exemplary RNA silencing agents include dsRNAs such as siRNAs, miRNAs and shRNAs. In one embodiment, the RNA silencing agent is capable of inducing RNA interference. In another embodiment, the RNA silencing agent is capable of mediating translational repression.

According to an embodiment of the invention, the RNA silencing agent is specific to the target RNA (e.g., Cathepsin C, CELA3A and CELA1) and does not cross inhibit or silence a gene or a splice variant which exhibits 99% or less global homology to the target gene, e.g., less than 98%, 97%, 96%, 95%, 94%, 93%, 92%, 91%, 90%, 89%, 88%, 87%, 86%, 85%, 84%, 83%, 82%, 81% global homology to the target gene.

RNA interference refers to the process of sequence-specific post-transcriptional gene silencing in animals mediated by short interfering RNAs (siRNAs). The corresponding process in plants is commonly referred to as post-transcriptional gene silencing or RNA silencing and is also referred to as quelling in fungi. The process of post-transcriptional gene silencing is thought to be an evolutionarily-conserved cellular defense mechanism used to prevent the expression of foreign genes and is commonly shared by diverse flora and phyla. Such protection from foreign gene expression may have evolved in response to the production of double-stranded RNAs (dsRNAs) derived from viral infection or from the random integration of transposon elements into a host genome via a cellular response that specifically destroys homologous single-stranded RNA or viral genomic RNA.

The presence of long dsRNAs in cells stimulates the activity of a ribonuclease III enzyme referred to as dicer. Dicer is involved in the processing of the dsRNA into short pieces of dsRNA known as short interfering RNAs (siRNAs). Short interfering RNAs derived from dicer activity are typically about 21 to about 23 nucleotides in length and comprise about 19 base pair duplexes. The RNAi response also features an endonuclease complex, commonly referred to as an RNA-induced silencing complex (RISC), which mediates cleavage of single-stranded RNA having sequence complementary to the antisense strand of the siRNA duplex. Cleavage of the target RNA takes place in the middle of the region complementary to the antisense strand of the siRNA duplex.

Accordingly, some embodiments of the invention contemplate use of dsRNA to downregulate protein expression from mRNA.

According to one embodiment, the dsRNA is greater than 30 bp. The use of long dsRNAs (i.e. dsRNA greater than 30 bp) has been very limited owing to the belief that these longer regions of double stranded RNA will result in the induction of the interferon and PKR response. However, the use of long dsRNAs can provide numerous advantages in that the cell can select the optimal silencing sequence alleviating the need to test numerous siRNAs; long dsRNAs will allow for silencing libraries to have less complexity than would be necessary for siRNAs; and, perhaps most importantly, long dsRNA could prevent viral escape mutations when used as therapeutics.

Various studies demonstrate that long dsRNAs can be used to silence gene expression without inducing the stress response or causing significant off-target effects—see for example [Strat et al., Nucleic Acids Research, 2006, Vol. 34, No. 13 3803-3810; Bhargava A et al. Brain Res. Protoc. 2004; 13:115-125; Diallo M., et al., Oligonucleotides. 2003; 13:381-392; Paddison P. J., et al., Proc. Natl Acad. Sci. USA. 2002; 99:1443-1448; Tran N., et al., FEBS Lett. 2004; 573:127-134].

In particular, the invention according to some embodiments thereof contemplates introduction of long dsRNA (over 30 base transcripts) for gene silencing in cells where the interferon pathway is not activated (e.g. embryonic cells and oocytes) see for example Billy et al., PNAS 2001, Vol 98, pages 14428-14433. and Diallo et al, Oligonucleotides, Oct. 1, 2003, 13(5): 381-392. doi:10.1089/154545703322617069.

The invention according to some embodiments thereof also contemplates introduction of long dsRNA specifically designed not to induce the interferon and PKR pathways for down-regulating gene expression. For example, Shinagwa and Ishii [*Genes & Dev.* 17 (11): 1340-1345, 2003] have developed a vector, named pDECAP, to express long double-strand RNA from an RNA polymerase II (Pol II) promoter. Because the transcripts from pDECAP lack both the 5'-cap structure and the 3'-poly(A) tail that facilitate ds-RNA export to the cytoplasm, long ds-RNA from pDECAP does not induce the interferon response.

Another method of evading the interferon and PKR pathways in mammalian systems is by introduction of small inhibitory RNAs (siRNAs) either via transfection or via endogenous expression.

The term "siRNA" refers to small inhibitory RNA duplexes (generally between 18-30 base pairs) that induce the RNA interference (RNAi) pathway. Typically, siRNAs are chemically synthesized as 21mers with a central 19 bp duplex region and symmetric 2-base 3'-overhangs on the termini, although it has been recently described that chemically synthesized RNA duplexes of 25-30 base length can have as much as a 100 fold increase in potency compared with 21mers at the same location. The observed increased potency obtained using longer RNAs in triggering RNAi is theorized to result from providing Dicer with a substrate (27mer) instead of a product (21mer) and that this improves the rate or efficiency of entry of the siRNA duplex into RISC.

It has been found that position of the 3'-overhang influences potency of a siRNA and asymmetric duplexes having a 3'-overhang on the antisense strand are generally more potent than those with the 3'-overhang on the sense strand (Rose et al., 2005). This can be attributed to asymmetrical strand loading into RISC, as the opposite efficacy patterns are observed when targeting the antisense transcript.

The strands of a double-stranded interfering RNA (e.g., a siRNA) may be connected to form a hairpin or stem-loop structure (e.g., a shRNA). Thus, as mentioned the RNA silencing agent of some embodiments of the invention may also be a short hairpin RNA (shRNA).

The term "shRNA", as used herein, refers to an RNA agent having a stem-loop structure, comprising a first and second region of complementary sequence, the degree of complementarity and orientation of the regions being sufficient such that base pairing occurs between the regions, the first and second regions being joined by a loop region, the loop resulting from a lack of base pairing between nucleotides (or nucleotide analogs) within the loop region. The number of nucleotides in the loop is a number between and including 3 to 23, or 5 to 15, or 7 to 13, or 4 to 9, or 9 to 11. Some of the nucleotides in the loop can be involved in base-pair interactions with other nucleotides in the loop. Examples of oligonucleotide sequences that can be used to form the loop include 5'-UUCAAGAGA-3' (Brummelkamp, T. R. et al. (2002) Science 296: 550) and 5'-UUUGUGUAG-3' (Castanotto, D. et al. (2002) RNA 8:1454). It will be recognized by one of skill in the art that the resulting single chain oligonucleotide forms a stem-loop or hairpin structure comprising a double-stranded region capable of interacting with the RNAi machinery.

Synthesis of RNA silencing agents suitable for use with some embodiments of the invention can be effected as follows. First, the Cathepsin C, CELA3A and CELA1 mRNA sequence is scanned downstream of the AUG start codon for AA dinucleotide sequences. Occurrence of each AA and the 3' adjacent 19 nucleotides is recorded as potential siRNA target sites. Preferably, siRNA target sites are selected from the open reading frame, as untranslated regions (UTRs) are richer in regulatory protein binding sites. UTR-binding proteins and/or translation initiation complexes may interfere with binding of the siRNA endonuclease complex [Tuschl ChemBiochem. 2:239-245]. It will be appreciated though, that siRNAs directed at untranslated regions may also be effective, as demonstrated for GAPDH wherein siRNA directed at the 5' UTR mediated about 90% decrease in cellular GAPDH mRNA and completely abolished protein level (www.ambion.com/techlib/tn/91/912.html).

Second, potential target sites are compared to an appropriate genomic database (e.g., human, mouse, rat etc.) using any sequence alignment software, such as the BLAST software available from the NCBI server (www.ncbi.nlm.nih.gov/BLAST/). Putative target sites which exhibit significant homology to other coding sequences are filtered out.

Qualifying target sequences are selected as template for siRNA synthesis. Preferred sequences are those including low G/C content as these have proven to be more effective in mediating gene silencing as compared to those with G/C content higher than 55%. Several target sites are preferably selected along the length of the target gene for evaluation. For better evaluation of the selected siRNAs, a negative control is preferably used in conjunction. Negative control siRNA preferably include the same nucleotide composition as the siRNAs but lack significant homology to the genome. Thus, a scrambled nucleotide sequence of the siRNA is preferably used, provided it does not display any significant homology to any other gene.

For example, a suitable siRNA molecule for Cathepsin C can comprise the nucleic acid sequence as set forth in SEQ ID NO: 1.

An exemplary siRNA molecule, miRNA molecule or shRNA molecule for Cathepsin C silencing can be commercially purchased from e.g. Sigma-Aldrich, QIAGEN or OnGene.

For example, a suitable siRNA molecule for CELA1 can comprise the nucleic acid sequence as set forth in SEQ ID NO: 2.

An exemplary siRNA molecule, miRNA molecule or shRNA molecule for CELA1 silencing can be commercially purchased from e.g. Sigma-Aldrich, QIAGEN or OnGene.

For example, a suitable siRNA molecule for CELA3A can comprise the nucleic acid sequence as set forth in SEQ ID NO: 3.

An exemplary siRNA molecule, miRNA molecule or shRNA molecule for CELA3A silencing can be commercially purchased from e.g. Sigma-Aldrich, QIAGEN or OnGene.

The present invention further provides an isolated polynucleotide comprising a nucleic acid sequence sharing at least from 95% up to 99% identity with or as set forth in SEQ ID NO: 1.

The present invention further provides an isolated polynucleotide comprising a nucleic acid sequence sharing at least from 95% up to 99% identity with or as set forth in SEQ ID NO: 2.

The present invention further provides an isolated polynucleotide comprising a nucleic acid sequence sharing at least from 95% up to 99% identity with or as set forth in SEQ ID NO: 3.

It will be appreciated that the RNA silencing agent of some embodiments of the invention need not be limited to those molecules containing only RNA, but further encompasses chemically-modified nucleotides and non-nucleotides.

mRNAs to be targeted using RNA silencing agents include, but are not limited to, those whose expression is correlated with an undesired phenotypic trait. Exemplary mRNAs that may be targeted are those that encode truncated proteins i.e. comprise deletions. Accordingly the RNA silencing agent of some embodiments of the invention may be targeted to a bridging region on either side of the deletion. Introduction of such RNA silencing agents into a cell would cause a down-regulation of the mutated protein while leaving the non-mutated protein unaffected.

According to another embodiment the RNA silencing agent may be a miRNA.

The term "microRNA", "miRNA", and "miR" are synonymous and refer to a collection of non-coding single-stranded RNA molecules of about 19-28 nucleotides in length, which regulate gene expression. miRNAs are found in a wide range of organisms (viruses, humans) and have been shown to play a role in development, homeostasis, and disease etiology.

It should be noted that there may be variability in the 5' and 3' ends of any pair of miRNA and miRNA*. This variability may be due to variability in the enzymatic processing of Drosha and Dicer with respect to the site of cleavage. Variability at the 5' and 3' ends of miRNA and miRNA* may also be due to mismatches in the stem structures of the pri-miRNA and pre-miRNA. The mismatches of the stem strands may lead to a population of different hairpin structures. Variability in the stem structures may also lead to variability in the products of cleavage by Drosha and Dicer.

Another agent capable of downregulating Cathepsin C, CELA3A and CELA1 is a DNAzyme molecule capable of specifically cleaving an mRNA transcript or DNA sequence of the Cathepsin C, CELA3A and CELA1. DNAzymes are single-stranded polynucleotides which are capable of cleaving both single and double stranded target sequences. (Breaker, R. R. and Joyce, G. Chemistry and Biology 1995; 2:655; Santoro, S. W. & Joyce, G. F. Proc. Natl, Acad. Sci. USA 1997; 943:4262 A general model (the "$10^{-23}$" model) for the DNAzyme has been proposed. "$10^{-23}$" DNAzymes have a catalytic domain of 15 deoxyribonucleotides, flanked by two substrate-recognition domains of seven to nine deoxyribonucleotides each. This type of DNAzyme can effectively cleave its substrate RNA at purine:pyrimidine junctions (Santoro, S. W. & Joyce, G. F. Proc. Natl, Acad. Sci. USA 199; for rev of DNAzymes see Khachigian, L M [Curr Opin Mol Ther 4:119-21 (2002)].

Examples of construction and amplification of synthetic, engineered DNAzymes recognizing single and double-stranded target cleavage sites have been disclosed in U.S. Pat. No. 6,326,174 to Joyce et al. DNAzymes of similar design directed against the human Urokinase receptor were recently observed to inhibit Urokinase receptor expression, and successfully inhibit colon cancer cell metastasis in vivo (Itoh et al, 2002, Abstract 409, Ann Meeting Am Soc Gen Ther wwwdotasgtdotorg). In another application, DNAzymes complementary to bcr-abl oncogenes were successful in inhibiting the oncogenes expression in leukemia cells, and lessening relapse rates in autologous bone marrow transplant in cases of CML and ALL.

Downregulation of a Cathepsin C, CELA3a and CELA1 can also be effected by using an antisense polynucleotide capable of specifically hybridizing with an mRNA transcript encoding the Cathepsin C, CELA3A and CELA1.

Design of antisense molecules which can be used to efficiently downregulate at least one of intracellular CELA3A, CELA1, and/or Cathepsin C must be effected while considering two aspects important to the antisense approach. The first aspect is delivery of the oligonucleotide into the cytoplasm of the appropriate cells, while the second aspect is design of an oligonucleotide which specifically binds the designated mRNA within cells in a way which inhibits translation thereof.

The prior art teaches of a number of delivery strategies which can be used to efficiently deliver oligonucleotides into a wide variety of cell types [see, for example, Luft J Mol Med 76: 75-6 (1998); Kronenwett et al. Blood 91: 852-62 (1998); Rajur et al. Bioconjug Chem 8: 935-40 (1997); Lavigne et al. Biochem Biophys Res Commun 237: 566-71 (1997) and Aoki et al. (1997) Biochem Biophys Res Commun 231: 540-5 (1997)].

In addition, algorithms for identifying those sequences with the highest predicted binding affinity for their target mRNA based on a thermodynamic cycle that accounts for the energetics of structural alterations in both the target mRNA and the oligonucleotide are also available [see, for example, Walton et al. Biotechnol Bioeng 65: 1-9 (1999)].

Such algorithms have been successfully used to implement an antisense approach in cells. For example, the algorithm developed by Walton et al. enabled scientists to successfully design antisense oligonucleotides for rabbit beta-globin (RBG) and mouse tumor necrosis factor-alpha (TNF alpha) transcripts. The same research group has more recently reported that the antisense activity of rationally selected oligonucleotides against three model target mRNAs (human lactate dehydrogenase A and B and rat gp130) in cell culture as evaluated by a kinetic PCR technique proved effective in almost all cases, including tests against three different targets in two cell types with phosphodiester and phosphorothioate oligonucleotide chemistries.

In addition, several approaches for designing and predicting efficiency of specific oligonucleotides using an in vitro system were also published (Matveeva et al., Nature Biotechnology 16: 1374-1375 (1998)].

Another agent capable of downregulating a Cathepsin C, CELA3A and CELA1 is a ribozyme molecule capable of specifically cleaving an mRNA transcript encoding a Cathepsin C, CELA3A and CELA1. Ribozymes are being increasingly used for the sequence-specific inhibition of gene expression by the cleavage of mRNAs encoding proteins of interest [Welch et al., Curr Opin Biotechnol. 9:486-96 (1998)]. The possibility of designing ribozymes to cleave any specific target RNA has rendered them valuable tools in both basic research and therapeutic applications. In the therapeutics area, ribozymes have been exploited to target viral RNAs in infectious diseases, dominant oncogenes in cancers and specific somatic mutations in genetic disorders [Welch et al., Clin Diagn Virol. 10:163-71 (1998)]. Most notably, several ribozyme gene therapy protocols for HIV patients are already in Phase 1 trials. More recently, ribozymes have been used for transgenic animal research, gene target validation and pathway elucidation. Several ribozymes are in various stages of clinical trials. ANGIOZYME was the first chemically synthesized ribozyme to be studied in human clinical trials. ANGIOZYME specifically inhibits formation of the VEGF-r (Vascular Endothelial Growth Factor receptor), a key component in the angiogenesis pathway. Ribozyme Pharmaceuticals, Inc., as well as other firms have demonstrated the importance of anti-angiogenesis therapeutics in animal models. HEPTAZYME, a ribozyme designed to selectively destroy Hepatitis C Virus (HCV) RNA, was found effective in decreasing Hepatitis C viral RNA in cell culture assays (Ribozyme Pharmaceuticals, Incorporated—WEB home page).

Thus for any given sequence in the Cathepsin C, CELA3A and CELA1 regulatory region a triplex forming sequence may be devised. Triplex-forming oligonucleotides preferably are at least 15, more preferably 25, still more preferably 30 or more nucleotides in length, up to 50 or 100 bp.

Transfection of cells (for example, via cationic liposomes) with TFOs, and formation of the triple helical structure with the target DNA induces steric and functional changes, blocking transcription initiation and elongation, allowing the introduction of desired sequence changes in the endogenous DNA and resulting in the specific downregulation of gene expression. Examples of such suppression of gene expression in cells treated with TFOs include knockout of episomal supFG1 and endogenous HPRT genes in mammalian cells (Vasquez et al., Nucl Acids Res. 1999; 27:1176-81, and Puri, et al, J Biol Chem, 2001; 276:28991-98), and the sequence- and target specific downregulation of expression of the Ets2 transcription factor, important in prostate cancer etiology (Carbone, et al, Nucl Acid Res. 2003; 31:833-43), and the pro-inflammatory ICAM-1 gene (Besch et al, J Biol Chem, 2002; 277:32473-79). In addition, Vuyisich and Beal have recently shown that sequence specific TFOs can bind to dsRNA, inhibiting activity of dsRNA-dependent enzymes such as RNA-dependent kinases (Vuyisich and Beal, Nuc. Acids Res 2000; 28:2369-74).

Additionally, TFOs designed according to the abovementioned principles can induce directed mutagenesis capable of effecting DNA repair, thus providing both downregulation and upregulation of expression of endogenous genes (Seidman and Glazer, J Clin Invest 2003; 112:487-94). Detailed description of the design, synthesis and administration of effective TFOs can be found in U.S. Patent Application Nos. 2003 017068 and 2003 0096980 to Froehler et al, and 2002 0128218 and 2002 0123476 to Emanuele et al, and U.S. Pat. No. 5,721,138 to Lawn.

Exemplary nucleic acid regions of CELA1 and CELA3A which may be targeted by the polynucleotide agent of the present teachings comprise the nucleic acid sequences as set forth in SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35 and SEQ ID NO: 36. It will be appreciated, however, that any nucleic acid region of Cathepsin C, CELA1 and/or CELA3A which silences expression thereof in a targeted manner may be used in accordance with the present teachings.

The present invention further provides an isolated polynucleotide that hybridizes specifically to CELA1 and/or CELA3A but not to CELA2A or CELA3B under moderate to stringent hybridization conditions. Stringent hybridization conditions of the present invention may be affected, for example, by a hybridization solution containing 10% dextrane sulfate, 1 M NaCl, 1% SDS and $5 \times 10^6$ cpm 32p-labeled probe, at 65° C., with a final wash solution of 0.2×SSC and 0.1% SDS and final wash at 65° C.; whereas moderate hybridization conditions may be affected, for example, by a hybridization solution containing 10% dextrane sulfate, 1 M NaCl, 1% SDS and $5 \times 10^6$ cpm 32p-labeled probe, at 65° C., with a final wash solution of 1×SSC and 0.1% SDS and final wash at 50° C.

The present invention further provides an isolated polynucleotide that hybridizes specifically to Cathepsin C but not to Cathepsins A, B, D, E, G, H, K, L1, L2, O, S, W or Z under moderate to stringent hybridization conditions.

The isolated polynucleotide agents for downregulating Cathepsin C, CELA1 and/or CELA3A expression in necrotizing cells may be provided to the cells per se. Such polynucleotide agents are typically administered to the cells as part of an expression construct. In this case, the polynucleotide agent is ligated in a nucleic acid construct under the control of a cis-acting regulatory element (e.g. promoter) capable of directing an expression of the polynucleotide agent in the cells in a constitutive or inducible manner.

The expression constructs of the present invention may also include additional sequences which render it suitable for replication and integration in eukaryotes (e.g., shuttle vectors). Typical cloning vectors contain transcription and translation initiation sequences (e.g., promoters, enhances) and transcription and translation terminators (e.g., polyadenylation signals). The expression constructs of the present invention can further include an enhancer, which can be adjacent or distant to the promoter sequence and can function in up regulating the transcription therefrom.

In addition to the embodiments already described, the expression constructs of the present invention may typically contain other specialized elements intended to increase the level of expression of cloned nucleic acids or to facilitate the identification of cells that carry the recombinant DNA. For example, a number of animal viruses contain DNA sequences that promote extra-chromosomal replication of the viral genome in permissive cell types. Plasmids bearing these viral replicons are replicated episomally as long as the appropriate factors are provided by genes carried either on the plasmid or with the genome of the host cell.

The expression constructs of the present invention may or may not include a eukaryotic replicon. If a eukaryotic replicon is present, the vector is capable of amplification in eukaryotic cells using the appropriate selectable marker. If the construct does not comprise a eukaryotic replicon, no episomal amplification is possible. Instead, the recombinant DNA integrates into the genome of the engineered cell, where the promoter directs expression of the desired nucleic acid.

The nucleic acid construct may be introduced into the necrotizing cells of the present invention using an appropriate gene delivery vehicle/method (transfection, transduction, etc.) and an appropriate expression system.

Examples of mammalian expression vectors include, but are not limited to, pcDNA3, pcDNA3.1(+/−), pGL3, pZeoSV2(+/−), pSecTag2, pDisplay, pEF/myc/cyto, pCMV/myc/cyto, pCR3.1, pSinRep5, DH26S, DHBB, pNMT1, pNMT41, and pNMT81, which are available from Invitrogen, pCI which is available from Promega, pMbac, pPbac, pBK-RSV and pBK-CMV, which are available from Stratgene, pTRES which is available from Clontech, and their derivatives.

Various methods can be used to introduce the expression vectors of the present invention into human cells. Such methods are generally described in, for instance: Sambrook, J. and Russell, D. W. (1989, 1992, 2001), Molecular Cloning: A Laboratory Manual, Cold Springs Harbor Laboratory, New York; Ausubel, R. M. et al., eds. (1994, 1989). Current Protocols in Molecular Biology, John Wiley and Sons, Baltimore, Md. (1989); Chang, P. L., ed. (1995). Somatic Gene Therapy, CRC Press, Boca Raton, Fla.; Vega, M. A. (1995). Gene Targeting, CRC Press, Boca Raton, Fla.; Rodriguez, R. L. and Denhardt, D. H. (1987). Vectors: A Survey of Molecular Cloning Vectors and Their Uses, Butterworth-Heinemann, Boston, Mass; and Gilboa, E. et al. (1986). Transfer and expression of cloned genes using retro-viral vectors. Biotechniques 4(6), 504-512; and include, for example, stable or transient transfection, lipofection, electroporation, and infection with recombinant viral vectors. In addition, see U.S. Pat. Nos. 5,464,764 and 5,487,992 for positive-negative selection methods.

Since each of at least one of intracellular CELA3A, CELA1, and/or Cathepsin C are intracellular targets the agents of the present invention may be formulated for intracellular delivery. For example, the high affinity binding molecule (e.g. antibody) of the present invention may be further designed for intracellular delivery.

In some embodiments, the RNA silencing agent provided herein can be functionally associated with a cell-penetrating peptide." As used herein, a "cell-penetrating peptide" is a peptide that comprises a short (about 12-30 residues) amino acid sequence or functional motif that confers the energy-independent (i.e., non-endocytotic) translocation properties associated with transport of the membrane-permeable complex across the plasma and/or nuclear membranes of a cell. The cell-penetrating peptide used in the membrane-permeable complex of some embodiments of the invention preferably comprises at least one non-functional cysteine residue, which is either free or derivatized to form a disulfide link with a double-stranded ribonucleic acid that has been modified for such linkage. Representative amino acid motifs conferring such properties are listed in U.S. Pat. No. 6,348,185, the contents of which are expressly incorporated herein by reference. The cell-penetrating peptides of some embodiments of the invention preferably include, but are not limited to, penetratin, transportan, pIsl, TAT(48-60), pVEC, MTS, and MAP.

Thus, for example, lipid-based systems may be used for the delivery of these antibodies into the target cells (e.g. a necrotic cell) of the present invention.

Liposomes include any synthetic (i.e., not naturally occurring) structure composed of lipid bilayers, which enclose a volume. Liposomes include emulsions, foams, micelles, insoluble monolayers, liquid crystals, phospholipid dispersions, lamellar layers and the like. The liposomes may be prepared by any of the known methods in the art [Monkkonen, J. et al., 1994, J. Drug Target, 2:299-308; Monkkonen, J. et al., 1993, Calcif Tissue Int., 53:139-145;

Lasic D D., Liposomes Technology Inc., Elsevier, 1993, 63-105. (chapter 3); Winterhalter M, Lasic D D, Chem Phys Lipids, 1993 September; 64(1-3):35-43]. The liposomes may be positively charged, neutral or negatively charged. For Mononuclear Phagocyte System (MPS) uptake, the liposomes can be hydrophobic since hydrophilic masking of the liposome membrane (e.g., by use of polyetheleneglycol-linked lipids and hydrophilic particles) may be less prone to MPS uptake. It is also preferable that the liposomes do not comprise sterically shielded lipids such as ganglioside-$GM_1$ and phosphatidylinositol since these lipids prevent MPS uptake.

The liposomes may be a single lipid layer or may be multilamellar. If the therapeutic agent is hydrophilic, its delivery may be further improved using large unilamellar vesicles because of their greater internal volume. Conversely, if the therapeutic agent is hydrophobic, its delivery may be further improved using multilamellar vesicles. Alternatively, the therapeutic agent (e.g. antibody) may not be able to penetrate the lipid bilayer and consequently would remain adsorbed to the liposome surface. In this case, increasing the surface area of the liposome may further improve delivery of the therapeutic agent. Suitable liposomes in accordance with the invention are non-toxic liposomes such as, for example, those prepared from phosphatidyl-choline phosphoglycerol, and cholesterol. The diameter of the liposomes used can range from 0.1-1.0 microns. However, other size ranges suitable for phagocytosis by phagocytic cells may also be used. For sizing liposomes, homogenization may be used, which relies on shearing energy to fragment large liposomes into smaller ones. Homogenizers which may be conveniently used include microfluidizers produced by Microfluidics of Boston, MA. In a typical homogenization procedure, liposomes are recirculated through a standard emulsion homogenizer until selected liposomes sizes are observed. The particle size distribution can be monitored by conventional laser beam particle size discrimination. Extrusion of liposomes through a small-pore polycarbonate membrane or an asymmetric ceramic membrane is an effective method for reducing liposome sizes to a relatively well defined size distribution. Typically, the suspension is cycled through the membrane one or more times until the desired liposome size distribution is achieved. The liposomes may be extruded through successively smaller pore membranes to achieve a gradual reduction in liposome size.

Any method known in the art can be used to incorporate a therapeutic agent of some embodiments of the invention into a liposome. For example, the high affinity molecule (e.g. antibody) may be encapsulated within the liposome. Alternatively, it may be adsorbed on the liposome's surface. Other methods that may be used to incorporate a pharmaceutical agent into a liposome of the present invention are those described by Alfonso et al., [The science and practice of pharmacy, Mack Publishing, Easton Pa 19$^{th}$ ed., (1995)] and those described by Kulkarni et al., [J. Microencapsul. 1995, 12 (3) 229-46].

The liposomes used in the methods of the present invention preferably cross the blood barriers. Thus, the liposomes of the present invention preferably do not comprise a blood barrier targeting polysaccharide (e.g. mannose) in their membrane portion. Preferably, the liposomes of the present invention do not comprise peptides in their membrane portion that target the liposomes to a receptor on a blood barrier. Examples of such peptides include but are not limited to transferrin, insulin, IGF-1, IGF-2 anti-transferrin receptor antibody, anti-insulin receptor antibody, anti-IGF-1 receptor antibody and anti-IGF-2 receptor antibody.

In order to determine liposomes that are especially suitable in accordance with the present invention a screening assay can be performed such as the assays described in U.S. Pat. Appl. No. 20040266734 and U.S. Pat. Appl. No. 20040266734; and in Danenberg et al., Journal of cardiovascular pharmacology 2003, 42:671-9; Circulation 2002, 106:599-605; Circulation 2003, 108:2798-804.

According to one embodiment, the method of preventing or inhibiting cell necrosis is effected in-vitro, in-vivo or ex-vivo.

The ability to modulate at least one of intracellular CELA3A, CELA1, and/or Cathepsin C can be used as a novel therapeutic modality for the treatment of necrosis induced cell death.

Thus, according to another aspect of the present invention there is provided a method of treating a medical disease or condition associated with cell necrosis in a subject in need thereof, the method comprising administering to the subject a therapeutically effective amount of an agent which specifically downregulates an expression and alternatively or additionally inhibits an activity of a Cathepsin C, a CELA3A and a CELA1 in a cell of the subject.

The term "treating" refers to inhibiting or arresting the development of a disease, disorder or condition and/or causing the reduction, remission, or regression of a disease, disorder or condition or keeping a disease, disorder or medical condition from occurring in a subject who may be at risk for the disease disorder or condition, but has not yet been diagnosed as having the disease disorder or condition. Those of skill in the art will understand that various methodologies and assays can be used to assess the development of a disease, disorder or condition, and similarly, various methodologies and assays may be used to assess the reduction, remission or regression of a disease, disorder or condition.

As used herein, the term "subject" refers to an animal, preferably a mammal, most preferably a human being, including both young and old human beings of both genders who suffer from or are predisposed to a necrosis related disorder or condition.

A diseases or conditions which is associated with cell necrosis includes, but is not limited to, a neurodegenerative disease, a dementia, a Parkinson disease, an Alzheimer's disease, a muscular dystrophy, a leukemia, a lymphoma, a neonatal respiratory distress, an asphyxia, an incarcerated hernia, a diabetes mellitus, a tuberculosis, an endometriosis, a vascular dystrophy, a psoriasis, a cold injury, an iron-load complication, a complication of steroid treatment, an ischemic heart disease, a reperfusion injury, a cerebrovascular disease or damage, a gangrene, a pressure sore, a pancreatitis, a hepatitis, a hemoglobinuria, a meningitis, a sphacelus, an ischemic necrosis, an avascular necrosis (e.g., of the bone), a bacterial sepsis, a viral sepsis, a burn, a hyperthermia, a Crohn's disease, a celiac disease, a compartment syndrome, a necrotizing procolitis, a cystic fibrosis, a rheumatoid arthritis, a nephrotoxicity, a multiple sclerosis, a spiral cord injury, a glomerulonephritis, a degenerative arthritis, a tyrosemia, a metabolic inherited disease, a mycoplasmal disease, an anthrax infection, a bacterial infection, a viral infection, an Anderson disease, a congenital mitochondrial disease, a phenylketonuria, a placental infarct, a syphilis, an aseptic necrosis, an avascular necrosis, an alcoholism and a necrosis associated with administration and/or self-administration with, and/or exposure to, cocaine, drugs, chemical toxins, agrochemicals and heavy metals, a necrosis associated with dermal fillers administration; a necrosis associated with ectopic drug administration, such as extravasation of dextrose solution, chemotherapeutic drugs; a chemotherapy-induced necrosis, a radiation induced necrosis, maintenance of transplant tissue and aging.

According to one embodiment, the disease or conditions which is associated with cell necrosis is brain injury (e.g. traumatic brain injury).

Thus, the present methods are useful in treating necrosis associated with any acute or chronic central nervous system (CNS) injury. Such a disease or condition may include, but is not limited to, stroke (caused by thrombosis, embolism or vasoconstriction), closed head injury, global cerebral ischemia (e.g., ischemia due to systemic hypotension of any cause, including cardiac infarction, cardiac arrhythmia, hemorrhagic shock, and post coronary artery bypass graft brain injury), focal ischemia and intracranial hemorrhage. Ischemic damage to the CNS can result from either global or focal ischemic conditions. Global ischemia occurs where blood flow to the entire brain ceases for a period of time, such as during cardiac arrest. Focal ischemia occurs when a portion of the brain is deprived of normal blood flow, such as during thromboembolytic occlusion of a cerebral vessel, traumatic head injury, edema and brain tumors. Much of the CNS damage due to cerebral ischemia occurs during the hours or even days following the ischemic condition, and is secondary to the release of cytotoxic products by damaged tissue.

In some aspects, the invention specific contemplates the treatment or prevention of liver toxicity arising from any known cause, e.g. infection-based, or toxic substance exposure, or others as will be appreciated by the skilled artisan.

In some aspects, the invention specifically contemplates the treatment or prevention of cardiac disease, including, in some aspects, myocardial infarction, cardiac insufficiency, heart failure, and others, as will be appreciated by the skilled artisan.

According to the present teachings, in order to treat the medical disease or condition associated with cell necrosis, the subject is administered with an agent which specifically downregulates an expression and alternatively or additionally inhibits an activity of a Cathepsin C, a CELA1 and/or a CELA3A or structurally related enzyme, as further detailed hereinabove.

It will be appreciated that each of the downregulating agents described hereinabove or the expression vector encoding the downregulating agents can be administered to the individual per se or as part of a pharmaceutical composition which also includes a physiologically acceptable carrier, or in some aspects, as part of a conjugate, charged particle, liposome or any known carrier in the art, which in turn may, in some aspects, be further formulated as part of a pharmaceutical composition. The purpose of a pharmaceutical composition is to facilitate administration of the active ingredient to an organism.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Herein the term "active ingredient" refers to the at least one of intracellular CELA3A, CELA1, and/or Cathepsin C, downregulating or inhibiting agent accountable for the biological effect.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, PA, latest edition, which is incorporated herein by reference.

Suitable routes of administration may, for example, include oral, rectal, transmucosal, especially transnasal, intestinal or parenteral delivery, including intramuscular, subcutaneous and intramedullary injections as well as intrathecal, direct intraventricular, intracardiac, e.g., into the right or left ventricular cavity, into the common coronary artery, intravenous, intraperitoneal, intranasal, or intraocular injections.

Conventional approaches for drug delivery to the central nervous system (CNS) include: neurosurgical strategies (e.g., intracerebral injection or intracerebroventricular infusion); molecular manipulation of the agent (e.g., production of a chimeric fusion protein that comprises a transport peptide that has an affinity for an endothelial cell surface molecule in combination with an agent that is itself incapable of crossing the BBB) in an attempt to exploit one of the endogenous transport pathways of the BBB; pharmacological strategies designed to increase the lipid solubility of an agent (e.g., conjugation of water-soluble agents to lipid or cholesterol carriers); and the transitory disruption of the integrity of the BBB by hyperosmotic disruption (resulting from the infusion of a mannitol solution into the carotid artery or the use of a biologically active agent such as an angiotensin peptide).

According to an embodiment of the present invention, the pharmaceutical composition is formulated for penetrating a cell membrane. Thus, for example, the pharmaceutical composition may comprise a lipid vesicle.

Alternately, one may administer the pharmaceutical composition in a local rather than systemic manner, for example, via injection of the pharmaceutical composition directly into a tissue region of a patient (e.g. necrotic tissue).

Pharmaceutical compositions of some embodiments of the invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with some embodiments of the invention thus may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the pharmaceutical composition can be formulated readily by combining the active compounds with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to some embodiments of the invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The pharmaceutical composition described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

The pharmaceutical composition of some embodiments of the invention may also be formulated in rectal compositions such as suppositories or retention enemas, using, e.g., conventional suppository bases such as cocoa butter or other glycerides.

Pharmaceutical compositions suitable for use in context of some embodiments of the invention include compositions wherein the active ingredients are contained in an amount effective to achieve the intended purpose. More specifically, a therapeutically effective amount means an amount of active ingredients (e.g. at least one of intracellular CELA3A, CELA1, and/or Cathepsin C downregulating or inhibiting agent) effective to prevent, alleviate or ameliorate symptoms of a disorder (e.g., cell necrosis) or prolong the survival of the subject being treated.

According to an embodiment of the present invention, an effect amount of the agent of the present invention, is an amount selected to cause conversion of cell necrosis to cell apoptosis.

The term "cell apoptosis" as used herein refers to the cell process of programmed cell death. Apoptosis characterized by distinct morphologic alterations in the cytoplasm and nucleus, chromatin cleavage at regularly spaced sites, and endonucleolytic cleavage of genomic DNA at internucleosomal sites. These changes include blebbing, cell shrinkage, nuclear fragmentation, chromatin condensation, and chromosomal DNA fragmentation. However, unlike necrosis, apoptosis produces cell fragments called apoptotic bodies that phagocytic cells are able to engulf and quickly remove before the contents of the cell can spill out onto surrounding cells and cause damage.

Determination of a therapeutically effective amount is well within the capability of those skilled in the art, especially in light of the detailed disclosure provided herein.

For any preparation used in the methods of the invention, the therapeutically effective amount or dose can be estimated initially from in vitro and cell culture assays (see e.g. Examples 1-3 in the Examples section which follows). Furthermore, a dose can be formulated in animal models to achieve a desired concentration or titer. Such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1).

Animal models for necrotic diseases and conditions include the porcine model for aseptic necrosis [see e.g. Müller-Vahl H and Pabst R., it J Tissue React. (1984) 6(3):251-4], the sheep model for femoral head necrosis [see e.g. J. Manggold et al., Laboratory Animals (2002) 36, 173-180].

Dosage amount and interval may be adjusted individually to provide the active ingredient at a sufficient amount to induce or suppress the biological effect (minimal effective concentration, MEC). The MEC will vary for each preparation, but can be estimated from in vitro data. Dosages necessary to achieve the MEC will depend on individual characteristics and route of administration. Detection assays can be used to determine plasma concentrations.

Depending on the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

Compositions of some embodiments of the invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition, as is further detailed above.

The agents of the invention can be suitably formulated as pharmaceutical compositions which can be suitably packaged as an article of manufacture. Such an article of manufacture comprises a label for use in treating a necrosis related disease, the packaging material packaging a pharmaceutically effective amount of the downregulating agent.

It will be appreciated that each of the agents or compositions of the present invention may be administered in combination with other known treatments, including but not limited to, anti-apoptotic agents or anti-inflammatory agents.

The agents or compositions of the present invention may be administered prior to, concomitantly with or following administration of the latter.

Anti-apoptotic agents which may be used according to the present teachings include, but are not limited to, —[R]—N-[2-heptyl]-methylpropargylamine (R-2HMP), vitamin E, vitamin D, caspase inhibitors and the hydrophilic bile salt ursodeoxycholic acid.

Anti-inflammatory agents which may be used according to the present teachings include, but are not limited to, Alclofenac; Alclometasone Dipropionate; Algestone Acetonide; Alpha Amylase; Amcinafal; Amcinafide; Amfenac Sodium; Amiprilose Hydrochloride; Anakinra; Anirolac; Anitrazafen; Apazone; Balsalazide Disodium; Bendazac; Benoxaprofen; Benzydamine Hydrochloride; Bromelains; Broperamole; Budesonide; Carprofen; Cicloprofen; Cintazone; Cliprofen; Clobetasol Propionate; Clobetasone Butyrate; Clopirac; Cloticasone Propionate; Cormethasone Acetate; Cortodoxone; Deflazacort; Desonide; Desoximetasone; Dexamethasone Dipropionate; Diclofenac Potassium; Diclofenac Sodium; Diflorasone Diacetate; Diflumidone Sodium; Diflunisal; Difluprednate; Diftalone; Dimethyl Sulfoxide; Drocinonide; Endrysone; Enlimomab; Enolicam Sodium; Epirizole; Etodolac; Etofenamate; Felbinac; Fenamole; Fenbufen; Fenclofenac; Fenclorac; Fendosal; Fenpipalone; Fentiazac; Flazalone; Fluazacort; Flufenamic Acid; Flumizole; Flunisolide Acetate; Flunixin; Flunixin Meglumine; Fluocortin Butyl; Fluorometholone Acetate; Fluquazone; Flurbiprofen; Fluretofen; Fluticasone Propionate; Furaprofen; Furobufen; Halcinonide; Halobetasol Propionate; Halopredone Acetate; Ibufenac; Ibuprofen; Ibuprofen Aluminum; Ibuprofen Piconol; Ilonidap; Indomethacin; Indomethacin Sodium; Indoprofen; Indoxole; Intrazole; Isoflupredone Acetate; Isoxepac; Isoxicam; Ketoprofen; Lofemizole Hydrochloride; Lomoxicam; Loteprednol Etabonate; Meclofenamate Sodium; Meclofenamic Acid; Meclorisone Dibutyrate; Mefenamic Acid; Mesalamine; Meseclazone; Methylprednisolone Suleptanate; Momiflumate; Nabumetone; Naproxen; Naproxen Sodium; Naproxol; Nimazone; Olsalazine Sodium; Orgotein; Orpanoxin; Oxaprozin; Oxyphenbutazone; Paranyline Hydrochloride; Pentosan Polysulfate Sodium; Phenbutazone Sodium Glycerate; Pirfenidone; Piroxicam; Piroxicam Cinnamate; Piroxicam Olamine; Pirprofen; Prednazate; Prifelone; Prodolic Acid; Proquazone; Proxazole; Proxazole Citrate; Rimexolone; Romazarit; Salcolex; Salnacedin; Salsalate; Sanguinarium Chloride; Seclazone; Sermetacin; Sudoxicam; Sulindac; Suprofen; Talmetacin; Talniflumate; Talosalate; Tebufelone; Tenidap; Tenidap Sodium; Tenoxicam; Tesicam; Tesimide; Tetrydamine; Tiopinac; Tixocortol Pivalate; Tolmetin; Tolmetin Sodium; Triclonide; Triflumidate; Zidometacin; Zomepirac Sodium.

In order to test treatment efficacy, the subject may be evaluated by physical examination as well as using any method known in the art for evaluating cell necrosis. Thus, for example, a necrotic cell or tissue sample may be obtained (e.g. from a subject) and necrotic cells can be identified, by light, fluorescence or electron microscopy techniques, or via staining with trypan blue, whereby the necrotic cells take up the dye and, thus, are stained blue. Necrotic cells can be distinguished from healthy cells via morphological changes including loss of membrane integrity, disintegration of organelles and/or flocculation of chromatin.

According to another aspect of the present invention, there is provided a method of treating and/or preventing aging in a subject in need thereof, the method comprising: (a) administering to the subject an agent which specifically downregulates an expression and alternatively or additionally inhibits an activity of a Cathepsin C, a CELA3A or structurally similar enzyme and a CELA1 in a cell of the subject; and (b) administering to the subject an anti-aging agent, thereby treating and/or preventing aging.

According to the present teachings any anti-aging agents may be used, as for example, an antioxidant, a phytochemical, a hormone and a fatty acid.

Exemplary anti-aging agents which may be used in accordance with the present teachings include, but are not limited to, Vitamin E, Vitamin C, Co-enzyme Q10, Lipoic acid, Folic acid, Selenium, Flavonoids, carotenes, Vitamin B and Carnitin.

Molecules which can be used along with the present teachings can be qualified for their specificity as follows.

Thus, according to another aspect of the present invention, there is provided a method of identifying an agent capable of inhibiting necrosis of a cell, the method comprising introducing into a cell that is subjected to a necrotic signal a test agent and identifying if the test agent specifically downregulates an expression and alternatively or additionally inhibits an activity of at least one of intracellular CELA3A, CELA1, and/or Cathepsin C, thereby identifying an agent capable of inhibiting necrosis of the cell. The test agent is tested for specificity by testing its effect on other cellular proteins such as other CELA proteins or proteins in the pathway (as further defined hereinabove, under "specificity").

In additional preferred embodiments, the invention provides specific small inhibitory molecules for use for prevention and treatment of necrosis and associated diseases and condition. The list of molecules includes small inhibitory compounds that belong to various chemical families, for example, to 2-aminoimidazolines, aminothiazoles and isoxazoles. The present invention also provides a variety of small molecule inhibitors for use in the treatment and/or prevention of a disease or a medical condition associated with cell necrosis. In yet further embodiment provided a use of small molecule inhibitor in the manufacture of a medicament for the treatment and/or prevention of a disease or a medical condition associated with cell necrosis.

Thus, according to one embodiment the test agent may be a small molecule or a natural inhibitor of elastases (e.g. indole-3-carbinol or Flavanol (–)epigallocatechin-3-gallate) and its specific inhibition of CELA1 or CELA3 may be evaluated using the present teachings. After the test agent is validated as a specific CELA1/CELA3A inhibitor it is further analyzed for inhibition of cell necrosis. A list of such molecules is presented in table 1.

For example, the small molecules of the present invention may comprise transition state analogues (i.e. chemical compounds with a chemical structure that resembles the transition state of a substrate molecule in an enzyme-catalyzed chemical reaction, however, they typically do not undergo a chemical reaction and act as enzyme inhibitors), reversible inhibitors (i.e. inhibitors which typically bind non-covalently to the enzyme, the enzyme-substrate complex, or both) and irreversible inhibitors (i.e. inhibitors which typically react with the enzyme and change it chemically, e.g. via covalent bond formation, and modify key amino acid residues needed for enzymatic activity).

With respect to any of the compounds as herein described this invention also contemplates any isomer, pharmaceutically acceptable salt, pharmaceutical product, hydrate, N-oxide, crystal or any combination thereof and the same is to be considered as part of this invention.

According to one embodiment the test agent may be a high affinity binding molecule or a polynucleotide and its specific inhibition of Cathepsin C, CELA1, CELA3A or a structurally related enzyme thereto may be evaluated using the present teachings. After the test agent is validated as a specific inhibitor, it is further analyzed for inhibition of cell necrosis.

Thus, according to some embodiments of the present invention, provided a cell-permeable protease inhibitor for use in the treatment and/or prevention of a disease or a medical condition associated with cell necrosis. The protease inhibitor inhibits an enzymatic activity of at least one intracellular protease involved in necrotic cell death in cells undergoing necrosis. The intracellular protease is selected from the group consisting of CELA3A, CELA1, and Cathepsin C. In preferred embodiments, the protease is CELA3A.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals there between.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions, illustrate the invention in a non-limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Maryland (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, C T (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., Eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, C A (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

General Materials and Experimental Procedures

Models of In-Vitro Necrosis
KCN-Induced Necrosis
Human promonocytic U-937 cells (p53-negative promonocytic cell line) were propagated in suspension in RPMI-1640 medium supplemented with 10% heat-inactivated fetal bovine serum, 2 mM glutamine, 100 U/ml penicillin and 100 µg/ml streptomycin. The cells in logarithmic phase were seeded at a concentration of $4 \times 10^5$/ml (Tsesin N, et al. Chemistry and Physics of Lipids, 2014, 183:159-168).

The rat pheochromocytoma PC12 cell line was propagated in DMEM medium (Beit Haemek, Israel), supplemented with 5% heat-inactivated calf serum, 10% heat-inactivated horse serum, 2 mM L-glutamine, 100 U/ml penicillin and 100 µg/ml streptomycin. PC12 cells in logarithmic phase were seeded at a concentration of $1.2 \times 10^5$/well in 96-well plates and incubated overnight.

Thereafter, the cells were washed twice and maintained in RPMI-1640 (U-937cells) and DMEM (PC-12 cells) glucose-free medium, supplemented with 2 mM pyruvate and 10% dialyzed FCS for one hour. Then cells were treated with or without KCN (Merck, Germany) at the indicated concentrations for 7 hours (U-937 cells), or for 5 hours (PC12 cells).

Testing of Inhibitors
Elastase inhibitors II (MeOSuc-AAPA-CMK) and elastase inhibitor III (MeOSuc-AAPV-CMK) were purchased from Calbiochem-Novabiochem, USA. Compound Gly-Phe diazomethylketone was purchased from MP Biomedicals, USA. All the compounds disclosed in Table 1 hereinabove were purchased from ChemDiv, San Diego, CA. The compounds were dissolved in DMSO and were administered 30 min before addition of the cell death inducer. The final concentration of DMSO, added to all samples, was 0.1%, which had no effect by itself siRNA and cell transfection Cells were treated for 48 hours with a complex of HiPerFect Transfection Reagent with siRNA aimed to inhibit the specific proteases or with appropriate controls as follows. HiPerFect Transfection Reagent is a blend of cationic and neutral lipids that enables effective siRNA uptake and efficient release of siRNA inside cells, resulting in perfect gene knockdown. Negative and positive death controls were used according to manufacture instructions. The siRNA sequence for Cathepsin C silencing was ATGATCTGCATCAGTTGTAAA (SEQ ID NO: 1). The siRNA sequence for CELA1 was CGGCAACATGCTGGTCCTTTA (SEQ ID NO: 2) and the siRNA sequence for CELA3A was CTGCCTTTGGCTGCAACTTCA (SEQ ID NO: 3). The siRNA sequence used for the control was AAT-TCTCCGAACGTGTCACGT (SEQ ID NO: 4). All siRNAs and HiPerFect™ Transfection Reagent were purchased from Qiagen.

Thereafter, normal or silenced cells were washed twice and transferred to glucose-free medium for an hour and then necrosis was induced with potassium cyanide as described above. The cell death rate was assessed by Promega's CytoTox 96® Non-Radioactive Cytotoxicity Assay, which accurately and rapidly measures cell death by quantifying the release of lactate dehydrogenase (LDH), a stable cytosolic enzyme from lysed cells.

The CELA1 siRNA sequence matches the CELA1 transcript perfectly, but it also matches imperfectly CELA3A and CELA3B. The CELA3A siRNA matches CELA3A perfectly.

Morphological Quantification of Necrosis and Apoptosis
Cells undergoing morphological changes associated with apoptotic or necrotic cell death were monitored as previously described [McGahon A J et al., Methods Cell Biol (1995) 46:153-184] and [Zelig U et al., Biophys J. 2009 Oct. 7; 97(7):2107-14.]. At the given time point after treatment, 1 ml of cell suspension was collected, centrifuged and a pellet was resuspended in 20 fold dilution of the dye mixture (composed of 100 µg/ml acridine orange and 100 µg/ml ethidium bromide) in PBS and placed on a glass slide to be viewed on a fluorescence microscope. Cells were scored as alive if nuclei exhibited normal morphology and were green. Cells exhibiting normal morphology and orange color were scored as necrotic. Cells were scored as apoptotic if their nuclei exhibited chromatin condensation and/or nuclear fragmentation. A minimum of 100 cells was scored for each sample.

Assay of Necrosis Using Lactate Dehydrogenase (LDH) Release

The amount of LDH released from lysed cells is a sensitive measure of cell death. Necrotic cell death was measured in 96-well plates using Promega CytoTox 96 LDH assay kit. LDH content from the cells lysed in 0.1% Triton X-100 for 10 min was used as an index of total LDH. The LDH released in culture medium was used as an index of necrotic cell death and the percentage from total LDH was calculated. The protection by the inhibitor was calculated based on comparing percentage of LDH release in the presence and in the absence of the inhibitor. The inhibitors were also added to totals, blanks and controls. Absorbance at 490 nm was measured by ELISA reader (BioTec).

Assays of Elastase and Cathepsin C Activity

Cells were collected, washed twice with ice-cold PBS and resuspended at $2 \times 10^8$/ml in ice-cold lysing buffer (50 mM Tris-HCl pH 7.5, 0.1% NP-40, 1 mM DTT). The cells were broken by polytron (3 cycles of 7 sec each) and the debris was pelletized by centrifugation at 13,000 g for 30 min, at 4° C. The supernatant was used immediately. Protein content of each sample was determined using the Bradford Protein Assay (Bio-Rad) using bovine serum albumin (BSA) as standard. All assays were set up at a total volume of 100 μl and contained N-methoxysuccinyl-Ala-Ala-Pro-Val p-nitroanilide (MAAPV) (Sigma) as elastase substrate, at final concentration of 5 mM, 40 g sample proteins in the presence or absence of specified concentration of protease inhibitor or solvent for control in triplicates in flat-bottomed microtiter plates. After incubation for 1.5 hour at 37° C., the OD at 405 nm was measured with a plate ELISA reader (Molecular Devices). The protease activity was calculated according to the calibration curve of p-nitroaniline. Cathepsin C like activity was measured similarly with Gly-Phe p-nitroanilide (Sigma).

Traumatic Brain Injury In-Vivo Model

The closed head injury method was used to determine the effect of the elastase inhibitor on the development of brain necrosis and on the neurological status assessed using the neurological severity score (NSS). NSS test was performed 1 hour after trauma. During NSS test, various reflexes, ability to move, beam balance, beam walk and other behavior parameters like seeking and exiting from a cycle were monitored. Development of necrosis was measured by assessing necrotic space in brain slices stained with 2,3,5-triphenyl-2H-tetrazolium chloride (TTC).

C57BL/6J mice weighing 40+4 g (mean±SD) were used in the study. A weight-drop device was used to deliver a shock to the scull resulting in a controlled cerebral injury. Impact was delivered by a silicone-coated 5 mm metal tip extruding from a platform that falls down a frame. This model of cranial injury has been used in previous studies [Feldman Z et al., J Neurosurg (1995) 83:1060-1066; Shapira Y et al., J Neurosurg Anesthesiol (1995) 7:17-25].). All animal procedures and care techniques approved by the Ben-Gurion University of the Negev Committee for the Ethical Care and Use of Animals in Research.

Mice were prepared for surgery by anesthetization with isoflurane and allowed to breathe spontaneously. Maintenance of adequate anesthesia for the experimental procedure was confirmed by loss of corneal reflexes. Once the corneal reflexes were abolished, a midline scalp incision was made and the scalp and underlying muscles were moved laterally. Closed head trauma (CHT) was delivered to the skull over the frontal portion of the left cerebral hemisphere. 1 minute after the trauma 100 μg of elastase inhibitor II or III in its vehicle (DMSO solution), were injected intracerebraspinaly by direct delivery into the cisterna magna. The vehicle itself was previously found to have no effect. Mice that were not traumatized had a NSS of 0 to 1 and no necrotic spaces on the stained brain slices.

After the injection anesthesia was discontinued, animals were returned to their cages, and food and water were supplied ad libitum.

In addition to the wild type C57BL/6J mice, neutrophil elastase knockout mice strain B6.129X1-Elane were also examined. All procedures were approved by the Ethics Committee of Ben-Gurion University of Negev.

Liver Toxicity In Vivo Model

Wild type C57BL/6J mice weighing 23+3 grams were used, 6 mice per treatment. The mice were obtained from Harlan (Israel). All animal procedures and care techniques were approved by the Ben-Gurion University of the Negev Committee for the Ethical Care and Use of Animals in Research. Mice were fast for 16h prior to administration of a single intraperitoneal (i. p.) dose of acetaminophen (N-acetyl-p-aminophenol) APAP (300 mg/kg). 4 hours after the APAP injection, the mice were injected i. p. with the tested compound, dissolved in vehicle (20% DMSO in PBS). The control mice were injected with the vehicle only. 24h after APAP injection, the mice were sacrificed and blood collected from the heart. Heparin was used as an anti-clotting additive for plasma collection. The plasma samples were centrifuged at 4000 g at room temperature for 10 min. The supernatant was collected for measurement of ALT and AST levels. The enzyme levels were measured with an autoanalyzer in Soroka's Biochemistry Medical Center.

Heart Necrosis In Vivo Model

Male Balb/c mice (20-25 g; Charles River; Milan; Italy) were housed in a controlled environment and provided with standard rodent chow and water.

Mice were subjected to 30 minutes of myocardial ischemia and 6 hours of reperfusion, using published methodologies (Yet et al, 2001). Study groups consisted of sham, vehicle control, and inhibitor (n=8/group, see below). Briefly, mice were anesthetized with pentobarbital sodium (60 mg/kg body weight) with additional doses given as needed to maintain anesthesia. Mice were intubated and mechanically ventilated with 100% oxygen. Mice received a first IV dose of the active inhibitor 1-(2-(4-methylpiperazin-1-yl)-4,5-dihydro-1H-imidazol-1-yl)propan-1-one (M059-0891) (30 mg/kg) and their chest was opened. 20 min after inhibitor IV administration, ischemia was initiated by ligating the left anterior descending coronary artery (LAD) using an 8-0 silk suture with a section of PE-10 tubing placed over the LAD, 1 mm from the tip of the normally positioned left atrium. After occlusion for 30 minutes, reperfusion was initiated by releasing the ligature and removing the PE-10 tubing. Animals received a second IV dose of the inhibitor (30 mg/kg,) at the onset of reperfusion. The chest wall was then closed, the animal extubated, and body temperature maintained by use of a 37° C. warm plate. After 6 hours of reperfusion, animals were euthanized for collection of hearts for determination of morphologic injury. The area of necrosis, as a % of AAR was quantified.

Experimental groups: A total of 24 mice were allocated to the following groups:

Ischemia/reperfusion+vehicle: mice subjected to LAD occlusion (30 min) followed by reperfusion (6 hours) (n=8);

Ischemia/reperfusion+Compound: mice subjected to surgical procedures described as above and treated with Elastase Inhibitor 20 minutes prior to ischemia initiation and at the onset of reperfusion (Dose 30 mg/kg via IV bolus) (n=8);

Sham+vehicle: mice subjected to identical surgical procedures except for LAD occlusion and kept under anesthesia for the duration of the experiment (n=8);

At the end of all experiments, animals were treated as described below for assessment of infarct region.

Determination of Infarct Size.

After the reperfusion period, 1 mL/kg of a 4% thioflavin S solution is injected IV in order to delineate the no-reflow area. Thioflavin S solution is a fluorescent yellow-green dye that stains the perfused areas as fluorescent, whereas the no-reflow area appears dark. 5 min later, the LAD is re-occluded and 0.6 mL of 50% Unisperse blue (Ciba Geigy, Hawthorne, NY) is given by IV injection in order to delineate the AAR (tissue lacking the blue dye), and the mice are euthanized with 1 mL KCl (150 mg/mL IV) under deep anesthesia. The heart is then excised and the LV cut into 4 equally thick transverse slices. These slices are photographed using an ultraviolet light ($\lambda$=254 nm) and a yellow filter in order to determine the no-reflow zone (dark area) and then under halogen lighting to identify the AAR (not stained blue). The slices are then incubated in 1% triphenyltetrazolium chloride (TTC) for 15 min at 37° C. in order to delineate the infarcted zone. TTC stains viable myocardial tissue brick red and infarcted tissue appears white. The ventricular slices are then rephotographed. Digital photographs of the heart slices showing no-reflow zone, AAR, and necrotic zone are traced and then digitized using a computerized planimetric system. The areas of ischemic and nonischemic regions are computed and expressed as a percentage of the slice, as are the % of necrotic and non-necrotic tissue. The % in each slice is then multiplied by the weight of the slice. The weights are summed for each heart. AAR (unstained blue area) is expressed as a percentage of the LV mass. The extent of necrosis is calculated as a percentage of the LV mass, and the infarct size expressed as a percentage of the AAR (infarct size=extent of necrosis/extent of AAR).

Data Analysis

All values in the figures and text were expressed as mean standard error of the mean (SEM) of N observations. The data was analyzed by one-way ANOVA followed by a Bonferroni post-hoc test for multiple comparisons. Non-parametric data was analyzed with the Fisher's exact test. A p-value less than 0.05 is considered significant. *p<0.05 vs. Sham. *p<0.05 vs I/R Statistical Analysis Unless specified otherwise, each experiment was performed 3 times; each sample was tested in at least in duplicates. The results demonstrate mean±SE. Statistical analysis was performed using a Student's T-test. Values of NSS are analyzed with the non-parametric Mann-Whitney test using SPSS for Microsoft Windows® software. Significance was set at P<0.05.

Example 1

Necrosis is Accompanied by Induction of Intracellular Elastase-Like Proteolytic Activity The first experiment was carried out to determine whether necrosis is accompanied by induction of intracellular proteolytic activity. Necrosis in U-937 cells was induced by treatment with KCN, which kills cells by causing chemohypoxia. Dose and time dependent kinetics of KCN-induced necrosis in U-937 cells are shown in FIG. 1.

To further corroborate that activation of elastase-like proteolytic activity occurs during the necrotic cell death process, the activity thereof was determined in cell extracts prepared from KCN-treated U-937 cells as compared to controls, using MAAPV, an elastase specific substrate. In order to see at what stage of necrosis the elastase-like enzyme was activated, the enzymatic assay was performed in lysates prepared from U937 cells treated with KCN for different time intervals. FIG. 2 shows the time dependent induction of proteolytic activity induced by treatment with 10 mM KCN. As can be seen, elastase like activity was also elevated dramatically within 10 minutes and reached its maximum within 15 minutes when its activity was elevated by 7 fold. The increase of elastase activity was detected before morphological signs of cell death could be observed.

The elastase-like induced activity was further characterized using different protease inhibitors. EI III at 100 µM concentration had a slight effect on elastase activity of control cells; however, it completely inhibited the necrosis-induced activity. The inhibition was dose-dependent, with IC50 2.735 µM (FIG. 3). These results indicated that the induced proteolytic activity associated with necrosis in U-937 cells is compatible with a serine protease activity.

The present inventors wanted also to see at what stage of necrosis Cathepsin C the elastases' activating enzyme was activated. For this purpose an enzymatic assay was performed in lysates of cells treated with KCN 10 mM for different time intervals. FIG. 2 which shows the time dependent induction of proteolytic activity induced by treatment with 10 mM KCN. As can be seen, already after 10 minutes of treatment, the Cathepsin C like activity was raised by 4 fold and reached its maximum.

The very large difference in the time scale of the induction of the elastase-like proteolytic activity (minutes, FIG. 2) and the progression of the necrotic process (hours, FIG. 1) led to the hypothesis that the proteolytic activity is part of the initial molecular steps of the necrotic pathway. In order to test this hypothesis, different methods were utilized for inhibition and down regulation of expression of the elastase-like enzymes and to examine their effect on the necrotic process (see Examples 2 and 3 herein below).

Example 2

Transfection with siRNAs for Cathepsin C, CELA3A and CELA1 Protects Against Necrosis Induced Cell Death In attempt to characterize the enzyme(s) that are activated at early stages of the necrotic process, the present inventors have utilized a library of siRNAs against different proteases. Transfections were performed with siRNAs against total of 93 proteases.

Figure 4A:
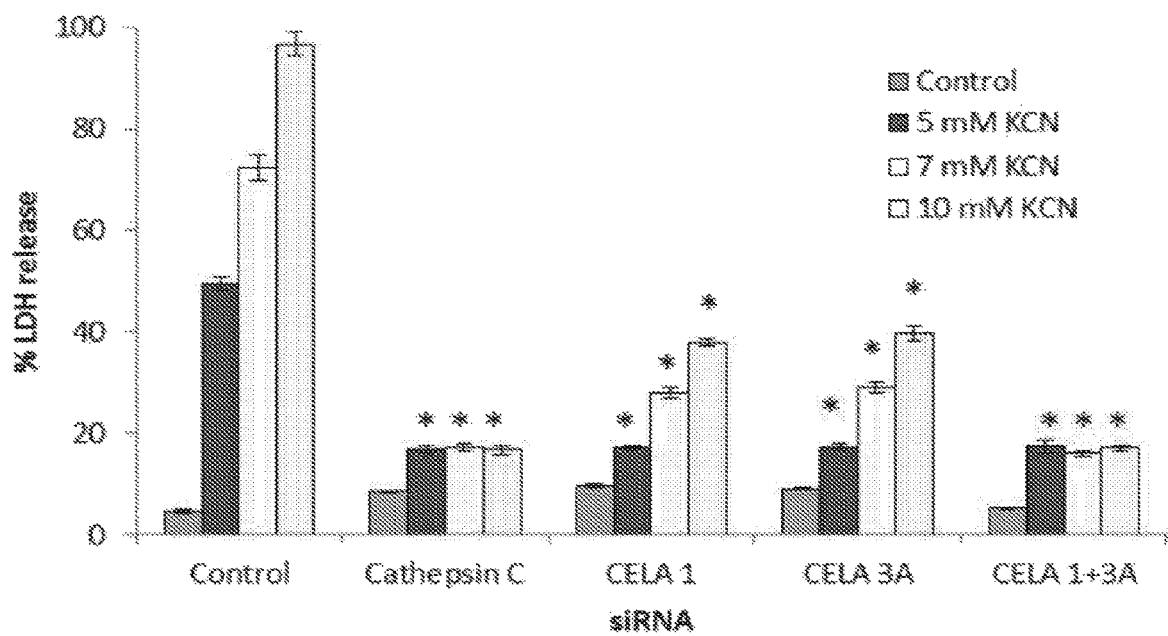
FIGS. 4A-B illustrate the effect of silencing by siRNAs for CELA1 and CELA3A on LDH release from U-937 cells undergoing necrosis induced by different concentrations of KCN.
Figure 4B:
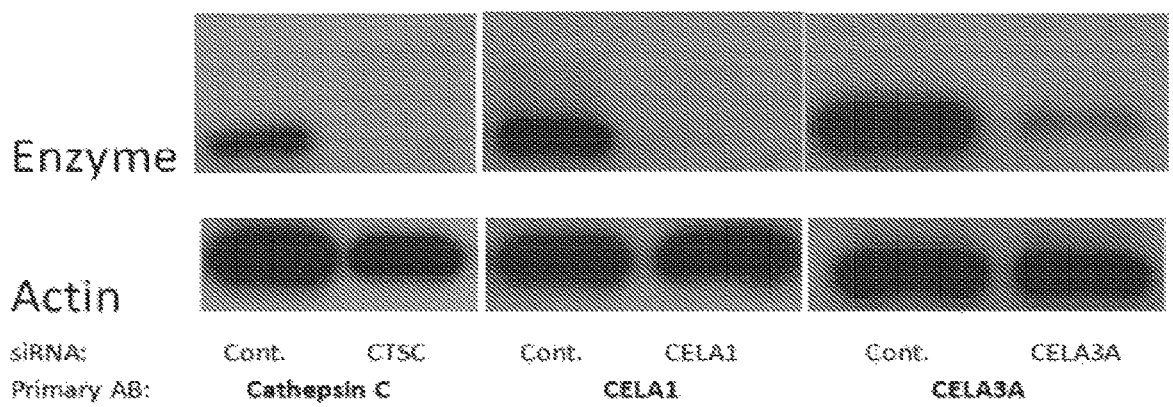

FIGS. 4A-B show that transfection of U-937 cells with siRNA of CELA1 or CELA3A led to a stable and significant decrease in the LDH release after 7 hours incubation with KCN. Transfection with either CELA1 or CELA3A alone caused partial protection, whereas transfection with a combination of siRNAs against both CELA1 and CELA3A provided full protection against necrosis.

In addition to siRNA for CELA1 and CELA3A, siRNAs for other proteases were tested. Among them were Cathepsins A, B, C, D, E, G, H, K, L1, L2, O, S, W and Z, serine proteases HNE, HtrA, chymotrypsin C, CELA 2A and CELA 3B, matrix metallopeptidases 7, 11, 12, 21 and 25. The results indicate that siRNA for Cathepsin C also exhibited protective effect against necrosis (FIG. 4A). Transfections with siRNAs against total of 90 proteases were unable to confer any protection against KCN induced cell death.

Figure 4C:
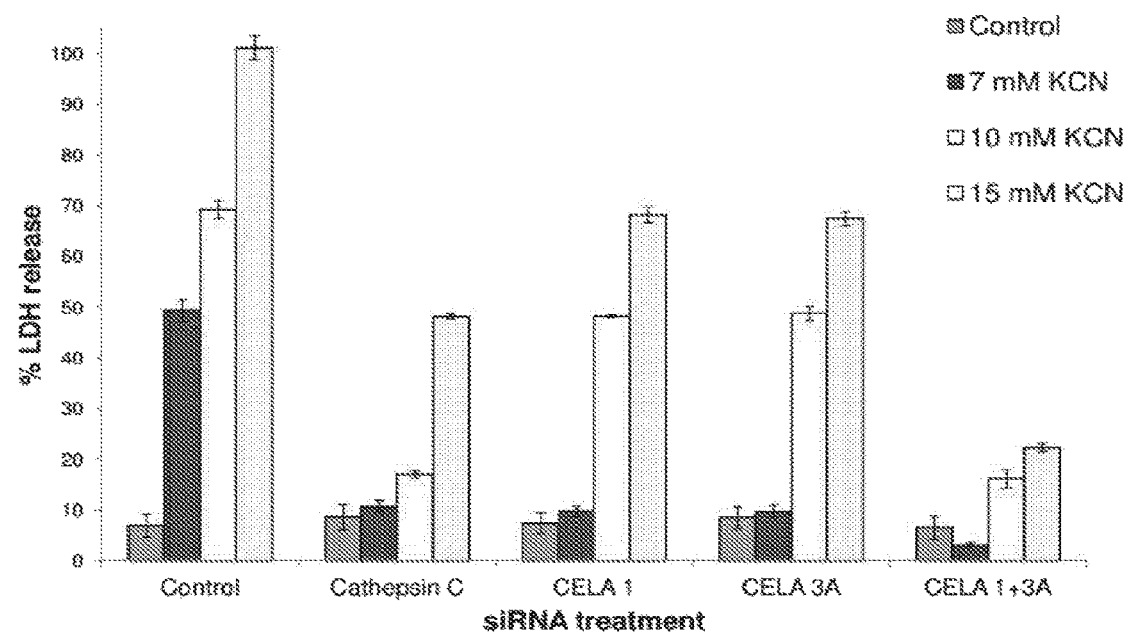
FIG. 4C illustrates the effect of silencing by siRNAs for Cathepsin C, CELA1 and CELA3A on LDH release from PC12 cells undergoing necrosis induced by KCN. PC12 cells transfected with control siRNA or siRNA for the specific enzymes were preincubated in glucose free medium for one hour and treated with or without KCN for 5 hours. Thereafter LDH release from the cells was determined. *P<0.001.

To be sure that the effect of specified siRNAs was not specific for U-937 cells, these experiments were repeated with PC12 cells (FIG. 4C).

The comparative experiment with PC12 cells showed that siRNA for Cathepsin C, CELA3A and CELA1 each had a significant protective effect on U-937 and PC12 cells against cyanide induced cell death. It also could be seen that the mixture of siRNA and HiPerFect Transfection Reagent (control treatment) was not toxic for the cells. Moreover the activation of Cathepsin C early during necrosis was shown as well as inhibition of necrosis by small molecule Cathepsin C inhibitor. The results also showed that inhibition of the activity of the above mentioned enzymes was associated with reduction in cell death. The results indicated that these enzymes may serve as targets for controlling/modulating necrotic cell death.

Example 3

Transfection with siRNA for Cathepsin C, CELA1 and/or CELA3A Lead to Specific Inhibition To be sure that the protective effect of specified siRNAs was due to shutdown of transcription of the target enzymes and not by any off-target effect, the present inventors have performed enzymatic assays to show that Cathepsin C and elastase-like activity were inhibited in the cells transfected with the specific siRNAs. For additional support of effective silencing, Western Blot analysis was carried out for the specified proteins and showed that the expression of the silenced enzyme was indeed inhibited.

Figure 5A:
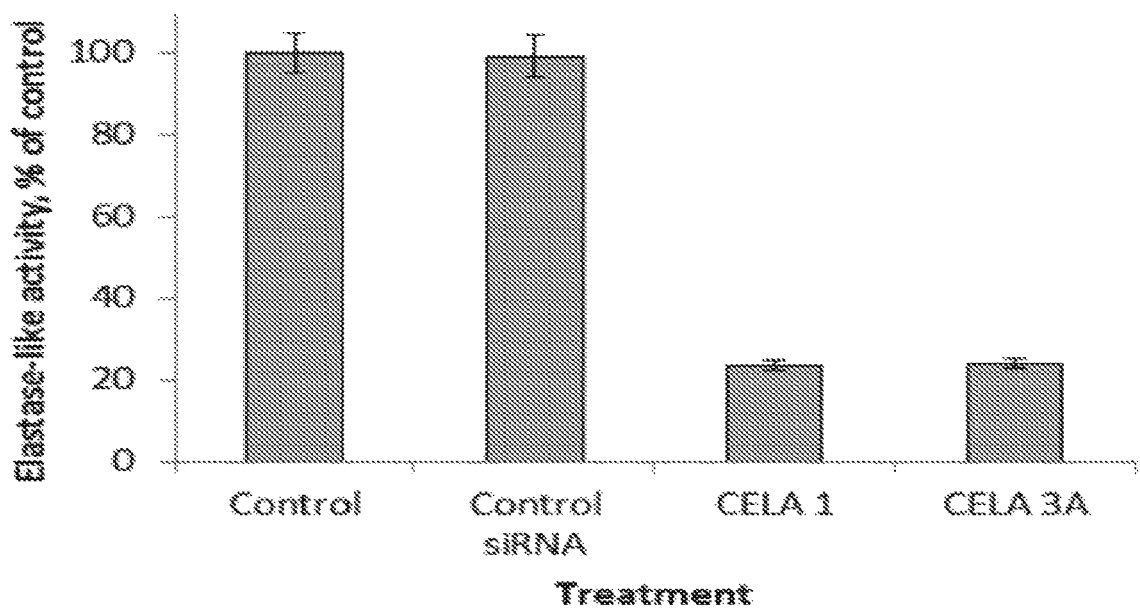
FIGS. 5A-B are bar graphs depicting the effect of siRNAs on elastase activity (FIG. 5A) and Cathepsin C activity (FIG. 5B). Cells treated by control siRNA or siRNA for Cathepsin C, CELA1 or CELA3A were exposed to KCN 10 mM for 30 minutes. The cells were then lysed and Cathepsin C or elastase-like activities in the lysates were measured with specific colorimetric substrates.
Figure 5B:
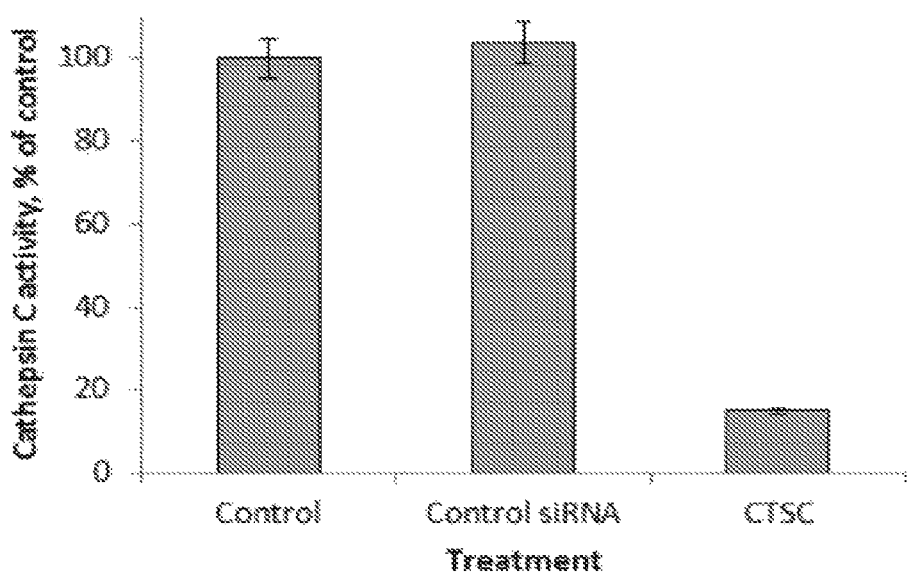

FIGS. 5A-B show that siRNAs for Cathepsin C, CELA1 and CELA3A caused a stable and significant decrease in the appropriate enzymatic activity of cell lysates. Moreover transfection with siRNA for elastases CELA1 and CELA3A had no effect on Cathepsin C activity further supporting the specificity of the effect. This experiment showed that the protective effect of the treatment with the specified siRNAs was attributed to downregulation of the enzymes and not any other non-target effect. These results further showed that Cathepsin C is essential for programmed necrotic cell death.

Moreover, the combined results of both FIG. 4A and FIGS. 5A-B indicated that under conditions in which the activity of these specific enzymes (CELA3A and CELA1) is inhibited (FIGS. 5A-B), the process of necrosis is inhibited (FIG. 4A), meaning that blocking the activity of these enzymes causes inhibition of cell death.

Thus, these studies provide a foundation for which enzymes represent effective targets for inhibition of necrosis. Taken together the results suggest that specific CELA3A and CELA1 inhibitors and not inhibitors of others elastases, are capable of inhibiting necrotic cell death.

Example 4

Figure 6:
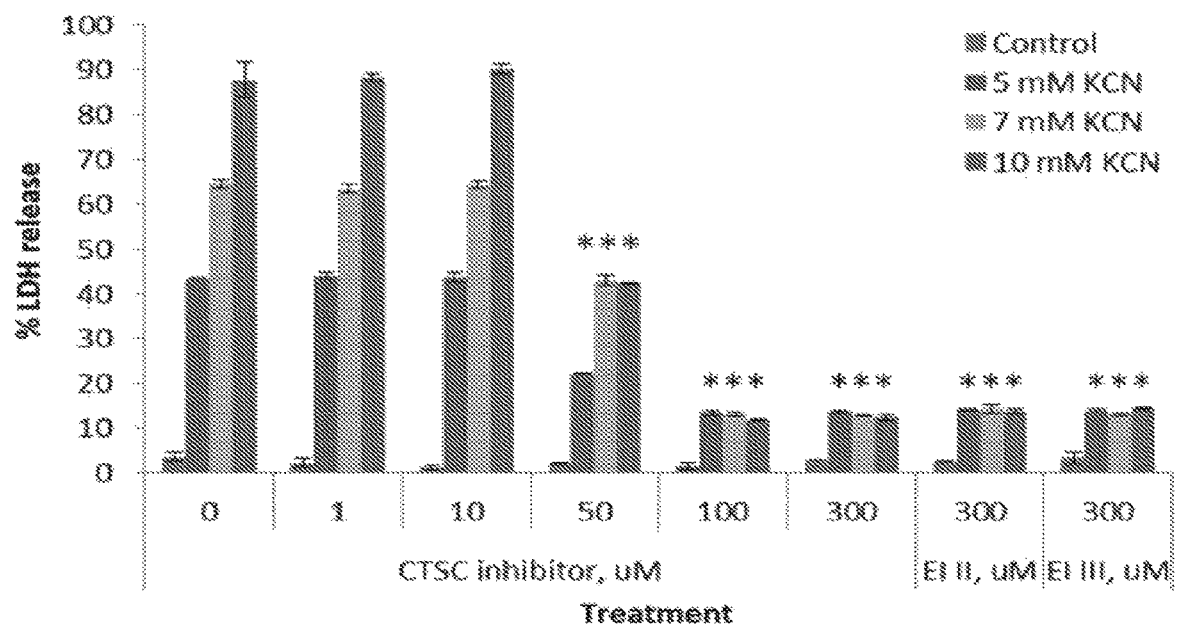
FIG. 6 shows the effect of a specific Cathepsin C inhibitor on LDH release from PC12 cells undergoing necrosis induced by KCN. Cells were treated with or without different concentrations of KCN for 5 hours in the presence or absence of different concentrations of Cathepsin C inhibitor and then LDH release from the cells was determined. Elastase inhibitors were used as positive controls. *P<0.01.

Cathepsin C, CELA3A and CELA1 Inhibitors Lead to Inhibition of Necrotic Cell Death FIG. 6 shows that Cathepsin C inhibitor (Gly-Phe-DMK, MP Biomedicals, USA) was able to inhibit necrosis induced by KCN in PC12. The addition of the inhibitor inhibited cell necrosis as manifested by reduction of LDH release in a dose dependent manner. Again, the results of FIGS. 5A-B and FIG. 6 implied that Cathepsin C could provide a target for anti-necrotic agents.

Figure 7A:
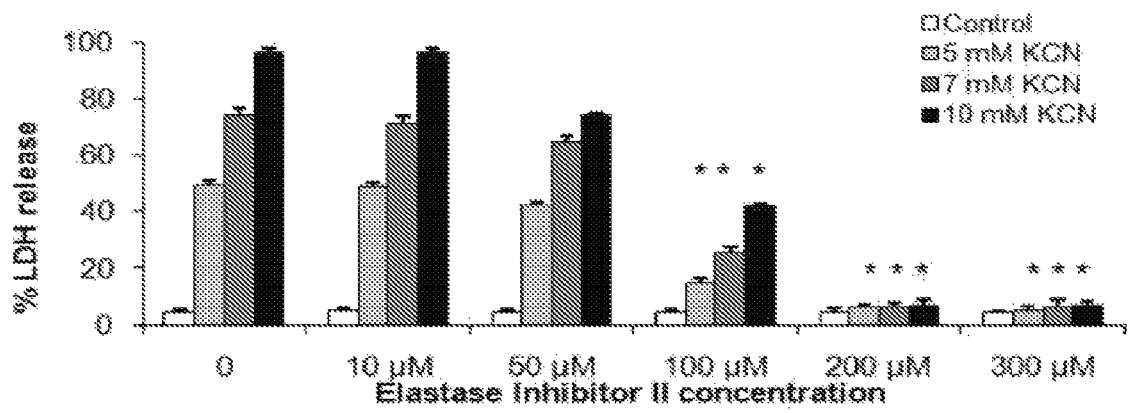
FIGS. 7A-B are bar graphs depicting the protective effect of different elastase inhibitors on PC12 cells undergoing necrosis.
Figure 7B:
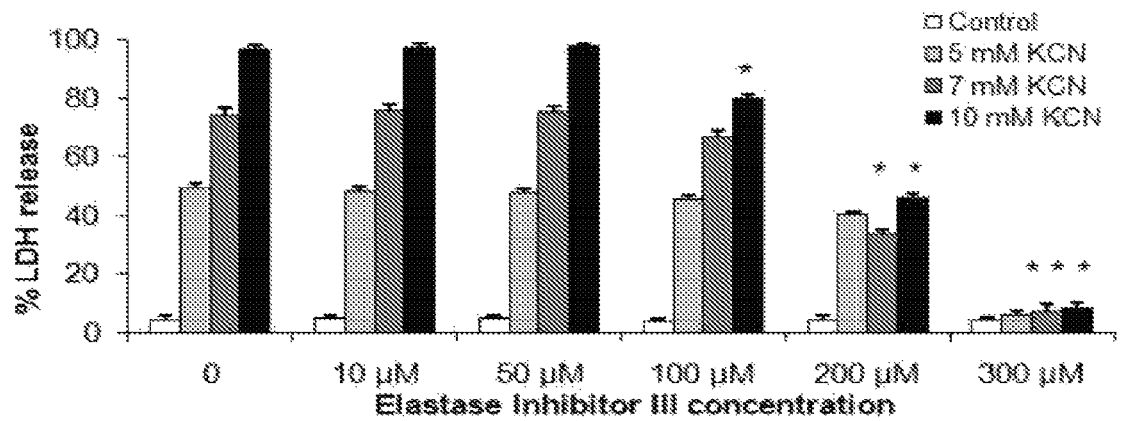

A direct consequence of the present hypothesis that links the elastase-like activity with the necrotic death pathway is that inhibition of this proteolytic activity will delay or prevent execution of the necrotic cell death program. To test this hypothesis the effect of permeable elastase inhibitors on necrotic cell death was studied. EI II and III inhibited in a dose dependent manner KCN-induced cell death in PC12 cells as assessed by LDH release (FIGS. 7A&B). The non-cell-permeable elastase inhibitor elastatinal had no protective effect on cells undergoing KCN-induced necrosis (data not shown).

CELA3A inhibitors were synthesized based on 3D structure similarities and topological analogy. These were tested for their ability to confer antinecrotic protection. Representative examples of some of the results are presented in Table 2. The protection against KCN induced necrosis was observed at various concentrations up to 0.1 nM (Table 2). Two small molecule inhibitors of CELA1 were able to inhibit necrosis as well, and certain compounds, for example the last three compounds listed in the table conferred protection at much higher concentrations.

TABLE 2

| Inhibits: | Structure | Compound Name | I.D. | % protection at indicated concentration | | | | |
|---|---|---|---|---|---|---|---|---|
| | | | | 1 μM | 100 nM | 10 nM | 1 nM | 0.1 nM |
| CELA 3 | 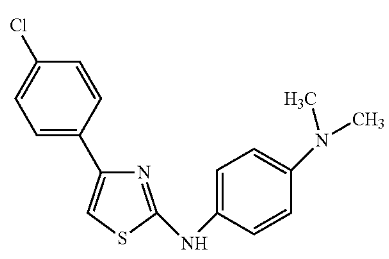 [SMILES: CN(C)c1ccc(Nc2nc(-c3ccc(Cl)cc3)cs2)cc1] | N'-[4-(4-chlorophenyl) thiazol-2-yl]- N,N-dimethyl-benzene- 1,4-diamine | 4112- 3656 | 77 | 73 | 55 | 25 | 30 |

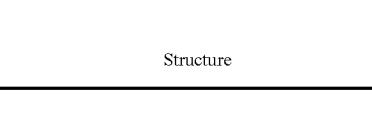

TABLE 2-continued

| Inhibits: | Structure | Compound Name | I.D. | % protection at indicated concentration | | | | |
|---|---|---|---|---|---|---|---|---|
| | | | | 1 μM | 100 nM | 10 nM | 1 nM | 0.1 nM |
| CELA 3 | | 2-(3-bromophenyl)-4-oxo-4H-3,1-benzoxazin-6-yl acetate | 4334-1600 | 74 | 70 | 28 | 30 | 28 |
| CELA 3 | | N-(4-methyl-2-pyridyl)-4-(2,4,5-trimethylphenyl)thiazol-2-amine | M008-0111 | 90 | 46 | 38 | 36 | 29 |
| CELA 3 | | 6-bromo-2-(3,5-dimethoxyphenyl)-3,1-benzoxazin-4-one | 3952-1000 | 77 | 35 | 38 | 33 | 35 |
| CELA 3 | | Cyclopentyl-(2-pyrrolidin-1-yl-4,5-dihydroimidazol-1-yl)methanone | M059-0082 | 85 | 79 | 51 | 25 | 33 |
| CELA 1 | 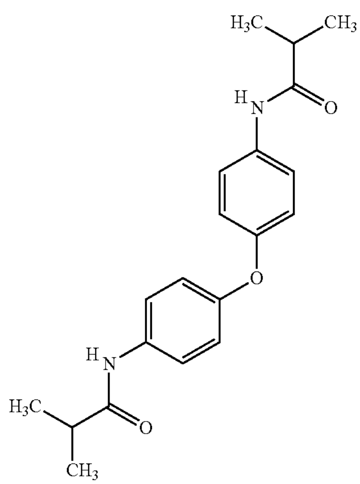 | N-[4-[4-(isobutyrylamino)phenoxy)phenyl]-2-methyl-propionamide | Y200-4083 | 74 | 49 | 32 | 25 | 11 |

TABLE 2-continued

| Inhibits: | Structure | Compound Name | I.D. | % protection at indicated concentration |||||
|---|---|---|---|---|---|---|---|---|
| | | | | 1 μM | 100 nM | 10 nM | 1 nM | 0.1 nM |
| CELA 1 | 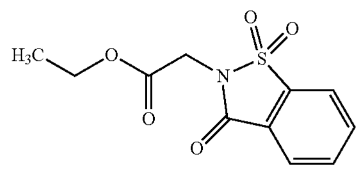 [SMILES: CCOC(=O)CN1C(=O)c2ccccc2S1(=O)=O] | Ethyl-2,3-dihydro-3-oxo-1,2-benzisothiazole-2-acetate-1,1-dioxide | 5149-0030 | 80 | 68 | 35 | 25 | 19 |
| CELA 3 | | (2-chlorophenyl)-[2-(1-piperidyl)-4,5-dihydroimidazol-1-yl] methanone | M059-0326 | 10 μM confers protection 56% of cells |||||
| CELA 3 | | (2-bromophenyl)-[2-(1-piperidyl)-4,5-dihydroimidazol-1-yl] methanone | M059-0193 | 10 μM confers protection 58% of cells |||||
| CELA 3 | | (2-fluorophenyl)-[2-(1-piperidyl)-4,5-dihydroimidazol-1-yl] methanone | M059-0216 | 10 μM confers protection 71% of cells |||||

It can be observed that exposure of PC-12 cells to high concentrations (up to 300 μM) of non-specific elastase inhibitor EI II and III, which were inactive by themselves, significantly inhibited necrosis induced by KCN. Yet, it can be equally readily seen that small-molecule CELA3A inhibitors were effective in concentrations lower by several orders of magnitude. The unexpected enhanced activity of CELA1- and CELA3A-specific inhibition in preventing/treating necrosis highlights the importance of these two unique targets and thereby targets structurally related thereto.

Example 5

Figure 7C:
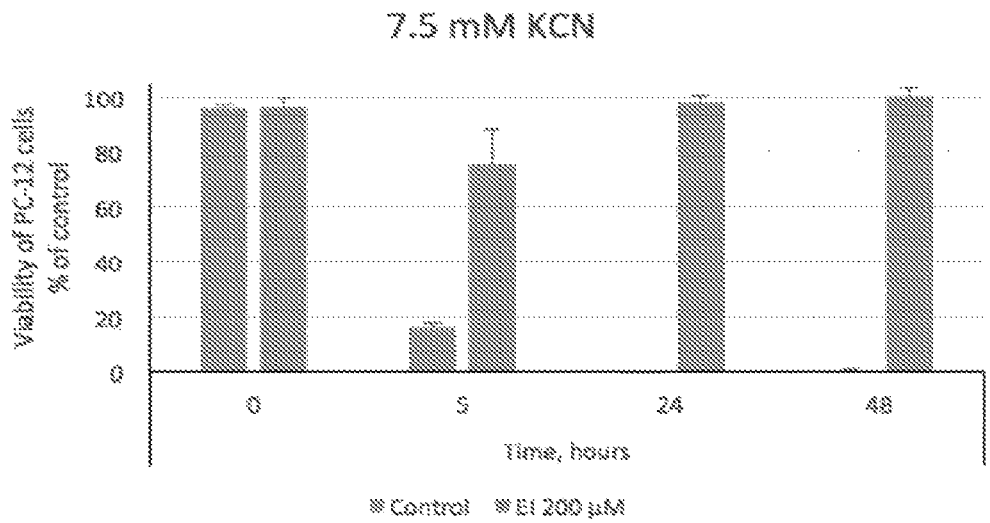
FIG. 7C is a bar graph depicting the protective effect of elastase inhibitor II in the rescue of KCN-treated cells up to 48 hours. The cells maintained in glucose deficient medium were incubated with or without elastase inhibitor II for 30 minutes. Then the cells were treated with or without KCN for 5 hours. Thereafter, the medium was changed to full DMEM and incubation proceeded for 24 or 48 hours. Elastase inhibitor itself had no effect on survival of control cells. The XTT method was used to measure cell viability at each specified time and the results were compared to their respective controls.

The Protective Effect of Elastase Inhibitors is Manifested in the Rescue of KCN-Treated Cells, Rather than Just Preventing their Membrane Rupture To examine whether the protective effect of elastase inhibitor on the cells is maintained for long time following the ischemic stress, we performed kinetic studies. Following the 5 h KCN incubation, the medium was changed to regular DMEM with no KCN or elastase inhibitors and incubation proceeded for up to 48 h. Cell survival was assessed by the XTT method, which measure cell metabolic activity rather than membrane integrity. The results indicate that the cells survived the 5 h KCN treatment without irreversible damage. They show full recovery 48 h post KCN treatment (FIG. 7C). These results are of clinical significance as they demonstrate that elastase inhibitors provide long lasting protective effect. For example, tissues treated with elastase inhibitor during the therapeutic window after ischemic stress like in MI or stroke could be saved.

Example 6

The Effect of Elastase Inhibitors on Necrosis In Vivo

Figure 8A:
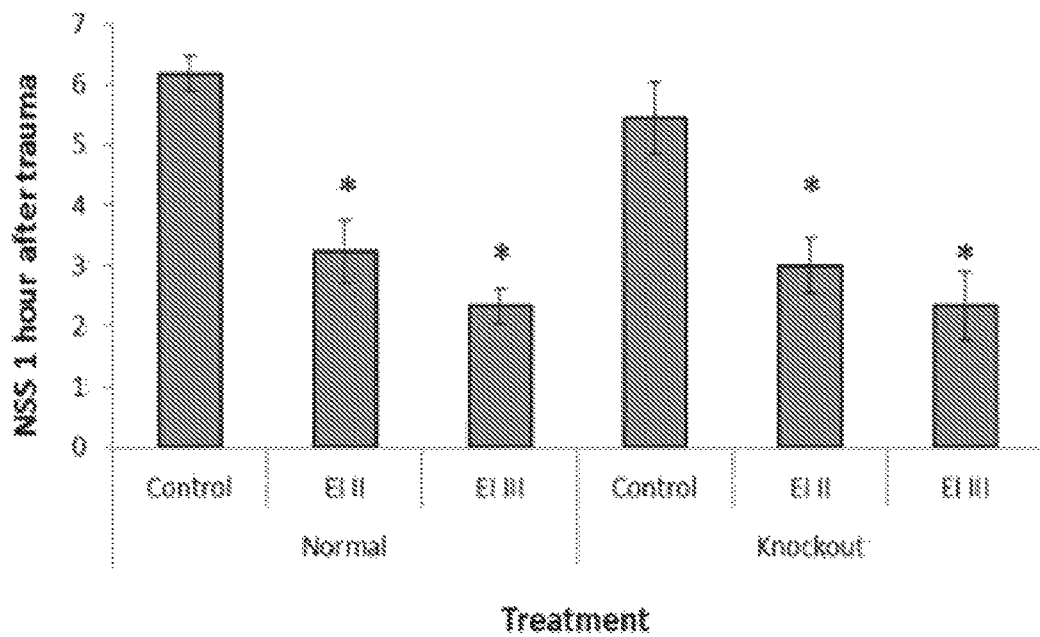
FIGS. 8A-B are bar graphs illustrating that elastase inhibitors II and III protect mouse brains from closed head injury in-vivo. Quantification of the effect of elastase inhibitors II and III on (FIG. 8A) neurological severity score (NSS) and on FIG. 8B, development of the necrotic area in brains of traumatized mice is shown. *P<0.01.
Figure 8B:
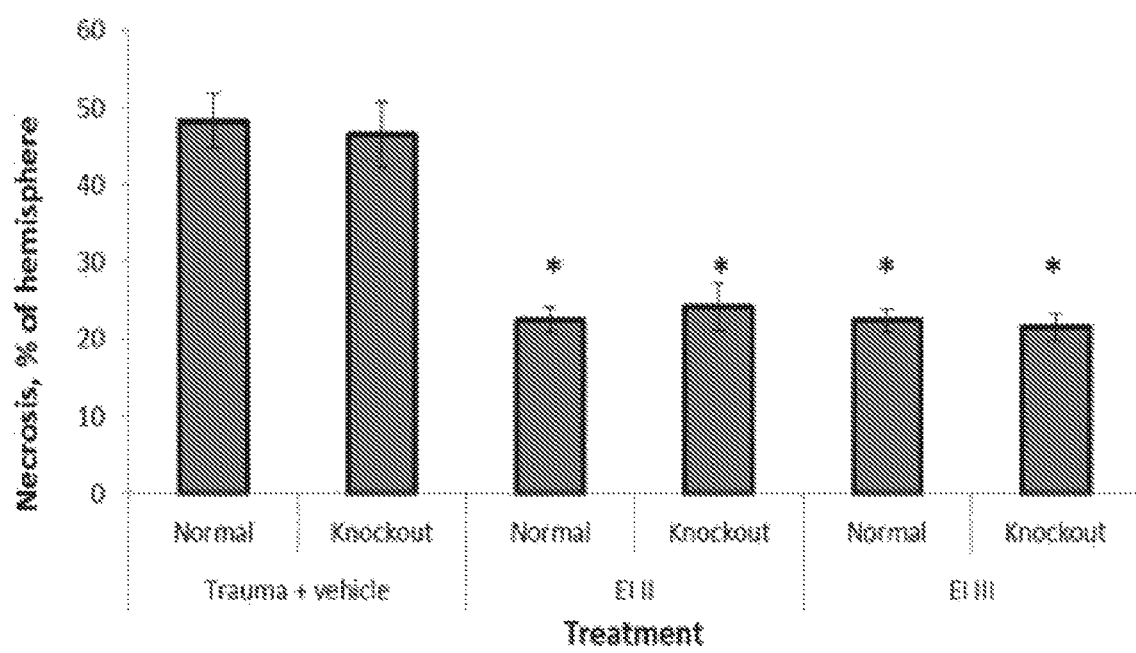

In view of the above promising results, an evaluation of the effect of elastase inhibitors on the necrotic process in-vivo was examined. The first in vivo model studied was traumatic brain injury (FIG. 8). First, the effect of elastase inhibitors II and III and the vehicle on control mice was examined. The mice were found to be healthy with NSS 0 to 1 and with no necrotic brain tissue. FIGS. 8A-B show the decrease in neuronal damage and reduction of necrotic space in elastase inhibitor II or III treated mice as compared to untreated traumatized animals. Neurological status was assessed using the neurological severity score. EIs II and III significantly reduce neurological damage as measured 1 hour post injury. FIG. 8B shows the amount of necrotic space in traumatized mice as measured by TTC staining; treatment with elastase inhibitors clearly reduced the space of the necrotic tissue from 50 to 25% of the damaged hemisphere. Practically identical results were obtained when the effect of the inhibitors was tested on neutrophil elastase knockout mice (FIG. 8B). In addition to the data presented in FIGS. 8A-B, the same experiments were performed on wild type Sprague Dawley rats and similar results were obtained (data not shown).

Taken together, the results presented in FIGS. 4A-C, 7A-B and 8A-B support the use of elastase inhibitors in attenuation of necrotic insult. Interestingly, there was no difference in the development of necrosis and in the reaction to treatment between normal and knockout mice, indicating that neutrophil elastase does not play any role in these two processes.

Further selected specific potent inhibitors of CELA3A or structurally related enzymes were tested in vivo in additional models of necrosis. Such active small-molecule inhibitors previously described were found by screening a library of CELA3A inhibitors based on 3D structure similarities and topological analogs of CELA3A enzyme. The in vitro activities of these compounds are shown below, see example 7. The effect of compound Z601-4253 (2-(piperidin-1-yl)thiazol-4-yl)(pyrrolidin-1-yl)methanonen which belongs to the 2-Aminothiazole group of active compounds was tested on protection against liver toxicity.

We evaluated the potential of this compound as an anti-necrotic agent against APAP hepatotoxicity. For this purpose, we examined the changes in the levels of serum biochemical markers for hepatic cell death: ALT and AST.

Figure 9:
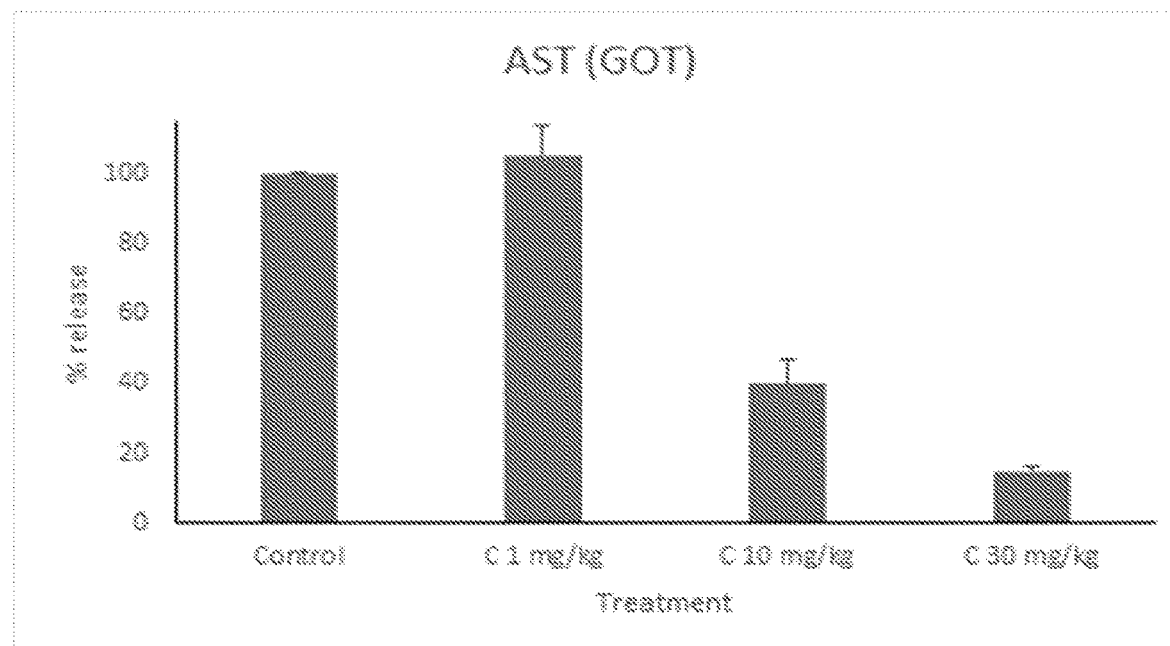
FIG. 9 shows the protective in vivo effect of compound Z601-4253 (2-(piperidin-1-yl)thiazol-4-yl)(pyrrolidin-1-yl) methanone, which belongs to the 2-Aminothiazole group of active compounds against liver toxicity caused by acetaminophen (APAP) administration. The compound was found by screening a library of CELA3A inhibitors based on 3D structure similarities and topological analogs of CELA3A enzyme. Of note the compound is active when administrated 4 hours after APAP administration.
Figure 10:
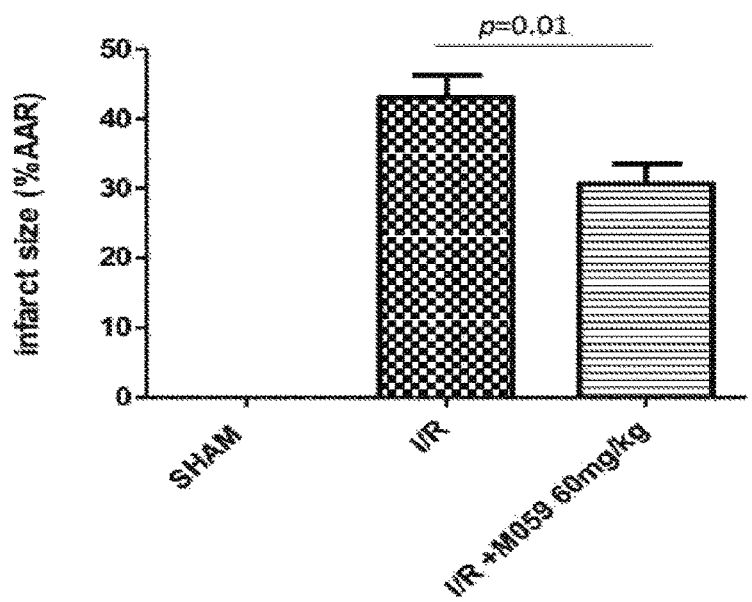
FIG. 10 shows the protective effect of compound 1-(2-(4-methylpiperazin-1-yl)-4,5-dihydro-1H-imidazol-1-yl) propan-1-one (M059-0891) which belongs to the 2-aminoimidazoline series found active by screening of a library of CELA3 inhibitors as described above. The results show a significant reduction in necrosis and infarct size by this inhibitor in a model of myocardial infarction/reperfusion in mice.

As shown in FIG. 9, treatment of mice with 300 mg/kg APAP produced a significant increase in the enzyme levels, the hepatic enzyme levels in blood were measured 24 hours after the paracetamol administration. The ALT level of APAP only treated mice was 8220+413 U/L and their AST level was 3553+290 U/L. Sham, control and compounds alone had ALT less than 2% and AST less than 4%. The parallel controls were reduced from the corresponding APAP treatment. The compound Z601-4253 which was injected IP 4 hours after the administration of APAP significantly reduced the level of both hepatic enzymes in the blood in a dose dependent manner protecting against paracetamol induced toxicity.

Another model that was studied was a murine in vivo model of myocardial ischemia/reperfusion injury (FIG. 10). The effect of the active compound 1-(2-(4-methylpiperazin-1-yl)-4,5-dihydro-1H-imidazol-1-yl)propan-1-one (M059-0891) which belongs to the 2-Aminoimidazoline Series was studied. The results show a significant reduction in necrosis and infarct size by the inhibitor.

Example 7

General Synthesis Methods for Embodied Compounds for Use in Accordance with the Invention Scheme 1 provided hereinbelow describes general synthetic methods for the preparation of 2-aminoimidazoline compounds, with Table 3 Providing embodied substituents for the indicated variables.

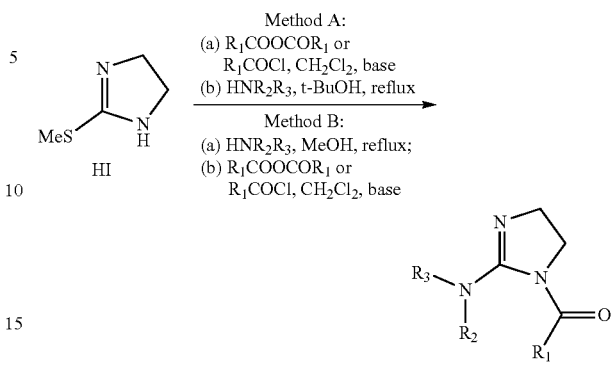

Scheme 1

TABLE 3

The preparation of certain 2-aminoimidazoline compounds was accomplished by preparing a mixture of 2-thiomethyl-dihydroimidazole hydroiodide (1.550 gm, 0.0063 mol) and diisopropyl ethylamine (2.2 eq) in methylene chloride (15 ml) stirred at room temperature and treated with propionic anhydride. The mixture was stirred at room temperature overnight. The reaction mixture was concentrated and diluted with methylene chloride and water (20 ml each). The methylene chloride layer was separated, dried on sodium sulphate and concentrated to give N-propanoyl-2-thiomethyl dihydroimidazole (1.2 gm). A mixture of N-propanoyl-2-thiomethyl dihydroimidazole (400 mg) and 1-methylpiperazine (3 eq) in t-butanol (12 ml) was refluxed for 3 days, then concentrated and purified on a silica gel column using 20-30% methanol-methylene chloride to give compound 1 (50 mg) along with starting material (210 mg). $^1$HNMR (DMSo-D$_6$): 0.99 (t, J=8 Hz, 3H), 2.16 (s, 3H), 2.32 (q, J=8 Hz, 2H), 2.49 (m, 4H), 3.04 (m, 4H), 3.39 (t, J=8 Hz, 2H), 3.81 (t, J=8 Hz, 2H); LCMS m z 225.0 [M+1]. This synthetic procedure follows the Method A as schematically depicted above.

The preparation of certain 2-aminoimidazoline compounds was accomplished by preparing a mixture of 2-thiomethyl dihydroimidazole hydroiodide (1.1 gm) and 1-methylpiperazine (1.5 eq) in methanol (15 ml) was refluxed until the reaction was complete (6-18 hours), then concentrated and dissolved in methylene chloride (20 ml) and treated with triethylamine (2 eq) and propionic anhydride (1.25 eq). The mixture was stirred at room temperature for 1 hour. The reaction mixture was then concentrated and purified on a silica gel column using $10^{-30}$% methanol-methylene chloride to give compound 1 (780 mg). Compound 1 (0.5 gm) was further purified on C-18 column using 0.1% TFA-water to give the TFA salt of compound 1 (280 mg). $^1$HNMR (CDCl$_3$): 1.17 (t, J=8 Hz, 3H), 2.38 (s, 3H), 2.49 (q, J=8 Hz, 2H), 2.54 (m, 4H), 3.32 (m, 4H), 3.61 (t, J=8 Hz, 2H), 3.93 (t, J=8 Hz, 2H); LCMS m z 225.0 [M+1]. This synthetic procedure follows the Method B as schematically depicted above.

The synthetic procedure of Method A was also followed to synthesize Compound 2 (M059-0851), with the following characteristics: $^1$HNMR (DMSO-d$_6$): 0.98 (t, J=8 Hz, 3H), 1.50-1.83 (m, 8H), 2.30 (q, J=8 Hz, 2H), 2.34-2.37 (m, 4H), 3.03-3.05 (m, 4H), 3.12-3.16 (m, 1H), 3.39 (t, J=8 Hz, 2H), 3.84 (t, J=8 Hz, 2H); LCMS m z 279.1 [M+1].

The synthetic procedure of Method A was also followed to synthesize Compound 3 TFA salt (M059-0032) followed by C-18 column purification, yielding the following characteristics: $^1$HNMR (DMSO-d$_6$): 1.82-1.90 (m, 2H), 1.96-2.03 (m, 2H), 3.33-3.37 (m, 2H), 3.50-3.54 (m, 2H), 3.71 (t, J=8 Hz, 2H), 4.39 (t, J=8 Hz, 2H), 6.81-6.82 (m, 1H), 7.50 (d, J=Hz, 1H), 8.11 (m, 1H), 9.84 (s, 1H); LCMS m z 234.0 [M+1].

The synthetic procedure of Method A was also followed to synthesize Compound 4 TFA salt (M059-0055), yielding the following characteristics: $^1$HNMR (DMSO-d$_6$): 1.08-1.83 (m, 8H), 1.81-1.85 (m, 4H), 2.15-2.22 (m, 1H), 2.59 (d, J=8Z, 2H), 3.38-3.41 (m, 4H), 3.36 (t, J=8 Hz, 2H), 4.17 (t, J=8 Hz, 2H), 9.47 (s, 1H); LCMS m z 250.1 [M+1].

The synthetic procedure of Method A was also followed to synthesize Compound 5 (M059-0082) The synthetic procedure of Method A was also followed to synthesize $^1$HNMR (DMSO-d$_6$): 1.48-1.74 (m, 8H), 1.85-1.90 (m, 4H), 2.49-2.56 (m, 1H), 3.18-3.23 (m, 2H), 3.34-3.40 (m, 6H); LCMS m/z 236.1 [M+1].

Compounds 6 (M059-0053) and Compound 7 (M059-0335) were prepared following method A in a similar protocol to compound 4.

Compound 8 (Z601-4253) was prepared from 2-piperidino-1,3-thiazole-4-carboxylic acid and pyrrolidine in methylene chloride in presence of DCC, triethyl amine and DMAP.

Scheme 2 provided hereinbelow describes general synthetic methods for the preparation of 2-aminoimidazoline compounds, with Table 3 Providing embodied substituents for the indicated variables.

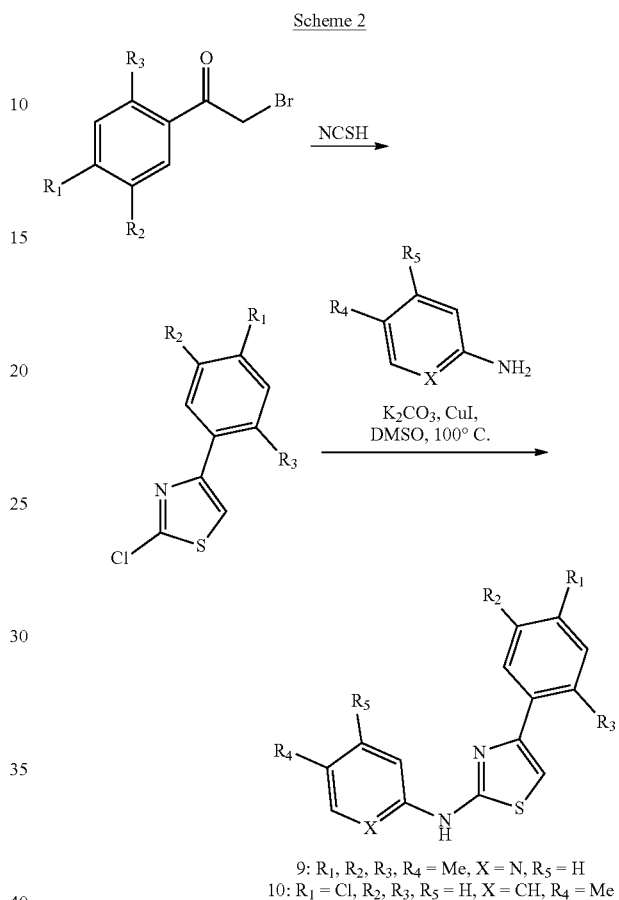

9: R$_1$, R$_2$, R$_3$, R$_4$ = Me, X = N, R$_5$ = H
10: R$_1$ = Cl, R$_2$, R$_3$, R$_5$ = H, X = CH, R$_4$ = Me

Compounds 9 (M008-0111) and 10 (4112-3656) were prepared in a method in accordance with that described in Scheme 2 from corresponding bromoacetophenones and amines Scheme 3 provided hereinbelow describes general synthetic methods for the preparation of 2-aminoimidazoline compounds.

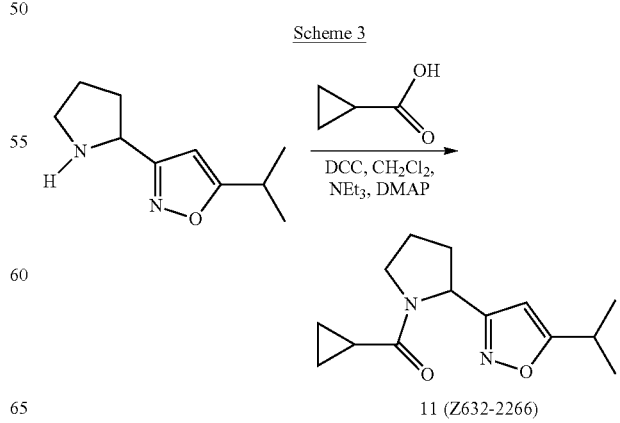

11 (Z632-2266)

Compound 11 (Z632-2266) was prepared from commercially available 5-isopropyl-3-pyrrolidin-2-ylisoxazole and cyclopropane carboxylic acid in methylene chloride in presence of DCC, triethyl amine and DMAP in accordance with Scheme 3.

Scheme 4 provided hereinbelow describes an additional general synthetic procedure for embodied compounds/compounds for use as herein described:

Scheme 4

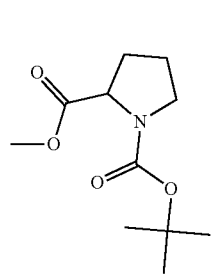 + 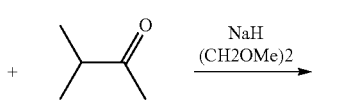 NaH (CH2OMe)2 →

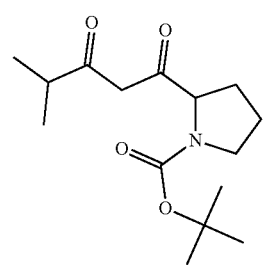

NH2OH•HCl
EtOH•H2O
→

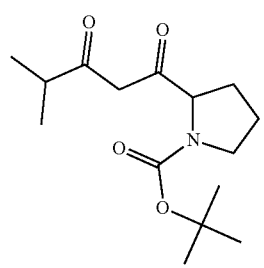

 →

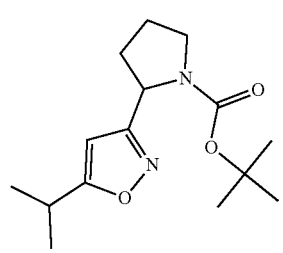 →

-continued

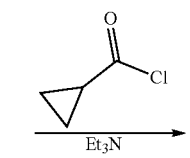 cyclopropane-C(O)Cl, Et3N →

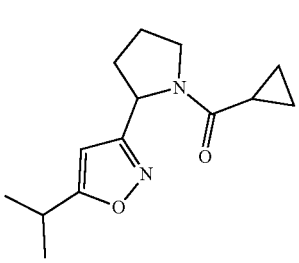

Scheme 5 provided hereinbelow describes an additional general synthetic procedure for embodied compounds/compounds for use as herein described:

Scheme 5

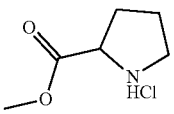 + 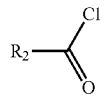 →

Z632-2266

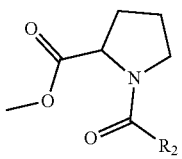

 + R2—C(O)—CH3 →

 →

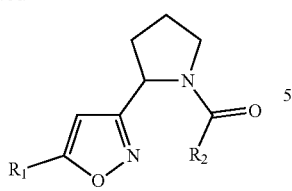

Scheme 6 provided hereinbelow describes an additional general synthetic procedure for embodied compounds/compounds for use as herein described:

Scheme 6

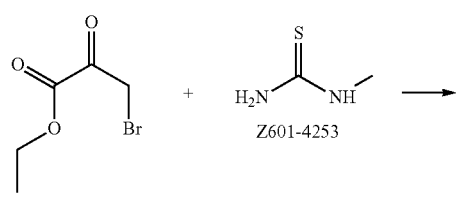

Scheme 7 provided hereinbelow describes an additional general synthetic procedure for embodied compounds/compounds for use as herein described:

Scheme 7

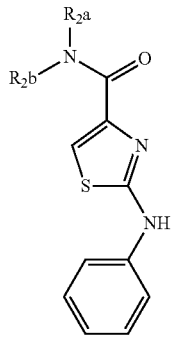

Scheme 8 provided hereinbelow describes an additional general synthetic procedure for embodied compounds/compounds for use as herein described. The reference provided is also fully incorporated by reference herein in its entirety.

Scheme 8

Scheme 9 provided hereinbelow describes an additional general synthetic procedure for embodied compounds/compounds for use as herein described:

Scheme 9

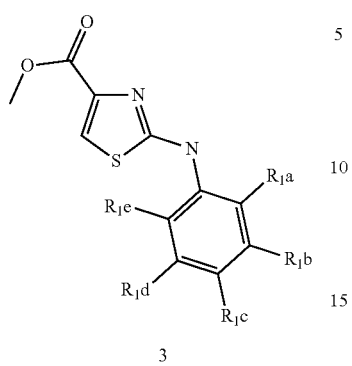

3

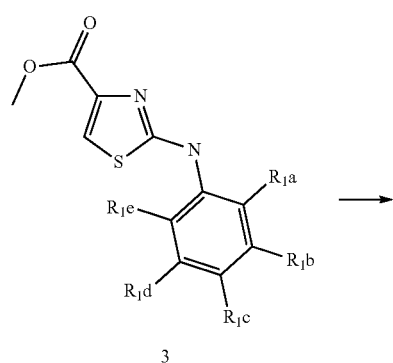

3

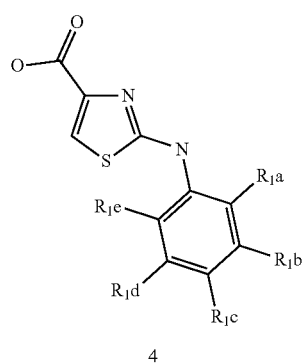

4

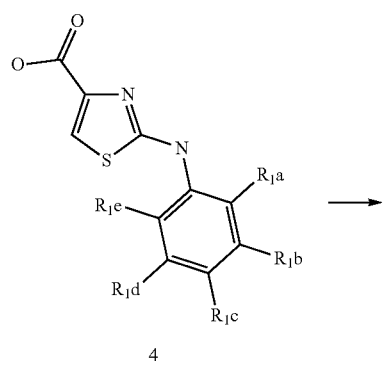

4

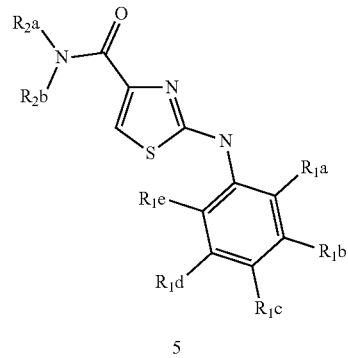

5

Briefly, PMR spectra were registered on a 300 MHz Bruker DPX and processed using Bruker XWinNMR software. All commercially obtained reagents were used without further purification.

Compound 3. Compound 1 (0.1 mol) was added to a mixture of compound 2 (0.1 mol) and ether (100 ml). The mixture was stirred at 28-30° C. for 12 hours and then cooled down to 5° C. The formed precipitate was collected by filtration, washed with water, dried and crystallized from ethanol to give pure reaction product 3 in 70-75% yields.

Compound 4. Compound 3 (0.1 mol) was suspended in a solution of NaOH (0.25 mol) and ethanol (5 ml) in water (200 ml). The mixture was stirred at 90° C. until the solid was completely dissolved. The resulting solution was cooled down to a room temperature and carefully acidified with acetic acid. The formed precipitate was collected by filtration, washed with water, dried and crystallized from dioxane to give pure reaction product 4 in 75-80% yields.

Compound 5. 1 mmol of the acid 4 was added to a solution of CDI (0.95 mmol) in 5 ml of dry DMF. The mixture was stirred at 80° C. for 2 hours while a gas was forming. Then 1 mmol of the amine $HNR_2aR_2b$ was added to the reaction mixture, it was refluxed for 3-4 hours and left overnight at room temperature. Then the mixture was poured into water (10 ml), the formed precipitate was collected by filtration and purified by crystallization from propanol-2 to give pure reaction product 5 in 40-85% yields.

And also referring to scheme 10:

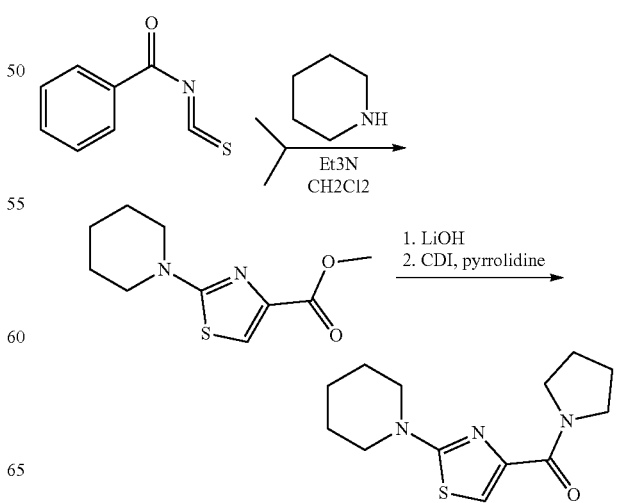

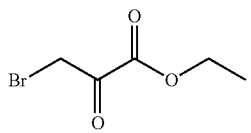

PCT Int. Appl., 2009054468, 30 Apr 2009

Where the reference provided is fully incorporated herein in its entirety.

The skilled artisan will appreciate how the above-described synthetic methods can be modified to prepare compounds as herein described in Table 1, or as defined by any formula provided herein.

Example 8

List of Active Small-Molecule Inhibitors Found by Screening a Library of CELA3A and CELA1 Inhibitors Based on 3D Structure Similarities and Topological Analogs The following compounds were prepared by vendor ChemDiv Inc. (San Diego, USA) and their respective ChemDiv I.D. numbers are shown in Table 4 below.

TABLE 4

| I.D. | IUPAC NAME |
|---|---|
| Z087-0195 | 3,4-bis((2-(pyrrolidin-1-yl)ethyl)amino)-1,2,5-thiadiazole 1,1-dioxide |
| Z601-4253 | (2-(piperidin-1-yl)thiazol-4-yl)(pyrrolidin-1-yl)methanone |
| Z632-2266 | cyclopropyl(2-(5-isopropylisoxazol-3-yl)pyrrolidin-1-yl)methanone |
| M008-0111 | N-(4-methylpyridin-2-yl)-4-(2,4,5-trimethylphenyl)thiazol-2-amine |
| D216-0746 | 4-((2-methylindolin-1-yl)sulfonyl)benzoic acid |
| M059-0891 | 1-(2-(4-methylpiperazin-1-yl)-4,5-dihydro-1H-imidazol-1-yl)propan-1-one |
| 3952-1000 | 6-bromo-2-(3,5-dimethoxyphenyl)-4H-benzo[d][1,3]oxazin-4-one |
| E214-0380 | 6-methyl-5-((2-methylpiperidin-1-yl)sulfonyl)pyrimidine-2,4(1H,3H)-dione |
| 5149-0030 | ethyl 2-(1,1-dioxido-3-oxobenzo[d]isothiazol-2(3H)-yl)acetate |
| Z632-6109 | N-methyl-4,5,6,7,8,9-hexahydro-1H-cycloocta[c]pyrazole-3-carboxamide |
| 8018-2960 | 2-(5-(pyridin-4-yl)-2H-tetrazol-2-yl)acetic acid |
| 4789-3852 | 2-(furan-2-yl)-5,6,7,8-tetrahydro-4H-benzo[4,5]thieno[2,3-d][1,3]oxazin-4-one |
| M059-0082 | cyclopentyl(2-(pyrrolidin-1-yl)-4,5-dihydro-1H-imidazol-1-yl)methanone |
| L150-1122 | 3-((5-acetamido-1H-1,2,4-triazol-3-yl)thio)propanoic acid |
| 4112-3656 | N1-(4-(4-chlorophenyl)thiazol-2-yl)-N4,N4-dimethylbenzene-1,4-diamine |
| M059-0032 | furan-2-yl(2-(pyrrolidin-1-yl)-4,5-dihydro-1H-imidazol-1-yl)methanone |
| Z606-8336 | 7-(4-ethylpiperazin-1-yl)-5,6-dimethyl-[1,2,4]triazolo[1,5-a]pyrimidine |
| M284-0488 | 7-fluoro-10-(2-(4-(4-isopropylpiperazin-1-yl)-2-oxoethyl)-2,3-dihydro-1H-benzo[e]pyrrolo[1,2-a][1,4]diazepine-5,11(10H,11aH)-dione |
| 4334-1600 | bromophenyl)-4-oxo-4H-benzo[d][1,3]oxazin-6-yl acetate-3)-2 |
| 4356-0595 | 2-(tert-butyl)-3-(1-methyl-1H-benzo[d]imidazol-2-yl)-4-oxo-4H-chromen-7-yl pivalate |
| M059-0055 | 2-cyclopentyl-1-(2-(pyrrolidin-1-yl)-4,5-dihydro-1H-imidazol-1-yl)ethanone |
| D226-0031 | 3-methyl-8-(piperidin-1-yl)-1H-purine-2,6(3H,7H)-dione |
| E205-0066 | 5-ethyl-N-(pyridin-2-ylmethyl)-5H-[1,2,4]triazino[5,6-b]indol-3-amine |
| 8019-5381 | 3-((4-chloro-1H-pyrazol-1-yl)methyl)-N-(2-(3-fluorobenzamido)ethyl)-1,2,4-oxadiazole-5-carboxamide |
| 4240-0470 | 1-(4-(methylthio)benzyl)-4-tosylpiperazine |
| F684-0507 | 2-(2-ethylphenylsulfonamido)-5-(4-ethylpiperazin-1-yl)benzoic acid |
| G830-0845 | 2-amino-N-(2,4-difluorophenyl)pyrimidine-5-sulfonamide |
| D226-0031 | 3-methyl-8-(piperidin-1-yl)-1H-purine-2,6(3H,7H)-dione |
| P316-0028 | 5-chloro-N-(2-oxo-1-phenylpyrrolidin-3-yl)thiophene-2-sulfonamide |
| 3506-0172 | 3-(pyrrolidin-1-ylsulfonyl)benzoic acid |
| 3346-3249 | (3,5-dimethyl-1H-pyrazol-1-yl)(3,4,5-trimethoxyphenyl)methanone |
| M284-0942 | N-(3,4-difluorophenyl)-2-(8-fluoro-5,11-dioxo-2,3,11,11a-tetrahydro-1H-benzo[e]pyrrolo[1,2-a][1,4]diazepin-10(5H)-yl)acetamide |
| 4953-1443 | 5-(cyclohexylmethyl)-3-(pyridin-2-yl)-1,2,4-oxadiazole |
| D529-0049 | ethyl 5-methyl-4-(2-((4-methylbenzyl)amino)-2-oxoethyl)-7-phenyl-4,7-dihydro-[1,2,4]triazolo[1,5-a]pyrimidine-6-carboxylate |
| M059-1012 | cyclopentyl(2-(4-ethylpiperazin-1-yl)-4,5-dihydro-1H-imidazol-1-yl)methanone |
| R052-2664 | [1,2,4]triazolo[1,5-a]pyrimidine-2-carboxylic acid |
| M059-0335 | 1-(2-(piperidin-1-yl)-4,5-dihydro-1H-imidazol-1-yl)butan-1-one |
| T404-2346 | (4-(6-chloro-[1,2,4]triazolo[4,3-a]pyridin-3-yl)piperazin-1-yl)(1-phenylcyclopropyl)methanone |
| M284-0939 | N-(2,4-difluorophenyl)-2-(5,11-dioxo-2,3,11,11a-tetrahydro-1H-benzo[e]pyrrolo[1,2-a][1,4] diazepin-10(5H)-yl)acetamide |
| M059-0053 | 2-ethyl-1-(2-(pyrrolidin-1-yl)-4,5-dihydro-1H-imidazol-1-yl)butan-1-one |
| Y200-4081 | N-[4-[4-(isobutyrylamino)phenoxy)phenyl]-2-methyl-propionamide |

Inhibitors of Necrotic Cell Death

These compounds were tested for their ability to inhibit necrosis induced by KCN in PC12 cells. The necrotic mode of cell death in this system was validated as previously described. The results are presented in table below. PC12 cells were challenged with KCN as described above. The protective results of the compounds against KCN-induced necrosis assessed using LDH release method are shown below in Table 5. The IC50 values of these inhibitors is in the range of tens to single nanomolar.

TABLE 5

| I.D. | % protection | | | | |
|---|---|---|---|---|---|
| | at 1 μM | at 0.1 μM | At 10 nM | at 1 nM | at 0.1 nM |
| Z087-0195 | 98.5 | 80 | 25 | 21 | 9 |
| Z601-4253 | 100 | 74 | 61 | 34 | 29 |
| Z632-2266 | 93 | 78 | 46 | 22 | 13 |
| M008-0111 | 90 | 46 | 38 | 36 | 29 |
| D216-0746 | 90 | 84 | 47 | 37 | 29 |
| M059-0891 | 85 | 84 | 55 | 36 | 25 |
| 3952-1000 | 77 | 35 | 38 | 33 | 35 |
| E214-0380 | 83 | 51 | 39 | 21 | 18 |
| 5149-0030 | 80 | 68 | 35 | 25 | 19 |
| Z632-6109 | 81 | 70 | 40 | 25 | 26 |
| 8018-2960 | 84 | 80 | 54 | 25 | 38 |
| 4789-3852 | 81 | 61 | 55 | 25 | 18 |
| L150-1122 | 68 | 44 | 30 | 25 | 22 |
| 4112-3656 | 77 | 73 | 55 | 25 | 30 |
| M059-0032 | 72 | 59 | 37 | 25 | 7 |
| Z606-8336 | 75 | 64 | 54 | 35 | 29 |
| M284-0488 | 80 | 72 | 82 | 51 | 35 |
| 4334-1600 | 74 | 71 | 28 | 30 | 28 |
| 4356-0595 | 69 | 57 | 36 | 21 | 4 |
| M059-0055 | 68 | | | | |
| D226-0031 | 65 | 37 | 43 | 26 | 29 |
| E205-0066 | 58 | 32 | 18 | | |
| 8019-5381 | 56 | 49 | 32 | | |
| 4240-0470 | 56 | | | | |
| F684-0507 | 56 | | | | |
| G830-0845 | 54 | | | | |
| D226-0031 | 53 | | | | |
| P316-0028 | 53 | 49 | 43 | | |
| 3506-0172 | 52 | 19 | 18 | | |
| 3346-3249 | 52 | | | | |
| M284-0942 | | 52 | | | |
| 4953-1443 | 51 | | | | |
| D529-0049 | 51 | 42 | 33 | | |
| M059-1012 | | 51 | | | |
| R052-2664 | 50 | 49 | 21 | | |
| M059-0335 | 47 | | | | |
| T404-2346 | | 42 | | | |
| M284-0939 | | 40 | | | |
| M059-0053 | 39 | | | | |

DISCUSSION

The inability to prevent or treat necrotic cell death is an unresolved problem. The present inventors have shown that reducing elastase like-activity by siRNA or by specific elastase small molecules inhibitors confer protection on cells undergoing necrotic cell death. The protective effect was validated by different methods. The ability of elastase inhibitors to protect cells against death appears to be independent of the cell death trigger as was observed after treatment with KCN or previously with anti Fas and staurosporine each in the presence of oligomycin A. Different classes of peptide and heterocyclic elastase inhibitors were able to confer protection indicating that the effect is not compound-specific. Additional support for a role of an intracellular elastase in this death process was provided by an early increase of elastase-like activity in cellular extracts of necrotic cells, which occurs before any signs of frank necrotic cell death. The increase in activity was confirmed by measurement of elastase-like activity using a specific substrate Additionally treatment of intact cells with a permeable elastase inhibitor (EI II and EI III) abrogated the induction of the enzymatic activity in the cells The short time required for induction of elastase-like activity during necrosis indicates that the enzyme acts at an early stage of the necrotic process, possibly as an early stage proteolytic activator in the cascade of molecular events ultimately leading to cell death. This role of elastase in necrosis is in accord with the known involvement of proteolytic cascades in cell death processes. Thus, the early marked induction of elastase-like activity and the ability of elastase inhibitors to prevent cell death support a key role of elastase-like enzyme in the necrotic process.

The ability of elastase inhibitors to prevent brain cells necrotic damage in-vivo was shown using the closed head injury (trauma) model in mice and rats. Improvement in neurological function (reduction in NSS) following administration of elastase inhibitors was mainly observed 1 hour post trauma, when the decrease in neurological function was most prominent. The protective effect on development of the necrotic area as manifested by TTC staining was prominent even 24 hours post trauma. TTC staining of brain slices revealed an impressive picture: the elastase inhibitors protected up to 60% of brain tissue that otherwise was expected to develop necrosis.

Affected tissues, such as from a myocardial infarction, become necrotic within 4-12 h after the incident. Similarly, in the case of a brain stroke necrosis develops within a few hours up to 24 hours and even more after the infarct, causing irreparable damage to brain tissues. Treatment with the elastase inhibitors immediately after the incident will prevent the occurrence of necrosis. Thus, the present study clearly represents a therapeutic treatment.

In the present study, it was clearly shown that elastase inhibitors curtail necrotic cell death independently of immune cell activity or contribution. In this experimental system, a cell monocultures devoid of neutrophils or glial cells capable of releasing HNE was utilized. Of note, the PC12 cell line used in the present study is of neuronal origin and devoid of a neutrophil elastase. Moreover, cumulatively these results indicate that a ubiquitous elastase-like enzyme is involved in initiating necrotic cell death. Thus, it is likely that the improvement in NSS following elastase inhibitor administration in-vivo is a consequence of inhibition of an intracellular elastase-like enzyme that resides in neuronal cells. This stems from the fact that during the early stage of posttraumatic recovery in immune preferred site there was no significant neutrophil infiltration and thereby a confounding effect due to inhibition of a neutrophil elastase is most unlikely. This notion is supported by the results showing that NE knockout mice are responsive to the protective effect of elastase inhibitors against necrosis.

In conclusion, it was demonstrated herein for the first time that specific cell permeable elastase inhibitors prevent necrotic cell death. These inhibitors could be used for prevention of cell death before onset of the necrotic insult, a protective action which surprisingly emerged from the studies conducted herein. This therapeutic approach may be especially useful for treatment of patients who are at high risk of stroke or myocardial infarction.

The ability of elastase inhibitors to protect cells against death appears to be independent of the cell death trigger and was documented in vitro and in vivo. Further, by siRNA silencing more specific identification of the target was enable The presented exemplary list of active compounds possesses molecules bearing structural similarities and topological analogy to CELA3A or a similar enzyme. All these compounds were found to inhibit necrosis in the assay. All compounds were able to confer significant protection at 1 µM or lower concentrations.

It was already observed that exposure of PC-12 cells to high concentrations (up to 300 µM) of non-specific elastase inhibitor EI II and III, which were inactive by themselves, significantly inhibited necrosis induced by KCN. Yet, it can be equally readily seen that the disclosed small-molecule inhibitors were effective at concentrations lower by several orders of magnitude. This unexpected showing of superiority of a specific inhibitor versus a non-specific inhibitor corroborates the importance of the specific targeting.

Affected tissues, such as from a myocardial infarction, become necrotic within 4-12 h after the incident. Similarly, in the case of a brain stroke necrosis develops within a few hours up to 24 hours and even more after the infarct, causing irreparable damage to brain tissues. Treatment with the elastase inhibitors immediately after the incident will prevent the occurrence of necrosis. This is further corroborated by the results showing that injection of a specific small molecule inhibitor discovered by screening a library of CELA3A inhibitors based on 3D structure similarities and topological analogs protects against liver toxicity even when administrated 4 hours after APAP administration. Treatment of MI is also supported by showing about 30% of reduction in the infarct size by another small inhibitor discovered by the screening. Thus, the present study clearly represents a potential for therapeutic treatment.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method for ameliorating, inhibiting, or reducing the incidence of necrotic cell death in a subject in need thereof, wherein the method comprises administering to the subject a therapeutically effective amount of a compound of Formula VI:

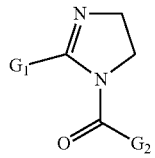

Formula VI or a pharmaceutically acceptable salt thereof,
wherein:
$G_1$ is pyrrolidinyl, pyrazolidinyl, imidazolidinyl, piperidinyl, or piperazinyl, wherein the pyrrolidinyl, pyrazolidinyl, imidazolidinyl, piperidinyl, or piperazinyl is optionally substituted with one or more substituents independently selected from the group consisting of halogen, $NO_2$, CN, $C_1$-$C_6$ alkyl, $C_1$-$C_6$ haloalkyl, $NH_2$, OH, $OC_1$-$C_6$ alkyl, C(O)H, C(O)$C_1$-$C_6$ alkyl, C(O)$NH_2$, C(O)OH, and C(O)O$C_1$-$C_6$ alkyl; and $G_2$ is alkyl, cycloalkyl, heterocyclyl, or aryl, wherein the alkyl, cycloalkyl, heterocyclyl, or aryl is optionally substituted with one or more substituents independently selected from the group consisting of halogen, $NO_2$, CN, $C_1$-$C_6$ alkyl, $C_1$-$C_6$ haloalkyl, $NH_2$, OH, $OC_1$-$C_6$ alkyl, C(O)H, C(O)$C_1$-$C_6$ alkyl, C(O)$NH_2$, C(O)OH, and C(O)O$C_1$-$C_6$ alkyl;

wherein the subject suffers from cellular necrosis of a cell selected from the group consisting of a bone cell, a brain cell, a cardiac cell, a cartilage cell, an embryonic cell, an epidermal cell, an epithelial cell, a fibroblast, a gastrointestinal cell, a glial cell, a gonadal cell, a hematopoetic cell, a kidney cell, a liver cell, a lung cell, a lymphocyte, a macrophage, a muscle cell, a neuronal cell, a pancreatic cell, a parenchymal cell, a retinal cell, a spleen cell, and a stem cell.

2. The method of claim 1, wherein the subject suffers from cellular necrosis of a cell as a result of a disease or condition selected from the group consisting of acute tubular necrosis, alcoholism, aseptic necrosis, asphyxia, Anderson's disease, avascular necrosis, celiac disease, chemotherapy induced necrosis, cirrhosis, Crohn's disease, cystic fibrosis, degenerative arthritis, diabetes mellitus, endometriosis, gangrene, glomerulonephritis, hemoglobinuria, hepatitis, hyperthermia, impairment of transplant tissue, ischemic heart disease, leukemia, lymphoma, macular degeneration, muscular dystrophy, myocardial infarction, necrotizing fasciitis, neonatal respiratory distress, nephrotoxicity, osteomyelitis, pancreatitis, phenylketonuria, psoriasis, radiation induced necrosis, reduced quality of transplant tissue, renal cortical necrosis, retinal necrosis, rheumatoid arthritis, sepsis, spinal cord injury, Stevens-Johnson syndrome, syphilis, tuberculosis, tyrosemia, vascular dystrophy, a bacterial infection, a burn, a cerebrovascular damage, a cerebrovascular disease, a cold injury, a compartment syndrome, a complication of steroid treatment, a congenital mitochondrial disease, a fungal infection, an incarcerated hernia, an iron-load complication, a metabolic inherited disease, a necrosis associated with administration with or exposure to an agrochemical, a necrosis associated with administration with or exposure to a chemical toxin, a necrosis associated with a dermal filler administration, a necrosis associated with administration with or exposure to a drug, a necrosis associated with an ectopic drug administration, a necrosis associated with administration with or exposure to a heavy metal, a necrosis associated with administration with or exposure to a snake venom, a necrosis associated with administration with or exposure to a spider venom, a necrosis associated with administration with or exposure to a warfare organophosphate, a necrotizing procolitis, a neurodegenerative disease, a parasitic infection, a placental infarct, a pressure sore, a reperfusion injury, a toxic epidermal necrosis, and a viral infection.

3. The method of claim 1, wherein:
(i) $G_1$ is pyrrolidinyl; and
$G_2$ is alkyl, cyclopropyl, cyclobutyl, cyclohexyl, cycloheptyl, cyclooctyl, heterocyclyl, or aryl;
wherein the heterocyclyl contains 1, 2, 3, or 4 heteroatoms independently selected from the group consisting of N and S;
wherein the alkyl is substituted with one or more substituents independently selected from the group consisting of halogen, $NO_2$, CN, $C_1$-$C_6$ alkyl, $C_1$-$C_6$ haloalkyl, $NH_2$, OH, $OC_1$-$C_6$ alkyl, C(O)H, C(O)$C_1$-$C_6$ alkyl, C(O)$NH_2$, C(O)OH, and C(O)O$C_1$-$C_6$ alkyl; and
wherein the cyclopropyl, cyclobutyl, cyclohexyl, cycloheptyl, cyclooctyl, heterocyclyl, or aryl is optionally substituted with one or more substituents independently selected from the group consisting of halogen, $NO_2$, CN, $C_1$-$C_6$ alkyl, $C_1$-$C_6$ haloalkyl, $NH_2$, OH, $OC_1$-$C_6$ alkyl, C(O)H, C(O)$C_1$-$C_6$ alkyl, C(O)$NH_2$, C(O)OH, and C(O)O$C_1$-$C_6$ alkyl; or (ii) $G_1$ is piperidinyl, wherein the piperidinyl is optionally substituted with one or more substituents independently selected from the group consisting of halogen, $NO_2$, CN, $C_1$-$C_6$ alkyl, $C_1$-$C_6$ haloalkyl, $NH_2$, OH, $OC_1$-$C_6$ alkyl, C(O)H, C(O)$C_1$-$C_6$ alkyl, C(O)$NH_2$, C(O)OH, and C(O)O$C_1$-$C_6$ alkyl; and
$G_2$ is cycloalkyl, heterocyclyl, or aryl, wherein the cycloalkyl, heterocyclyl, or aryl is optionally substituted with one or more substituents independently selected from the group consisting of halogen, $NO_2$, CN, $C_1$-$C_6$ alkyl, $C_1$-$C_6$ haloalkyl, $NH_2$, OH, $OC_1$-$C_6$ alkyl, C(O)H, C(O)C$_1$-C$_6$ alkyl, C(O)NH$_2$, C(O)OH, and C(O)OC$_1$-C$_6$ alkyl; or (iii) G$_1$ is piperazinyl, wherein the piperazinyl is optionally substituted with one or more substituents independently selected from the group consisting of halogen, NO$_2$, CN, C$_1$-C$_6$ alkyl, C$_1$-C$_6$ haloalkyl, NH$_2$, OH, OC$_1$-C$_6$ alkyl, C(O)H, C(O)C$_1$-C$_6$ alkyl, C(O)NH$_2$, C(O)OH, and C(O)OC$_1$-C$_6$ alkyl; and G$_2$ is cycloalkyl, heterocyclyl, or aryl;
wherein the heterocyclyl contains 1, 2, 3, or 4 heteroatoms independently selected from the group consisting of N and S; and
wherein the cycloalkyl, heterocyclyl, or aryl is optionally substituted with one or more substituents independently selected from the group consisting of halogen, NO$_2$, CN, C$_1$-C$_6$ alkyl, C$_1$-C$_6$ haloalkyl, NH$_2$, OH, OC$_1$-C$_6$ alkyl, C(O)H, C(O)C$_1$-C$_6$ alkyl, C(O)NH$_2$, C(O)OH, and C(O)OC$_1$-C$_6$ alkyl.

4. The method of claim 3, wherein:
G$_1$ is pyrrolidinyl; and
G$_2$ is CH$_2$CH$_3$.

5. The method of claim 3, wherein:
G$_1$ is piperazinyl, wherein the piperazinyl is substituted with one or more substituents independently selected from the group consisting of halogen, NO$_2$, CN, C$_1$-C$_6$ alkyl, C$_1$-C$_6$ haloalkyl, NH$_2$, OH, OC$_1$-C$_6$ alkyl, C(O)H, C(O)C$_1$-C$_6$ alkyl, C(O)NH$_2$, C(O)OH, and C(O)OC$_1$-C$_6$ alkyl; and
G$_2$ is phenyl.

6. The method of claim 1, wherein:
G$_1$ is pyrrolidinyl; and
G$_2$ is pyrrolidinyl or tetrahydrofuranyl.

7. The method of claim 1, wherein:
G$_1$ is piperazinyl, wherein the piperazinyl is optionally substituted with one or more substituents independently selected from the group consisting of halogen, NO$_2$, CN, C$_1$-C$_6$ alkyl, C$_1$-C$_6$ haloalkyl, NH$_2$, OH, OC$_1$-C$_6$ alkyl, C(O)H, C(O)C$_1$-C$_6$ alkyl, C(O)NH$_2$, C(O)OH, and C(O)OC$_1$-C$_6$ alkyl; and
G$_2$ is CH$_3$, CH$_2$CH$_3$, CH$_2$CH$_2$CH$_3$, CH$_2$CH$_2$CH$_2$CH$_3$, CH$_2$CH$_2$CH$_2$CH$_2$CH$_3$, or CH$_2$CH$_2$CH$_2$CH$_2$CH$_2$CH$_3$.

8. The method of claim 7, wherein the compound is:

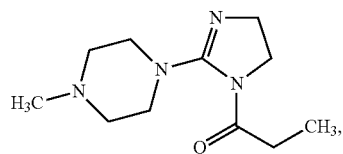 [SMILES: CCC(=O)N1CCN=C1N1CCN(C)CC1]

or a pharmaceutically acceptable salt thereof.

9. The method of claim 1, wherein the compound is:

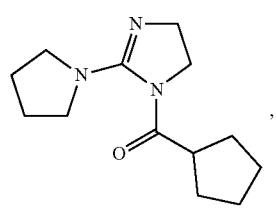 [SMILES: O=C(C1CCCC1)N1CCN=C1N1CCCC1]

or a pharmaceutically acceptable salt thereof.

10. The method of claim 1, wherein the compound is selected from the group consisting of:

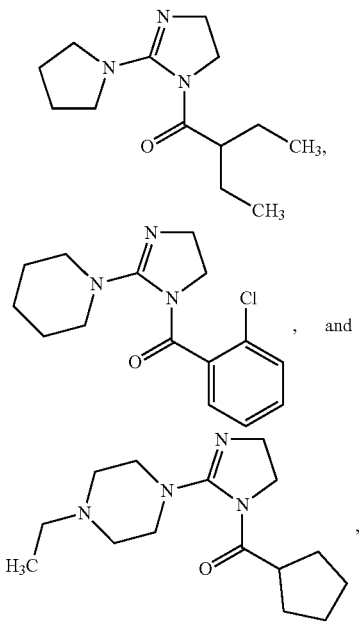

or a pharmaceutically acceptable salt thereof.

11. The method of claim 1, wherein the method further comprises administering to the subject an anti-aging agent selected from the group consisting of metformin, an antioxidant, a fatty acid, a hormone, and a phytochemical.

12. The method of claim 1, wherein the method further comprises administering to the subject an anti-apoptotic agent.

13. The method of claim 12, wherein the anti-apoptotic agent is administered to the subject prior to, together with, or after administration of the compound of Formula VI, or a pharmaceutically acceptable salt thereof.

14. The method of claim 12, wherein the anti-apoptotic agent is selected from the group consisting of (R)—N-(2-heptyl)methylpropargylamine (R-2HMP), vitamin D, vitamin E, ursodeoxycholic acid, and a caspase inhibitor.

15. A method for ameliorating, inhibiting, or reducing the incidence of necrotic cell death in a subject in need thereof, wherein the method comprises administering to the subject a therapeutically effective amount of 2-cyclopentyl-1-(2-(pyrrolidin-1-yl)-4,5-dihydro-1H-imidazol-1-yl)ethanone of the following structure:

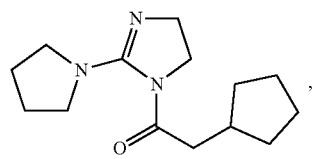 [SMILES: O=C(CC1CCCC1)N1CCN=C1N1CCCC1]

or a pharmaceutically acceptable salt thereof;
wherein the subject suffers from cellular necrosis of a cell selected from the group consisting of a bone cell, a brain cell, a cardiac cell, a cartilage cell, an embryonic cell, an epidermal cell, an epithelial cell, a fibroblast, a gastrointestinal cell, a glial cell, a gonadal cell, a hematopoetic cell, a kidney cell, a liver cell, a lung cell, a lymphocyte, a macrophage, a muscle cell, a neuronal cell, a pancreatic cell, a parenchymal cell, a retinal cell, a spleen cell, and a stem cell.

16. A method for ameliorating, inhibiting, or reducing the incidence of necrotic cell death in a subject in need thereof, wherein the method comprises administering to the subject a therapeutically effective amount of furan-2-yl(2-(pyrrolidin-1-yl)-4,5-dihydro-1H-imidazol-1-yl)methanone of the following structure:

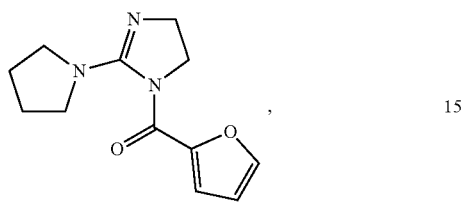

or a pharmaceutically acceptable salt thereof;
  wherein the subject suffers from cellular necrosis of a cell selected from the group consisting of a bone cell, a brain cell, a cardiac cell, a cartilage cell, an embryonic cell, an epidermal cell, an epithelial cell, a fibroblast, a gastrointestinal cell, a glial cell, a gonadal cell, a hematopoetic cell, a kidney cell, a liver cell, a lung cell, a lymphocyte, a macrophage, a muscle cell, a neuronal cell, a pancreatic cell, a parenchymal cell, a retinal cell, a spleen cell, and a stem cell.

* * * * *

```
                           SEQUENCE LISTING

<160> NUMBER OF SEQ ID NOS: 40

<210> SEQ ID NO 1
<211> LENGTH: 21
<212> TYPE: DNA
<213> ORGANISM: Artificial Sequence
<220> FEATURE:
<223> OTHER INFORMATION: Synthetic Construct - Sequence 1

<400> SEQUENCE: 1
atgatctgca tcagttgtaa a                                              21

<210> SEQ ID NO 2
<211> LENGTH: 21
<212> TYPE: DNA
<213> ORGANISM: Artificial Sequence
<220> FEATURE:
<223> OTHER INFORMATION: Synthetic Construct - Sequence 2

<400> SEQUENCE: 2
cggcaacatg ctggtccttt a                                              21

<210> SEQ ID NO 3
<211> LENGTH: 21
<212> TYPE: DNA
<213> ORGANISM: Artificial Sequence
<220> FEATURE:
<223> OTHER INFORMATION: Synthetic Construct - Sequence 3

<400> SEQUENCE: 3
ctgcctttgg ctgcaacttc a                                              21

<210> SEQ ID NO 4
<211> LENGTH: 21
<212> TYPE: DNA
<213> ORGANISM: Artificial Sequence
<220> FEATURE:
<223> OTHER INFORMATION: Synthetic Construct - Sequence 4
```

-continued

```
<400> SEQUENCE: 4
aattctccga acgtgtcacg t                                                21

<210> SEQ ID NO 5
<211> LENGTH: 6099
<212> TYPE: DNA
<213> ORGANISM: Homo sapiens

<400> SEQUENCE: 5
cgtagctatt tcaaggcgcg cgcctcgtgg tggactcacc gctagcccgc agcgctcggc       60
ttcctggtaa ttcttcacct cttttctcag ctccctgcag catgggtgct gggccctcct      120
tgctgctcgc cgccctcctg ctgcttctct ccggcgacgg cgccgtgcgc tgcgacacac      180
ctgccaactg cacctatctt gacctgctgg gcacctgggt cttccaggtg gctccagcg       240 gttcccagcg cgatgtcaac tgctcggtta tgggaccaca agaaaaaaaa gtagtggtgt      300
accttcagaa gctggataca gcatatgatg accttggcaa ttctggccat ttcaccatca      360
tttacaacca aggctttgag attgtgttga atgactacaa gtggtttgcc ttttttaagg      420
atgtcactga ttttatcagt catttgttca tgcagctggg aactgtgggg atatatgatt      480
tgccacatct gaggaacaaa ctggccatga acagacgttg gggctaagag acagagcagc      540
ctgcgacagt gtggacctac ctgtagcagc tagcaaaggc ctctagcagc tacagtccct      600
tctggagtct ttatttgcat gcaaaatgca aaggagtcct ggtgacctac ctccaaggca      660
gctgccctcc tgaacactcc cttggaaaac agtaaacatc attttggaat gtgaacaacc      720
agagactaca caggagaaag gaaaaaaaaa ttctgaagat gcaaatcttg ggtggcttc       780 accgttcagt ttttaataa aaggaacaat atacaacacg ttgttctttt tctcttttga      840
aatcccttct attacagtga ttttttttcta agattgtcag gatttgaagt gtatgttttg      900
ttttattcac agcgtaaatt ttattcacag tttaactgtc tgcctgagtg tctttccttt      960
ctctaattac cttgaggaac ccaagagcct gttgtaagga gaaataagg cccttggatc      1020 tcttgagatt cacagatata agttattgaa gggaagatgg tcctatggag gacatattta      1080
aagaagggaa aaaagaggct ttctcagata tgtcagactg ctatagtata cttctacaga      1140
ttatagacct ccagtacctc tggccagaaa gatggtatcg taaacaccct attttttttc      1200
tttctttttt tcattaggta caagctttgt gctaagaagt tgacatacta aagctacaa       1260 aagttctgta aagtagatat aactagtttc attttataga tagagaaaat taatctctta      1320
cagtgctaag ctcacagagt ttctaactgt aaaatgctag aacttgtctt tcaagcctaa      1380
agacttcctt ggggctaaat agtgaaaaaa gccatttcac aaataagtaa atggtattta      1440
gaggcatatt tggatttcct ggtaaattcc agtctgtgag catcatgaat attagtttaa      1500
tgttgcatgg gctcatgttg aagttttaag agaagaactg ccttgaagct taggtttcct      1560
tagctattag gctactgact ttcttgccta aaccagggtt ttttcattga agaccaaaac      1620
ttaccttctc cttcagtttg tagtttggaa attggtagaa gagctttgta aacttcaaat      1680
taagtacaaa ctaagtgtca tagtcaaatt tactaatctt aattacagta ttgttcaact      1740
gattgctatc ttctagctct ttcctgccga ataatggtct tgtttcctgc tctgttggtt      1800
tagagctgac ttctttcagc tttggtaagc ctgaaattat ggggttatgt ttaattcata      1860
ttgtctgggt ggactttcct ctcttgcatt tctgcttgaa tagaagaatt tttctctaga      1920
gagtagtttg tcatccttac tctgttgatt cagatgactc tttgtatgat ctgagaggta      1980
tactgttctg ctattctgag aagaagtatt tcagaaagat gaattaagag tacagtggac      2040
```

```
tgctcccacc tggaaacttt tatctatctc acctctggac ctgataaatt ctttatcact    2100
caggaccttg atgacgctgc tctctgaaac cctccccagc tctctctatt accgtgagaa    2160
acatcagaac tttggttccc attgcatatc gcaggtacct ctgctttcat gccatgctgt    2220 aatgagagtga ttgggtagca tgttttcatc tctttccaga ttgaaaatct gtatttctcc   2280
ctgtatatct tcaacaccta atgcacatag aactttgtag gtacctggaa aatgcaccac    2340
agttttcttt tcttttttgca gacttttcac aagtattacc aacttacaaa gaattaattt   2400
tgtaggattc tagaaagaca aatcaggaat ggtgccatat acatctttt tgattccctg     2460 ctctaaagaa tattatcagg ttaccttcct gcagagtttt aaaagaattg catatttcaa    2520
gctgactttc aggatgtaaa tataaccaaa gcaactgata tgtaaaaaat atattcaatg    2580
gcattcctag attttcttct agggtgtttt attgttttgg ttttacatt taagtcttta     2640 atccatcttg agttaatttt tgtataggta taagaaaggg gtccagtttt aattttctgc    2700
gtatggctag ccagttctcc cagcaccatt tattaaatag ggaatccttt ccctattgtt    2760 tgttttgta cggtttgtca aagattagat ggttgtagat gtgtggtctt atttctgaga    2820
tcttcattct cttccactgg tctatgtgtc tgttttttgta ccatgctttt ttggttactg   2880
tagccttgta gtatagtatg aaagatagca tgatgcctcc aggtttgttc ttttttgctta   2940 ggattgtctt ggctatacga gcttttttttt ggttctatat gaattttaaa atagtttctt   3000
ctaattgtgt gaagaatgtt aatggtagtt taatgggaat agcattgaat ctgtgaattg    3060
ctttgggcag tatggccatt tcatgatat tgattcttcc tatccatgag catgtaacgt     3120 ttttccccttc gtttgtgtcc tctctcattt ccttgagtag tggtttgtag ttctccttga   3180
agagatcctt cacttcttct gtattcctag atattttatt ctctctgtag ctattgggaa    3240
tgggagttca ttcatgattt tgctctctgc ttgccttttg ttggtgtata gggatcctgg    3300
tgacttctgc acattgattt tgtatcctga gactttaccg aagttgctta tcagcttaag    3360
aagcttttgg gctgagatga tggggttttc tagatatagg atcatgttat cttcaaacaa    3420
agacaatttg acttcctctc ttcctatttg agtacgcttt atttctttct cttgcctgat    3480
tgccctggcc agaactccca atactatatt gaataagaat ggtgagagag ggcatccttg    3540
tcttgtgcca gttttcacgg ggaatgcttc cagcttttgc ccattcagta tgatattatc    3600 tgtgggttttc tcataaaaag ctcttattat ttgagatacg ttccttcaat acctagttta   3660 ttgagagtttt ttaacatgaa gcgatgttga attgtatcga aggccttttc tgtgtctatt   3720
gagataatca tgtggttttt gtctttagtt ctgtttatgt gatgaatgac gtttattgat    3780
ttgcatatgt tgaaccggcc ttgcatcctg gggatgaagc caacttgact gtggtagata    3840
agcttttgga tgtgctgctg gatttggttt atcagtattt cattgagatt ttttgcgtcg    3900
aagttcatca gggatattgg actgaagttt tctttttgtt gtcgtatctc tgccaggttt    3960
tggtatcagg atgatgctgg cctcataaaa tgagttaggg aggagtccct ccttttcaat    4020
tgtttggaat agtttcagaa gaaagggtat cagctcctct ttgtacctct ggtagaattc    4080
aactgtaaat ccatctggtc ctggactttt tttcattagt aggctatta ttactgcctc     4140 actttcataa cttgttattg atctattcag ggatccaact tcttcctgat tcagtcttgg    4200
gagtgtgtat gcatccagga atttatccat ttcttctaga ttttctagtt tctttgcata    4260
gaggtgtttg tagtatttgc tgttggttgt ttgtacttct gtgagatcag tggtggtatc    4320
ctgtttatca tttttttattg tgtctgtttg attcttctct tatttttgac aaagctgaca   4380
```

```
aaaagaagca ataggaaaag gactctctat tcaattaatc ctactgtata tctggctagc    4440
catatgcaga aaattgaaac tgttcctgtt tcttaatcca tatacgaaaa tcaacttacg    4500
atggattaaa gacttaaatg taaaacccaa aattataaaa ccctggaata gaatataggc    4560
aatatcattc tggacatagg aatgggcaaa gattttatga gaaagacacc aaaagcaatt    4620
acaacaaaag caaaaattgg caaatgagat ctaattaaac taaagagctc tgcacagcaa    4680
aagaaactac tgtcagagtg aacaggcaac caacagaatg ggagaaaatt ttttcaatct    4740
atccatatga caaaggtcta acatccagaa tctacaagga acttaacaaa tttacaagaa    4800
aaaaggagcc ccattaaaaa gttggcaaag aacatgaaca gacacttccc agaagatatt    4860
catgtggcca ataaacatga agaaaagctc aacatcactg accattagag acgtgcatat    4920
caaaatcaca atgagatacc atctcatgtc acaatggtga ttattaaaaa gtcaaacaac    4980
atgctagtga ggttgtagag aaataagaac gcttttacac tgttggtggg aatgtcaact    5040
aattcaacca ctgtggaaga cagtgtggtg attcctcaag gatttagaac cagaaatatc    5100
attactgcat atagacccaa aggaatagaa atcattctat tacaaagata catgcacatg    5160
tatgtttatt acagcactat tcacaatagc aaagacatgg aatcaaccca aatgctcatc    5220
agtgatagac tggaaaaaga gaatgtgaa cataaacacc atggaatact atgcagcaat    5280
aaaaaggaat gagatcctgt ccttttcagg acatggatg gagttggaag ctgttatcct    5340
cagcaaacta atgcaggaac agaaaaccaa ccaccacatg ttctcactta taagtgggag    5400
ctgaacaata gaacacatgg gcacagggag gggaataaca cactggggg ccagtcaggg    5460 ggtgggggt caagctgagg gagagcatta gaaaaaatag ctaatgcatt ctgggcttaa    5520
cccatttatg cctagtgttc catttctgga atgctaagca tgtggaagtt ctttatatcc    5580
tgctcaaggt cattgccaag gtctgatttt tcacattcaa caaattgcaa cctctggcat    5640
aaatgggtta atacctaggt gatgagttga taggtgcagg aaaccaccat ggcacatgtt    5700
tatctatgta agaaacctgc acatcctaca catgtaccct ggaacttaaa aaatttaaaa    5760
tatatatgta tatatattta atatggaatt ttaaaaatta ctaatgagtt cttttatctg    5820
agtaattttg catcaacatg cttttattat ggaagagaag attcagtgag tacaaaattg    5880
cagatacatg tgtcagaaga tccctgaata taataaggct tagtattctg tgtcataatt    5940
gcctgtttgt attcctctct ggtctttaaa cttcattagg gcaaggatca actccatctt    6000
actaaccatt tgattcccta tgtattacac gatatatgac caataataag ccttcaataa    6060
atacttgtaa aataaagaat gttatgtaat aaaaaaaaa                          6099
```

<210> SEQ ID NO 6
<211> LENGTH: 141
<212> TYPE: PRT
<213> ORGANISM: Homo sapiens

<400> SEQUENCE: 6

Met Gly Ala Gly Pro Ser Leu Leu Ala Ala Leu Leu Leu Leu
1               5                   10                  15

Ser Gly Asp Gly Ala Val Arg Cys Asp Thr Pro Ala Asn Cys Thr Tyr
            20                  25                  30

Leu Asp Leu Leu Gly Thr Trp Val Phe Gln Val Gly Ser Ser Gly Ser
        35                  40                  45

Gln Arg Asp Val Asn Cys Ser Val Met Gly Pro Gln Glu Lys Lys Val
    50                  55                  60

Val Val Tyr Leu Gln Lys Leu Asp Thr Ala Tyr Asp Asp Leu Gly Asn

```
                65                  70                  75                  80
Ser Gly His Phe Thr Ile Ile Tyr Asn Gln Gly Phe Glu Ile Val Leu
                    85                  90                  95

Asn Asp Tyr Lys Trp Phe Ala Phe Lys Asp Val Thr Asp Phe Ile
                100                 105                 110

Ser His Leu Phe Met Gln Leu Gly Thr Val Gly Ile Tyr Asp Leu Pro
                115                 120                 125

His Leu Arg Asn Lys Leu Ala Met Asn Arg Arg Trp Gly
                130                 135                 140

<210> SEQ ID NO 7
<211> LENGTH: 777
<212> TYPE: DNA
<213> ORGANISM: Homo sapiens

<400> SEQUENCE: 7
atgctggtcc tttatggaca cagcacccag gaccttccgg aaaccaatgc ccgcgtagtc     60
ggagggactg aggccgggag gaattcctgg ccctctcaga tttccctcca gtaccggtct   120
ggaggttccc ggtatcacac ctgtggaggg acccttatca gacagaactg ggtgatgaca   180
gctgctcact gcgtggatta ccagaagact ttccgcgtgg tggctggaga ccataacctg   240
agccagaatg atggcactga gcagtacgtg agtgtgcaga gatcgtggt gcatccatac   300
tggaacagcg ataacgtggc tgccggctat gacatcgccc tgctgcgcct ggcccagagc   360
gttaccctca atagctatgt ccagctgggt gttctgcccc aggagggagc catcctggct   420
aacaacagtc cctgctacat cacaggctgg ggcaagacca gaccaatgg gcagctggcc   480
cagaccctgc agcaggctta cctgccctct gtggactacg ccatctgctc agctcctcc   540
tactggggct ccactgtgaa gaacaccatg gtgtgtgctg gtggagatgg agttcgctct   600
ggatgccagg gtgactctgg ggcccccctc cattgcttgg tgaatggcaa gtattctgtc   660
catggagtga ccagctttgt gtccagccgg ggctgtaatg tctccaggaa gcctacagtc   720
ttcacccagg tctctgctta catctcctgg ataaataatg tcatcgcctc caactga       777

<210> SEQ ID NO 8
<211> LENGTH: 258
<212> TYPE: PRT
<213> ORGANISM: Homo sapiens

<400> SEQUENCE: 8

Met Leu Val Leu Tyr Gly His Ser Thr Gln Asp Leu Pro Glu Thr Asn
1               5                   10                  15

Ala Arg Val Val Gly Gly Thr Glu Ala Gly Arg Asn Ser Trp Pro Ser
                20                  25                  30

Gln Ile Ser Leu Gln Tyr Arg Ser Gly Gly Ser Arg Tyr His Thr Cys
            35                  40                  45

Gly Gly Thr Leu Ile Arg Gln Asn Trp Val Met Thr Ala Ala His Cys
        50                  55                  60

Val Asp Tyr Gln Lys Thr Phe Arg Val Val Ala Gly Asp His Asn Leu
65                  70                  75                  80

Ser Gln Asn Asp Gly Thr Glu Gln Tyr Val Ser Val Gln Lys Ile Val
                85                  90                  95

Val His Pro Tyr Trp Asn Ser Asp Asn Val Ala Ala Gly Tyr Asp Ile
                100                 105                 110

Ala Leu Leu Arg Leu Ala Gln Ser Val Thr Leu Asn Ser Tyr Val Gln
            115                 120                 125
```

Leu Gly Val Leu Pro Gln Glu Gly Ala Ile Leu Ala Asn Asn Ser Pro
    130                 135                 140

Cys Tyr Ile Thr Gly Trp Gly Lys Thr Lys Thr Asn Gly Gln Leu Ala
145                 150                 155                 160

Gln Thr Leu Gln Gln Ala Tyr Leu Pro Ser Val Asp Tyr Ala Ile Cys
                165                 170                 175

Ser Ser Ser Ser Tyr Trp Gly Ser Thr Val Lys Asn Thr Met Val Cys
                180                 185                 190

Ala Gly Gly Asp Gly Val Arg Ser Gly Cys Gln Gly Asp Ser Gly Gly
                195                 200                 205

Pro Leu His Cys Leu Val Asn Gly Lys Tyr Ser Val His Gly Val Thr
    210                 215                 220

Ser Phe Val Ser Arg Gly Cys Asn Val Ser Arg Lys Pro Thr Val
225                 230                 235                 240

Phe Thr Gln Val Ser Ala Tyr Ile Ser Trp Ile Asn Asn Val Ile Ala
                245                 250                 255

Ser Asn

<210> SEQ ID NO 9
<211> LENGTH: 813
<212> TYPE: DNA
<213> ORGANISM: Homo sapiens

<400> SEQUENCE: 9

```
atgatgctcc ggctgctcag ttccctcctc cttgtggccg ttgcctcagg ctatggccca    60
ccttcctctc actcttccag ccgcgttgtc catggtgagg atgcggtccc ctacagctgg   120
ccctggcagg tttccctgca gtatgagaaa agtggaagct tctaccacac gtgtggcggt   180
agcctcatcg cccccgattg ggttgtgact gccggccact gcatctcgag ggatctgacc   240
taccaggtgg tgtttgggtga gtacaaccttt gctgtgaagg agggccccga gcaggtgatc   300
cccatcaact ctgaggagct gtttgtgcat ccactctgga accgtcgtg tgtggcctgt   360 ggcaatgaca tcgccctcat caagctctca cgcagcgccc agctgggaga tgccgtccag   420
ctcgcctcac tccctcccgc tggtgacatc cttcccaaca agacacctg ctacatcacc   480 ggctggggcc gtctctatac caatgggcca ctcccagaca agctgcagca ggcccggctg   540
cccgtggtgg actataagca ctgctccagg tggaactggt ggggttccac cgtgaagaaa   600
accatggtgt gtgctggagg gtacatccgc tccggctgca acggtgactc tggaggaccc   660
ctcaactgcc ccacagagga tggtggctgg caggtccacg gtgtgaccag ctttgtttct   720
gcctttggct gcaacttcat ctggaagccc acggtgttca ctcgagtctc cgccttcatc   780
gactggattg aggagaccat agcaagccac tag                                813
```

<210> SEQ ID NO 10
<211> LENGTH: 270
<212> TYPE: PRT
<213> ORGANISM: Homo sapiens

<400> SEQUENCE: 10

Met Met Leu Arg Leu Leu Ser Ser Leu Leu Val Ala Val Ala Ser
1               5                   10                  15

Gly Tyr Gly Pro Pro Ser Ser His Ser Ser Arg Val Val His Gly
                20                  25                  30

Glu Asp Ala Val Pro Tyr Ser Trp Pro Trp Gln Val Ser Leu Gln Tyr
                35                  40                  45

```
Glu Lys Ser Gly Ser Phe Tyr His Thr Cys Gly Gly Ser Leu Ile Ala
             50                  55                  60

Pro Asp Trp Val Val Thr Ala Gly His Cys Ile Ser Arg Asp Leu Thr
 65                  70                  75                  80

Tyr Gln Val Val Leu Gly Glu Tyr Asn Leu Ala Val Lys Glu Gly Pro
                 85                  90                  95

Glu Gln Val Ile Pro Ile Asn Ser Glu Glu Leu Phe Val His Pro Leu
            100                 105                 110

Trp Asn Arg Ser Cys Val Ala Cys Gly Asn Asp Ile Ala Leu Ile Lys
            115                 120                 125

Leu Ser Arg Ser Ala Gln Leu Gly Asp Ala Val Gln Leu Ala Ser Leu
            130                 135                 140

Pro Pro Ala Gly Asp Ile Leu Pro Asn Lys Thr Pro Cys Tyr Ile Thr
145                 150                 155                 160

Gly Trp Gly Arg Leu Tyr Thr Asn Gly Pro Leu Pro Asp Lys Leu Gln
                165                 170                 175

Gln Ala Arg Leu Pro Val Val Asp Tyr Lys His Cys Ser Arg Trp Asn
            180                 185                 190

Trp Trp Gly Ser Thr Val Lys Lys Thr Met Val Cys Ala Gly Gly Tyr
            195                 200                 205

Ile Arg Ser Gly Cys Asn Gly Asp Ser Gly Gly Pro Leu Asn Cys Pro
210                 215                 220

Thr Glu Asp Gly Gly Trp Gln Val His Gly Val Thr Ser Phe Val Ser
225                 230                 235                 240

Ala Phe Gly Cys Asn Phe Ile Trp Lys Pro Thr Val Phe Thr Arg Val
                245                 250                 255

Ser Ala Phe Ile Asp Trp Ile Glu Glu Thr Ile Ala Ser His
                260                 265                 270

<210> SEQ ID NO 11
<211> LENGTH: 8
<212> TYPE: PRT
<213> ORGANISM: Homo sapiens

<400> SEQUENCE: 11

Cys Ile Ser Arg Asp Leu Thr Tyr
1               5

<210> SEQ ID NO 12
<211> LENGTH: 8
<212> TYPE: PRT
<213> ORGANISM: Artificial Sequence
<220> FEATURE:
<223> OTHER INFORMATION: Synthetic Construct - Sequence 12

<400> SEQUENCE: 12

Gly Glu Tyr Asn Leu Ala Val Lys
1               5

<210> SEQ ID NO 13
<211> LENGTH: 8
<212> TYPE: PRT
<213> ORGANISM: Artificial Sequence
<220> FEATURE:
<223> OTHER INFORMATION: Synthetic Construct - Sequence 13

<400> SEQUENCE: 13

Pro Ile Asn Ser Glu Glu Leu Phe
1               5
```

```
<210> SEQ ID NO 14
<211> LENGTH: 8
<212> TYPE: PRT
<213> ORGANISM: Artificial Sequence
<220> FEATURE:
<223> OTHER INFORMATION: Synthetic Construct - Sequence 14

<400> SEQUENCE: 14

Gln Gln Ala Arg Leu Pro Val Val
1               5

<210> SEQ ID NO 15
<211> LENGTH: 8
<212> TYPE: PRT
<213> ORGANISM: Artificial Sequence
<220> FEATURE:
<223> OTHER INFORMATION: Synthetic Construct - Sequence 15

<400> SEQUENCE: 15

Thr Met Val Cys Ala Gly Gly Tyr
1               5

<210> SEQ ID NO 16
<211> LENGTH: 9
<212> TYPE: PRT
<213> ORGANISM: Artificial Sequence
<220> FEATURE:
<223> OTHER INFORMATION: Synthetic Construct - Sequence 16

<400> SEQUENCE: 16

Ala Phe Gly Cys Asn Phe Ile Trp Lys
1               5

<210> SEQ ID NO 17
<211> LENGTH: 16
<212> TYPE: PRT
<213> ORGANISM: Artificial Sequence
<220> FEATURE:
<223> OTHER INFORMATION: Synthetic Construct - Sequence 17

<400> SEQUENCE: 17

Met Leu Val Leu Tyr Gly His Ser Thr Gln Asp Leu Pro Glu Thr Asn
1               5                   10                  15

<210> SEQ ID NO 18
<211> LENGTH: 8
<212> TYPE: PRT
<213> ORGANISM: Artificial Sequence
<220> FEATURE:
<223> OTHER INFORMATION: Synthetic Construct - Sequence 18

<400> SEQUENCE: 18

Ala Gly Arg Asn Ser Trp Pro Ser
1               5

<210> SEQ ID NO 19
<211> LENGTH: 10
<212> TYPE: PRT
<213> ORGANISM: Artificial Sequence
<220> FEATURE:
<223> OTHER INFORMATION: Synthetic Construct - Sequence 19

<400> SEQUENCE: 19

Leu Ser Gln Asn Asp Gly Thr Glu Gln Tyr
1               5                   10
```

<210> SEQ ID NO 20
<211> LENGTH: 8
<212> TYPE: PRT
<213> ORGANISM: Artificial Sequence
<220> FEATURE:
<223> OTHER INFORMATION: Synthetic Construct - Sequence 20

<400> SEQUENCE: 20

Ser Asp Asn Val Ala Ala Gly Tyr
1               5

<210> SEQ ID NO 21
<211> LENGTH: 6
<212> TYPE: PRT
<213> ORGANISM: Artificial Sequence
<220> FEATURE:
<223> OTHER INFORMATION: Synthetic Construct - Sequence 21

<400> SEQUENCE: 21

Ala Tyr Leu Pro Ser Val
1               5

<210> SEQ ID NO 22
<211> LENGTH: 8
<212> TYPE: PRT
<213> ORGANISM: Artificial Sequence
<220> FEATURE:
<223> OTHER INFORMATION: Synthetic Construct - Sequence 22

<400> SEQUENCE: 22

Ala Ile Cys Ser Ser Ser Ser Tyr
1               5

<210> SEQ ID NO 23
<211> LENGTH: 8
<212> TYPE: PRT
<213> ORGANISM: Artificial Sequence
<220> FEATURE:
<223> OTHER INFORMATION: Synthetic Construct - Sequence 23

<400> SEQUENCE: 23

Ser Arg Gly Cys Asn Val Ser Arg
1               5

<210> SEQ ID NO 24
<211> LENGTH: 24
<212> TYPE: DNA
<213> ORGANISM: Artificial Sequence
<220> FEATURE:
<223> OTHER INFORMATION: Synthetic Construct - Sequence 24

<400> SEQUENCE: 24
tgcatctcga gggatctgac ctac                                          24

<210> SEQ ID NO 25
<211> LENGTH: 24
<212> TYPE: DNA
<213> ORGANISM: Artificial Sequence
<220> FEATURE:
<223> OTHER INFORMATION: Synthetic Construct - Sequence 25

<400> SEQUENCE: 25
ggtgagtaca accttgctgt gaag                                          24

<210> SEQ ID NO 26
<211> LENGTH: 24

```
<212> TYPE: DNA
<213> ORGANISM: Artificial Sequence
<220> FEATURE:
<223> OTHER INFORMATION: Synthetic Construct - Sequence 26

<400> SEQUENCE: 26
cccatcaact ctgaggagct gttt                                          24

<210> SEQ ID NO 27
<211> LENGTH: 24
<212> TYPE: DNA
<213> ORGANISM: Artificial Sequence
<220> FEATURE:
<223> OTHER INFORMATION: Synthetic Construct - Sequence 27

<400> SEQUENCE: 27
cagcaggccc ggctgcccgt ggtg                                          24

<210> SEQ ID NO 28
<211> LENGTH: 24
<212> TYPE: DNA
<213> ORGANISM: Artificial Sequence
<220> FEATURE:
<223> OTHER INFORMATION: Synthetic Construct - Sequence 28

<400> SEQUENCE: 28
accatggtgt gtgctggagg gtac                                          24

<210> SEQ ID NO 29
<211> LENGTH: 27
<212> TYPE: DNA
<213> ORGANISM: Artificial Sequence
<220> FEATURE:
<223> OTHER INFORMATION: Synthetic Construct - Sequence 29

<400> SEQUENCE: 29
gcctttggct gcaacttcat ctggaag                                       27

<210> SEQ ID NO 30
<211> LENGTH: 49
<212> TYPE: DNA
<213> ORGANISM: Artificial Sequence
<220> FEATURE:
<223> OTHER INFORMATION: Synthetic Construct - Sequence 30

<400> SEQUENCE: 30
atgctggtcc tttatggaca cagcacccag gaccttccgg aaaccaatg               49

<210> SEQ ID NO 31
<211> LENGTH: 24
<212> TYPE: DNA
<213> ORGANISM: Artificial Sequence
<220> FEATURE:
<223> OTHER INFORMATION: Synthetic Construct - Sequence 31

<400> SEQUENCE: 31
gccgggagga attcctggcc ctct                                          24

<210> SEQ ID NO 32
<211> LENGTH: 30
<212> TYPE: DNA
<213> ORGANISM: Artificial Sequence
<220> FEATURE:
<223> OTHER INFORMATION: Synthetic Construct - Sequence 32

<400> SEQUENCE: 32
```
ctgagccaga atgatggcac tgagcagtac                                            30

<210> SEQ ID NO 33
<211> LENGTH: 24
<212> TYPE: DNA
<213> ORGANISM: Artificial Sequence
<220> FEATURE:
<223> OTHER INFORMATION: Synthetic Construct - Sequence 33

<400> SEQUENCE: 33
agcgataacg tggctgccgg ctat                                                  24

<210> SEQ ID NO 34
<211> LENGTH: 18
<212> TYPE: DNA
<213> ORGANISM: Artificial Sequence
<220> FEATURE:
<223> OTHER INFORMATION: Synthetic Construct - Sequence 34

<400> SEQUENCE: 34
gcttacctgc cctctgtg                                                         18

<210> SEQ ID NO 35
<211> LENGTH: 24
<212> TYPE: DNA
<213> ORGANISM: Artificial Sequence
<220> FEATURE:
<223> OTHER INFORMATION: Synthetic Construct - Sequence 35

<400> SEQUENCE: 35
gccatctgct ccagctcctc ctac                                                  24

<210> SEQ ID NO 36
<211> LENGTH: 24
<212> TYPE: DNA
<213> ORGANISM: Artificial Sequence
<220> FEATURE:
<223> OTHER INFORMATION: Synthetic Construct - Sequence 36

<400> SEQUENCE: 36
agccggggct gtaatgtctc cagg                                                  24

<210> SEQ ID NO 37
<211> LENGTH: 813
<212> TYPE: DNA
<213> ORGANISM: Homo sapiens

<400> SEQUENCE: 37
atgatgctcc ggctgctcag ttccctcctc cttgtggccg ttgcctcagg ctatggccca           60
ccttcctctc gcccttccag ccgcgttgtc aatggtgagg atgcggtccc ctacagctgg          120
ccctggcagg tttccctgca gtatgagaaa agcggaagct ctaccacac ctgtggcggt           180 agcctcatcg ccccgactg ggttgtgact gccggccact gcatctcgag ctcccggacc           240
taccaggtgg tgttgggcga gtacgaccgt gctgtgaagg agggccccga gcaggtgatc          300
cccatcaact ctggggacct ctttgtgcat ccactctgga accgctcgtg tgtggcctgt          360
ggcaatgaca tcgccctcat caagctctca cgcagcgccc agctgggaga cgccgtccag          420
ctcgcctcac tccctccggc tggtgacatc cttcccaacg agacaccctg ctacatcacc          480
ggctggggcc gtctctatac caacgggcca ctcccagaca gctgcagga ggccctgctg           540 ccggtggtgg actatgaaca ctgctccagg tggaactggt ggggttcctc cgtgaagaag          600
accatggtgt gtgctggagg ggacatccgc tccggctgca atggtgactc tggaggaccc          660

| ctcaactgcc ccacagagga tggtggctgg caggtccatg gcgtgaccag ctttgtttct | 720 |
| gcctttggct gcaacacccg caggaagccc acgtgttca ctcgagtctc cgccttcatt | 780 |
| gactggattg aggagaccat agcaagccac tag | 813 |

```
<210> SEQ ID NO 38
<211> LENGTH: 270
<212> TYPE: PRT
<213> ORGANISM: Homo sapiens

<400> SEQUENCE: 38
```

| Met | Met | Leu | Arg | Leu | Leu | Ser | Ser | Leu | Leu | Val | Ala | Val | Ala | Ser |
|-----|-----|-----|-----|-----|-----|-----|-----|-----|-----|-----|-----|-----|-----|-----|
| 1 | | | | 5 | | | | | 10 | | | | | 15 |

| Gly | Tyr | Gly | Pro | Pro | Ser | Ser | Arg | Pro | Ser | Ser | Arg | Val | Val | Asn | Gly |
|  | | | 20 | | | | | 25 | | | | | 30 | | |

| Glu | Asp | Ala | Val | Pro | Tyr | Ser | Trp | Pro | Trp | Gln | Val | Ser | Leu | Gln | Tyr |
|  | | | 35 | | | | 40 | | | | | 45 | | | |

| Glu | Lys | Ser | Gly | Ser | Phe | Tyr | His | Thr | Cys | Gly | Gly | Ser | Leu | Ile | Ala |
|  | 50 | | | | | 55 | | | | | 60 | | | | |

| Pro | Asp | Trp | Val | Val | Thr | Ala | Gly | His | Cys | Ile | Ser | Ser | Ser | Arg | Thr |
| 65 | | | | | 70 | | | | | 75 | | | | | 80 |

| Tyr | Gln | Val | Val | Leu | Gly | Glu | Tyr | Asp | Arg | Ala | Val | Lys | Glu | Gly | Pro |
|  | | | | 85 | | | | | 90 | | | | | 95 | |

| Glu | Gln | Val | Ile | Pro | Ile | Asn | Ser | Gly | Asp | Leu | Phe | Val | His | Pro | Leu |
|  | | | 100 | | | | | 105 | | | | | 110 | | |

| Trp | Asn | Arg | Ser | Cys | Val | Ala | Cys | Gly | Asn | Asp | Ile | Ala | Leu | Ile | Lys |
|  | | 115 | | | | | 120 | | | | | 125 | | | |

| Leu | Ser | Arg | Ser | Ala | Gln | Leu | Gly | Asp | Ala | Val | Gln | Leu | Ala | Ser | Leu |
| 130 | | | | | 135 | | | | | 140 | | | | | |

| Pro | Pro | Ala | Gly | Asp | Ile | Leu | Pro | Asn | Glu | Thr | Pro | Cys | Tyr | Ile | Thr |
| 145 | | | | | 150 | | | | | 155 | | | | | 160 |

| Gly | Trp | Gly | Arg | Leu | Tyr | Thr | Asn | Gly | Pro | Leu | Pro | Asp | Lys | Leu | Gln |
|  | | | | 165 | | | | | 170 | | | | | 175 | |

| Glu | Ala | Leu | Leu | Pro | Val | Val | Asp | Tyr | Glu | His | Cys | Ser | Arg | Trp | Asn |
|  | | | 180 | | | | | 185 | | | | | 190 | | |

| Trp | Trp | Gly | Ser | Ser | Val | Lys | Lys | Thr | Met | Val | Cys | Ala | Gly | Gly | Asp |
|  | | 195 | | | | | 200 | | | | | 205 | | | |

| Ile | Arg | Ser | Gly | Cys | Asn | Gly | Asp | Ser | Gly | Gly | Pro | Leu | Asn | Cys | Pro |
|  | 210 | | | | | 215 | | | | | 220 | | | | |

| Thr | Glu | Asp | Gly | Gly | Trp | Gln | Val | His | Gly | Val | Thr | Ser | Phe | Val | Ser |
| 225 | | | | | 230 | | | | | 235 | | | | | 240 |

| Ala | Phe | Gly | Cys | Asn | Thr | Arg | Arg | Lys | Pro | Thr | Val | Phe | Thr | Arg | Val |
|  | | | | 245 | | | | | 250 | | | | | 255 | |

| Ser | Ala | Phe | Ile | Asp | Trp | Ile | Glu | Glu | Thr | Ile | Ala | Ser | His |
|  | | | 260 | | | | | 265 | | | | | 270 |

```
<210> SEQ ID NO 39
<211> LENGTH: 810
<212> TYPE: DNA
<213> ORGANISM: Homo sapiens

<400> SEQUENCE: 39
```

| atgataagga cgctgctgct gtccactttg gtggctggag ccctcagttg tggggacccc | 60 |
| acttacccac ttatgtgac tagggtggtt ggcggtgaag aagcgaggcc caacagctgg | 120 |
| ccctggcagg tctccctgca gtacagctcc aatggcaagt ggtaccacac ctgcggaggg | 180 |

```
tccctgatag ccaacagctg ggtcctgacg gctgcccact gcatcagctc ctccaggacc      240
taccgcgtgg ggctgggccg gcacaacctc tacgttgcgg agtccggctc gctggcagtc      300
agtgtctcta agattgtggt gcacaaggac tggaactcca accaaatctc caagggaac       360 gacattgccc tgctcaaact ggctaacccc gtctccctca ccgacaagat ccagctggcc      420 tgcctcccte ctgccggcac cattctaccc aacaactacc cctgctacgt cacgggctgg      480
ggaaggctgc agaccaacgg ggctgttcct gatgtcctgc agcagggccg gttgctggtt      540
gtggactatg ccacctgctc cagctctgcc tggtggggca gcagcgtgaa aaccagtatg      600
atctgtgctg ggggtgatgg cgtgatctcc agctgcaacg gagactctgg cgggccactg      660
aactgtcagg cgtctgacgg ccggtggcag gtgcacggca tcgtcagctt cgggtctcgc      720
ctcggctgca actactacca caagccctcc gtcttcacgc gggtctccaa ttacatcgac      780
tggatcaatt cggtgattgc aaataactaa                                        810
```

<210> SEQ ID NO 40
<211> LENGTH: 269
<212> TYPE: PRT
<213> ORGANISM: Homo sapiens

<400> SEQUENCE: 40

```
Met Ile Arg Thr Leu Leu Ser Thr Leu Val Ala Gly Ala Leu Ser
1               5                   10                  15

Cys Gly Asp Pro Thr Tyr Pro Pro Tyr Val Thr Arg Val Val Gly
                20                  25                  30

Glu Glu Ala Arg Pro Asn Ser Trp Pro Trp Gln Val Ser Leu Gln Tyr
            35                  40                  45

Ser Ser Asn Gly Lys Trp Tyr His Thr Cys Gly Gly Ser Leu Ile Ala
    50                  55                  60

Asn Ser Trp Val Leu Thr Ala Ala His Cys Ile Ser Ser Ser Arg Thr
65                  70                  75                  80

Tyr Arg Val Gly Leu Gly Arg His Asn Leu Tyr Val Ala Glu Ser Gly
                85                  90                  95

Ser Leu Ala Val Ser Val Ser Lys Ile Val Val His Lys Asp Trp Asn
            100                 105                 110

Ser Asn Gln Ile Ser Lys Gly Asn Asp Ile Ala Leu Leu Lys Leu Ala
        115                 120                 125

Asn Pro Val Ser Leu Thr Asp Lys Ile Gln Leu Ala Cys Leu Pro Pro
    130                 135                 140

Ala Gly Thr Ile Leu Pro Asn Asn Tyr Pro Cys Tyr Val Thr Gly Trp
145                 150                 155                 160

Gly Arg Leu Gln Thr Asn Gly Ala Val Pro Asp Val Leu Gln Gln Gly
                165                 170                 175

Arg Leu Leu Val Val Asp Tyr Ala Thr Cys Ser Ser Ser Ala Trp Trp
            180                 185                 190

Gly Ser Ser Val Lys Thr Ser Met Ile Cys Ala Gly Gly Asp Gly Val
        195                 200                 205

Ile Ser Ser Cys Asn Gly Asp Ser Gly Gly Pro Leu Asn Cys Gln Ala
    210                 215                 220

Ser Asp Gly Arg Trp Gln Val His Gly Ile Val Ser Phe Gly Ser Arg
225                 230                 235                 240
```

```
Leu Gly Cys Asn Tyr Tyr His Lys Pro Ser Val Phe Thr Arg Val Ser
            245                 250                 255
Asn Tyr Ile Asp Trp Ile Asn Ser Val Ile Ala Asn Asn
            260                 265
```